US011865114B2

(12) United States Patent
Ramachandra et al.

(10) Patent No.: US 11,865,114 B2
(45) Date of Patent: Jan. 9, 2024

(54) METHOD FOR TREATING DISEASES USING SMARCA2/4 DEGRADERS

(71) Applicant: Aurigene Discovery Technologies Limited, Bangalore (IN)

(72) Inventors: Muralidhara Ramachandra, Bangalore (IN); Leena Khare Satyam, Bangalore (IN); Sanjita Sasmal, Hyderabad (IN); Susanta Samajdar, Bangalore (IN)

(73) Assignee: Aurigene Oncology Limited, Bangalore (IN)

( * ) Notice: Subject to any disclaimer, the term of this patent is extended or adjusted under 35 U.S.C. 154(b) by 349 days.

(21) Appl. No.: 17/018,811

(22) Filed: Sep. 11, 2020

(65) Prior Publication Data
US 2021/0077486 A1     Mar. 18, 2021

(30) Foreign Application Priority Data
Sep. 12, 2019   (IN) .............................. 201941036639

(51) Int. Cl.
*A61K 31/50* (2006.01)
*A61K 31/501* (2006.01)
*A61P 35/00* (2006.01)
*G01N 33/574* (2006.01)

(52) U.S. Cl.
CPC ............ *A61K 31/501* (2013.01); *A61P 35/00* (2018.01); *G01N 33/57434* (2013.01)

(58) Field of Classification Search
CPC .................................................... A61K 31/501
See application file for complete search history.

(56) References Cited

U.S. PATENT DOCUMENTS

| 2016/0032402 A1 | 2/2016 | Jagani et al. |
| 2016/0130663 A1 | 5/2016 | Kohno et al. |
| 2018/0258491 A1 | 9/2018 | Jagani et al. |
| 2020/0069669 A1 | 3/2020 | Grassian et al. |

FOREIGN PATENT DOCUMENTS

| EP | 3020828 A1 | 5/2016 | |
| WO | 2014150751 A3 | 9/2014 | |
| WO | 2016138114 A1 | 9/2016 | |
| WO | 2017030814 A1 | 2/2017 | |
| WO | 2017201449 | 11/2017 | |
| WO | 2018160636 A1 | 9/2018 | |
| WO | WO-2019207538 A1 * | 10/2019 | ........... C07D 401/14 |

OTHER PUBLICATIONS

Hoffman et al., "Functional epigenetics approach identifies BRM/SMARCA2 as a critical synthetic lethal target in BRG1-deficient cancers", PNAS Feb. 25, 2014. vol. 111 (8), pp. 3128-3133.
Karnezis et al., "Dual loss of the SWI/SNF complex ATPases SMARCA4/BRG1 and SMARCA2/BRM is highly sensitive and specific for small cell carcinoma of the ovary, hypercalcaemic type" J Pathol. Feb. 1, 2016. vol. 238 (3), pp. 389 400.
Vangamudi et al., "The SMARCA2/4 ATPase Domain Surpasses the Bromodomain as a Drug Target in SWI/SNF- Mutant Cancers: Insights from cDNA Rescue and PFI-3 Inhibitor Studies" Cancer Res. Sep. 15, 2015.vol. 75 (18), pp. 3865-3878.
Nandi et al., "The ubiquitin-proteasome system" J. Biosci. Mar. 2006. vol. 31 (1), pp. 137-155 Jin et al., Role of PD-1 in Regulating T-Cell Immunity. Current Topics in Microbiology and Immunology (2010) published online: Sep. 11, 2010 350: pp. 17-37.
Shen et al., "Targeting the ubiquitin-proteasome system for cancer therapy" Expert Opin Ther Targets. 2013. vol. 17 (9), pp. 1091-1108.
Huang et al., "Drugging the undruggables: exploring the ubiquitin system for drug development" Cell Research. 2016. vol. 26, pp. 484-498.
Li et al., "Interrogating Interactions and Modifications of Histones in Live Cells", Cell Chemical Biology, Jan. 18, 2018. vol. 25, pp. 1-10.
Bai et_al., "Targeted degradation of BET proteins in triple-negative breast cancer" Cancer Res. May 1, 2017, vol. 77 (9), pp. 2476-2487.
Tan et al., "Androgen receptor: structure, role in prostate cancer and drug discovery" Acta Pharmacol Sin. Jan. 2015, vol. 36 (1), pp. 3-23.
Jin et al., "BAF53A regulates androgen receptor-mediated gene expression and proliferation in LNCaP cells" Biochem Biophys Res Commun. Oct. 28, 2018, vol. 505 (2), pp. 618-623.
Ding et al., "Chromatin remodeling ATPase BRG1 and PTEN are synthetic lethal in prostate cancer" J Clin Invest. Jan. 4, 2019, vol. 129(2), pp. 759-773.
Holzbeierlein et al, "Gene Expression Analysis of Human Prostate Carcinoma during Hormonal Therapy Identifies Androgen-Responsive Genes and Mechanisms of Therapy Resistance" Am. J. Path. Jan. 2004, vol. 164 (1), pp. 217-227.
Yang et al., "lncRNA-dependent mechanisms of androgen-receptor-regulated gene activation programs" Nature. Aug. 29, 2013, vol. 500 (7464), pp. 598-602.
Farnaby et al., "BAF complex vulnerabilities in cancer demonstrated via structure-based PROTAC design" Nature Chemical Biology, 2019, 15, 672-680.
International Search Report issued in connection with PCT/IB2020/058449 dated Sep. 11, 2020.

* cited by examiner

*Primary Examiner* — Shawquia Jackson
(74) *Attorney, Agent, or Firm* — Benjamin Aaron Adler

(57) ABSTRACT

The present invention provides a method of treating a disease or disorder with at least one SMARCA2/4 degrader, in a subject who are responders to such treatment based on the presence of tumor specific alterations described therein. The present invention also provides the methods for treating prostate cancer in the subjects who are likely to respond to treatment with SMARCA2/4 degraders.

8 Claims, 3 Drawing Sheets

METHOD FOR TREATING DISEASES USING SMARCA2/4 DEGRADERS

CROSS-REFERENCE TO RELATED APPLICATIONS

This non-provisional application claims the benefit under 35 U.S.C. § 119(a) of Indian provisional patent application number 201941036639, filed on Sep. 12, 2019; the contents of which are hereby incorporated by reference in their entirety.

BACKGROUND OF THE INVENTION

Field of the Invention

The present invention relates to methods for treating diseases or disorders in a subject who is likely to respond to treatment with SMARCA2/4 degraders. The present invention also relates to methods of determining the responsiveness of a subject to treatment with SMARCA2/4 degraders.

Description of the Related Art

Prostate cancer (PrCa), the most common cancer in men, is the second leading cause of cancer death in men in the United States and is the fifth leading cause of cancer death in men worldwide. The present invention is based on the identification of biomarkers to predict the sensitivity of prostate cancer cells and thus therapeutic responsiveness of prostate cancer patients to degraders of SMARCA2/4, the catalytic subunits of SWI/SNF chromatin remodelling complex. Specifically, the invention is based on the novel finding that degradation of SMARCA2/4 function blocks the growth of prostate cancer cells with one or more of the conditions among a) presence of androgen receptor (AR), b) mutation in tumor suppressor gene PTEN and c) presence of TMPRSS2-ERG genes fusion. The invention represents a significant advance over current knowledge in the field, as no such biomarkers have been systematically identified to date to predict cellular sensitivity with SMARCA2/4 degraders.

Androgen receptor (AR) is a steroid receptor transcriptional factor for testosterone and dihydrotestosterone. AR plays pivotal roles in PrCa, especially castration-resistant prostate cancer (CRPC). Androgen deprivation therapy can suppress hormone-naïve prostate cancer, but prostate cancer changes AR and adapts to survive under castration levels of androgen. These mechanisms include AR point mutations, AR overexpression, changes of androgen biosynthesis, constitutively active AR splice variants without ligand binding, and changes of androgen cofactors. Studies of AR in CRPC revealed that AR is still active in CRPC, and it remains as a potential target to treat CRPC. Enzalutamide is a second-generation antiandrogen effective in patients with CRPC before and after taxane-based chemotherapy. However, CRPC is still incurable and can develop drug resistance. Understanding the mechanisms of this resistance can enable new-generation therapies for CRPC (Tan et al. Acta Pharmacol Sin. 2015 January; 36(1): 3-23).

Studies have shown that the SWI/SNF complex regulates androgen receptor-mediated gene expression and proliferation in prostate cancer cell lines (Jin et al., Biochem Biophys Res Commun. 2018, October 28; 505(2): 618-623). However, there are no available data on a therapeutic agent targeting the components of SWISNF complex.

Genetic and epigenetic alterations, including but not limited to deletion of phosphatase and tensin homolog (PTEN), TMPRSS2-ERG translocation, SPOP mutation, and Myc amplification facilitate disease progression in PrCa. Loss of PTEN and hyperactivation of PI3K/AKT signaling are recognized as tumor drivers pathologically linked to PrCa. Approximate 30% of primary tumors and up to 70% of metastatic cancer exhibit loss of heterozygosity at the PTEN gene locus. Similarly, genetically engineered mice (GEMs) have revealed a key role of PTEN signaling in PrCa. Prostate-specific deletion of Pten (PtenPC−/−) results in the development of prostatic adenocarcinoma after a long latency. Furthermore, Pten loss functionally cooperates with other signal alterations, such as deletion of Tp53 or Nkx3.1 and overexpression of ERG or KrasG12D, to produce full-blown disease in mice. Together, these results highlight the functional importance of PTEN in prostate tumorigenesis. However, pharmacological targeting PTEN or PI3K/AKT pathway remains a major hurdle in disease intervention.

A publication (Ding et al., J Clin Invest. 2019; 129(2): 759-773) has shown that higher SMARCA4 expression in tumors with low PTEN expression was associated with a worse clinical outcome. Genetically engineered mice (GEMs) and organoid assays confirmed that ablation of PTEN sensitized the cells to SMARCA4 depletion. Mechanistically, PTEN loss stabilized SMARCA4 protein through the inhibition of the AKT-GSK3b-FBXW7 axis. Increased SMARCA4 expression in PTEN-deficient PrCa cells led to chromatin remodeling into configurations that drive a pro-tumorigenic transcriptome, causing cells to become further addicted to SMARCA4. Furthermore, they showed in pre-clinical models that BRG1 antagonist selectively inhibited the progression of PTEN-deficient prostate tumors. However, using reported bromodomain inhibitors of SMARCA4, we could not observe sensitivity of PTEN-deficient prostate cancer cell lines consistent with the lack of anti-proliferative activity with the use of SMARCA2/4 inhibitors by a number of groups.

Approximately half of all prostate cancers harbor a translocation between the transcription factor ERG and the androgen regulated gene TMPRSS2. As a result, ERG is expressed at high levels in the prostate where it is not normally expressed. Several mouse models indicate a causal role in the development of prostate cancer, however, the exact role of TMPRSS2-ERG in tumorigenesis is unclear, making it difficult to target its function therapeutically. In addition, transcription factors have been historically difficult to target pharmacologically with small molecules.

A recent study (Sandoval et al., 2018, Molecular Cell 71, 1-13) has shown that the binding of the ERG transcription factor to SWI/SNF complex drives genome-wide retargeting and gene regulation. They also showed that the ATPase activity of the SWI/SNF complex (present within the SMARCA2 and SMARCA4 present) is required for ERG-mediated target gene regulation in cell line and organoid models, demonstrating an interdependency between ERG and BAF complexes in prostate cancer. However, there are no reports describing selective degradation of SMARCA2/4 as a therapeutic approach to target prostate cancers.

The findings described above highlight the role of AR, PTEN deletion and the presence of TMPRSS2-ERG fusion in prostate cancer and the requirement of a functional SWI/SNF complex including functional SMARCA2/4 for these changes to support prostate cancer progression. However, there are no reports that indicate the degradation of SMARCA2/4 can lead to anti-proliferative activity as a result of synthetic lethal relationship.

There are many reports in the literature which suggest a patient's genetic profile can be determinative to a patient's responsiveness to any particular therapeutic treatment. Given the fact that numerous therapies are available to an individual afflicted with cancer, a determination of the patient's genetic factors that influence a response to a particular drug, could be used to provide such patient with a personalized treatment regime. Such personalized treatment regimens offer the potential to attain maximum therapeutic benefit to the patient while minimizing related side effects that can be associated with alternative and less effective treatment regimens. Thus, there is a need to identify factors which can be used to predict whether a patient is likely to respond to a therapeutic treatment. Particularly, it is important to determine such predictive factors in the field of cancer biology, and to therapeutically exploit discoveries pertaining to key synthetic lethal nodes in prostate cancer.

SUMMARY OF THE INVENTION

The present invention is based on the novel finding that inhibition of SMARCA2/4 function by means of SMARCA2/4 degraders (Compound of formula (I)) blocks the growth of prostate cancer cells harboring tumor specific alterations among dependence of androgen receptor (AR), mutation in PTEN, presence of TMPRSS2-ERG gene fusions due either to inactivating mutations in respective genes or loss of expression of respective genes through alternative mechanism other than inactivating mutations. The present invention provides a significant advancement over current knowledge in the field, as tumor specific alterations in androgen receptor, PTEN, TMPRSS2 and ERG have not been systematically identified to date predicting cellular sensitivity with SMARCA2/4 degraders. The present invention provides methods for determination of responsiveness of a subject to treatment with SMARCA2/4 degraders based on tumor specific alterations or modifications.

In one aspect, the present invention provides a method of treating a disease or disorder in a subject in need thereof comprising:
  a) identifying the subject as a responder to treatment with at least one SMARCA2/4 degraders via the steps of:
    i. isolating a biological sample from the subject;
    ii. determining the presence of tumor specific alterations;
    iii. identifying the subject as a responder to said treatment if at least one of the tumor specific alterations is present; and
  b) administering a therapeutically effective amount of at least one SMARCA2/4 degrader to the subject who is identified to respond to the treatment, thereby treating the disease or disorder.

In another aspect, the present invention provides a method of treating a disease or disorder in a subject in need thereof, comprising:
  a) isolating a biological sample from the subject;
  b) identifying the subject as a responder for treatment with at least one SMARCA2/4 degraders if at least one tumor specific alteration is present in the sample; and
  c) administering a therapeutically effective amount of at least one SMARCA2/4 degrader to the subject, thereby treating the disease or disorder.

In yet another aspect, the present invention provides a method of selecting a patient with prostate cancer for treatment with a SMARCA2/4 degrader, comprising:

a) isolating a biological sample from the patient;
  b) determining a presence of at least one tumor specific alteration in the biological sample; wherein the tumor specific alteration comprises:
    a mutation, an amplification, or an overexpression of Androgen Receptor (AR) gene;
    a loss of function or a deleterious mutation in phosphatase and tensin homolog (PTEN); or
    a genomic rearrangement that results in translocation between TMPRSS2 and ERG genes;
  c) selecting the patient with at least one tumor specific alteration present for the treatment with the SMARCA2/4 degrader; and
  d) administering a therapeutically effective amount of at least one SMARCA2/4 degrader to the selected patient.

DETAILED DESCRIPTION OF THE INVENTION

Figure 1:
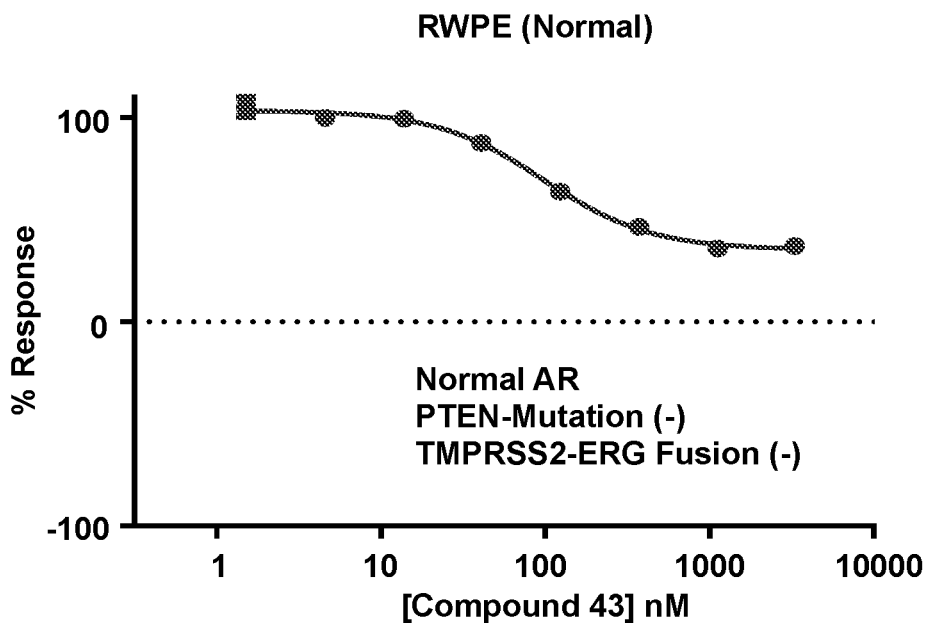
FIG. 1: Effect of SMARCA2/4 degrader of present invention in normal RWPE cells.

Each embodiment is provided by way of explanation of the invention, and not by way of limitation of the invention. In fact, it will be apparent to those skilled in the art that various modifications and variations can be made to the compounds, compositions, and methods described herein without departing from the scope or spirit of the invention. For instance, features illustrated or described as part of one embodiment can be applied to another embodiment to yield a still further embodiment. Thus, it is intended that the present invention includes such modifications and variations and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In certain embodiments, the present invention provides a method of treating a disease or disorder in a subject in need thereof comprising:
  a) identifying the subject as a responder for treatment with at least one SMARCA2/4 degraders via the steps of:
    i. isolating a biological sample from the subject;
    ii. determining the presence of tumor specific alterations;

iii. identifying the subject as a responder to the said treatment if at least one of tumor specific alterations is present; and
b) administering a therapeutically effective amount of at least one SMARCA2/4 degrader to the subject who is identified to respond to the treatment, thereby treating the disease or disorder.

In certain embodiments, the present invention provides a method of treating a disease or disorder in a subject in need thereof, comprising:
a) isolating a biological sample from the subject;
b) identifying the subject as a responder for treatment with at least one SMARCA2/4 degrader if at least one tumor specific alterations is present in the sample; and
c) administering a therapeutically effective amount of at least one SMARCA2/4 degrader to the subject, thereby treating the disease or disorder.

In certain embodiments, the present invention provides a method of treating a disease or disorder in a subject in need thereof, wherein,
a. the subject is identified as a moderate responder to the treatment with the SMARCA2/4 degraders if one tumor specific alteration is present; and
b. the subject is identified as a high responder to the treatment with the SMARCA2/4 degraders if at least two tumor specific alterations are present.

In certain embodiments, the tumor specific alteration of present invention is:
a) a mutation, an amplification, or an overexpression of Androgen Receptor (AR) gene;
b) a loss of function or a deleterious mutation in phosphatase and tensin homolog (PTEN); or
c) a genomic rearrangement that results in translocation between TMPRSS2 and ERG genes.

In certain embodiments, the tumor specific alterations are: loss of function or deleterious mutation in phosphatase and tensin homolog (PTEN); and at least one of:
a mutation, an amplification, or an overexpression of Androgen Receptor (AR) gene; and a genomic rearrangement that results in translocation between TMPRSS2 and ERG genes.

In certain embodiments, the tumor specific alterations are:
a mutation, an amplification, or an overexpression of Androgen Receptor (AR) gene; and at least one of:
a loss of function or a deleterious mutation in phosphatase and tensin homolog (PTEN) and a genomic rearrangement that results in translocation between TMPRSS2 and ERG genes.

In certain embodiments, the tumor specific alterations are:
genomic rearrangement that results in translocation between TMPRSS2 and ERG genes; and at least one of:
a mutation, an amplification, or an overexpression of Androgen Receptor (AR) gene; and a loss of function or a deleterious mutation in phosphatase and tensin homolog (PTEN).

In certain embodiments, the method described in the present invention, further comprise determining the subject afflicted with cancer comprises any one of:
a mutation, an amplification, or an overexpression of Androgen Receptor (AR) gene;
a loss of function or a deleterious mutation in phosphatase and tensin homolog (PTEN); and
a genomic rearrangement that results in translocation between TMPRSS2 and ERG genes.

In certain embodiments, the present invention provides a method of treating a disease or disorder in a subject in need thereof comprising:
a) identifying the subject as a responder for treatment with at least one SMARCA2/4 degraders via the steps of:
i. isolating a biological sample from the subject;
ii. determining the presence of tumor specific alterations; wherein tumor specific alteration is selected from:
a mutation, an amplification, or an overexpression of Androgen Receptor (AR) gene;
a loss of function or a deleterious mutation in phosphatase and tensin homolog (PTEN); and
a genomic rearrangement that results in translocation between TMPRSS2 and ERG genes;
iii. identifying the subject as a responder to said treatment if at least one of the tumor specific alterations is present; and
b) administering a therapeutically effective amount of at least one SMARCA2/4 degrader to the subject who is identified to respond to the treatment, thereby treating the disease or disorder.

In certain embodiments, the androgen receptor (AR) is wild-type AR. In certain embodiments, the androgen receptor (AR) is a mutated AR.

In certain embodiments, a mutation, an amplification, or an overexpression of Androgen Receptor (AR) gene is referred to as condition A.

In certain embodiments, a loss of function or a deleterious mutation in phosphatase and tensin homolog (PTEN) is referred to as condition B.

In certain embodiments, a genomic rearrangement that results in translocation between TMPRSS2 and ERG genes is referred to as condition C.

In certain embodiments, the tumor specific alterations referred to as condition A also includes expression of constitutively active AR variants, intra-tumoural androgen synthesis and promiscuous AR activation by another factor. In certain embodiments, condition A is deregulation (causing over-expression of AR), mutation of AR (gain of function), alternative splicing (causing AR to be constitutively active), co-activator gain of function or loss of co-repressor function, and intracrine androgen synthesis.

In certain embodiments, condition A is gain of function AR mutations or loss of function AR mutations.

In certain embodiments, the tumor specific alteration in androgen receptor (AR) is present in:
i. the amino terminal activation domain (NTD) of AR;
ii. the DNA-binding domain (DBD) of AR;
iii. the hinge region (HR) and (IV) of AR; or
iv. the carboxyl ligand-binding domain (LBD) of AR.

In certain embodiments, mutations in AR gene is selected from: single point mutations resulting in amino acid substitutions or premature stop codons; nucleotide insertions or deletions most often leading to a frame shift and premature rumination; complete or partial gene deletions; and intronic mutations causing alternative splicing.

In certain embodiments, the tumor specific alteration in androgen receptor is RNA-based androgen receptor (AR) splicing variants (AR-Vs), including but not limited to, AR-V1, AR-V2, AR-V3, AR-V4, AR-V5, AR-V6, AR-V7, AR-V567es, AR-V9, or AR-V12 together with additional tumor specific alterations including, but not limited to, DNA- and/or RNA-based mutation, indels, copy number variation, gene fusions from biological samples, e.g., plasma, serum, urine, and saliva etc.

In certain embodiments, the mutated AR is a splice variant and/or truncated AR. In additional embodiments, the mutated AR can be a splice variant and/or truncated AR, with C-terminal loss and therefore lacking ligand-binding domain (LBD). Exemplary mutations include, for example, E43G, L54S, Q58L, L57Q, Q64R, AQ86, Q112H, G142V, E166S, K180R, L192F, Q198G, E211E, D221H, N222D, T227C, M266T, P269S, A251V, E253K, S296R, P334F, P340L, A356V, P390L, G414S, W433L, T438P, T438I, L444S, G449D, G451D, G456S, G457D, R484C, T497I, A498T, P499P, V508L, G524S, G524D, D528G, AL547, AP554, T573A, L574P, K580R, A586V, A587S, L594M, K609E, R629Q, K630T, S646D, S647N, E665D, Q670R, I672T, G683A, V716M, V715M, L701H, L720E, A721T, V730M, R726L, L744V, A748V, M749I, G750S, F754L, T755A, V757A, S759P, Y763C, W741C, F747L, N756A, V757I, R760K, W741X, AG743, W751X, S782N, R786X, W7960, L797P, Q798E, S791P, I799P, L830P, R846G, Q867X, H874Y, T877A, T877S, V866M, L880Q, L872P, D879G, M886I, A896T, Q902R, F891L, G909Q, Q919R, D890N, M895V, and K910R. For example, the amino acid substitutions are: T877A (T878A), D879G (D878G), W741C, W741L, M749L, R629Q, G142V, P533S, T575A, H874Y or F876L. These point mutations may be categorized into the three main regions of the steroid receptor protein:

1) LBD mutants (T877A, D879G, W741C. W741L, M749L, H874Y, F876L) and mutations in the LBD may have altered ligand binding due to receptor protein conformation changes or alterations in amino acid R groups in the ligand binding pocket or conformation resulting in loss of ligand binding, loss of ligand recognition, switching of antagonist to agonist, and/or ligand promiscuity;

2) NTD or hinge region mutants (R629Q, G142V, P533S) that may affect the ability of receptor transactivation, interaction with the transcription machinery or cofactors/regulators and result in alterations of receptor functions such as DNA binding, regulating gene expression, or nuclear translocation; or 3) DBD mutants (T575A) that may affect the receptor's ability to regulate of gene expression. Examples include: H874Y mutation in the androgen receptor has been shown to allow estradiol, progesterone, hydrocortisone, flutamide, and bicalutamide binding in 22Rv1 and CWR22RV1 cells; D878G has been shown to confer loss of DHT and testosterone binding and activity; W741C mutations confers bicalutamide and flutamide as agonists; F876L changes ARN-509 and enzalutamide from antagonists to agonists; M749L confers a hypersensitivity to estradiol; T575A leads to preferential binding to AR-nonspecific motifs, i.e. GRE; R629Q leads to gain of function with DHT.

In certain embodiments, splice variants include exon skipping, cryptic splicing donor/acceptor usage, and cryptic exon inclusion. Variants that have been identified include AR-V1, AR-V2, AR-V3, AR-V4. AR-V5, AR-V6, ARV7, AR-V567es, AR-V7, AR-V9, AR-V12, AR-V13 and AR-V14. (See, e.g. US Patent Application No. 2011/0110926, U.S. Pat. No. 8,133,724, and US Patent Application No. 2013/0130241). Generally, the androgen receptor variants are lacking some or all of the LBD and/or that portion of the carboxyl terminal of the androgen receptor protein that confers ligand binding.

In other embodiments, the AR tumor specific alteration is AR-T878A or other related mutation, copy number gain, RNA over expression, and among others.

In certain embodiments, mutations in AR gene is single point mutations. In some other embodiments, mutated AR can carry a point mutation such as T877A (T878A), D879G, (D878G), W741C, W741L, M749L, R629Q, G142V, P533S, T575A, H874Y or F876L.

In certain embodiments, the present invention provides a method comprising: assaying the presence of one or more androgen receptor gene splice variants (AR-Vs) and additional tumor specific alterations such as mutation, indels, copy number variation, gene fusions etc. in a biological sample from the subject.

In certain embodiments, the tumor specific alteration of present invention includes AR amplification. In certain embodiments, AR amplification is the tumor specific alteration which is resulted after androgen deprivation therapy. Such AR amplification can sometimes be linked AR overexpression.

In certain embodiments, the tumor specific alteration is a loss of function mutation of the PTEN gene.

In certain embodiments, mutations in the PTEN gene include mutations in exon 1, exon 2, exon 3, exon 4, exon 5, exon 6, exon 7, exon 8 or exon 9. In some embodiments, mutations in the PTEN gene include G20STOP, R55G, T38G, E91Q, R387STOP, H118Y, I101A, I135V, Q150G, Q110STOP, P95S, A164STOP, 564, c.761-765del, c.672-673Ins, c.224Ins, D223N, E201STOP, D326N, H272Y, T348I, K344R or T382S.

In certain embodiments, mutations in the PTEN gene include mutations in exon 5 or exon 8. In some embodiments, mutations in the PTEN gene include E91Q, R387STOP, H118Y, I101A, I135V, Q150G, Q110STOP, P95S, A164STOP, E201STOP, D326N or H272Y.

In certain embodiments, the tumor specific alteration of the present invention is gene fusion having a 5' portion from a transcriptional regulatory region of an androgen regulated gene (ARG) and a 3' portion from an ETS family member gene, wherein the presence of the gene fusion is indicative of prostate cancer in a subject.

In certain embodiments, androgen regulated gene (ARG) is TMPRSS2 or PSA. In certain particular embodiments, androgen regulated gene (ARG) is TMPRSS2.

In certain embodiments, the ETS family member gene is ERG, ETV (ER81), FLI1, ETS1, ETS2, ELK1, ETV6 (TEL1)5 ETV7 (TEL2), GABPα, ELF1, ETV4 (EAF; PEA3), ETV5 (ERM), ERF, PEA3/E1AF, PU.1, ESE1/ESX, SAP (ELK4), ETV3 (METS), EWS/FLI1, ESE1, ESE2 (ELF5), ESE3, PDEF, NET (ELK3; SAP2), NERF (ELF2) or FEV. In certain embodiments, the ETS family member gene is ERG.

In certain embodiments, gene fusion having a 5' portion from a transcriptional regulatory region of an androgen regulated gene (ARG) and a 3' portion from an ETS family member gene causes the overexpression of ERG in the prostate.

In some embodiments, the biological sample is a sample of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascetic fluid, tumor cyst fluid, amniotic fluid, or a combination thereof. In one embodiment, the biological sample is a sample of blood, plasma, serum, urine, sputum, spinal fluid, cerebrospinal fluid, pleural fluid, lymph fluid, fluid of the respiratory, intestinal, and genitourinary tracts, saliva, fluid from the lymphatic system, semen, cerebrospinal fluid, ascetic fluid, tumor cyst fluid, amniotic fluid, or a combination thereof.

In certain embodiments, the tumor specific alterations of the present invention are determined by using the methods, but not limited to, Next-Generation Sequencing (NGS), immunohistochemistry, mass spectrometry (MS), liquid chromatograph mass spectrometry (LC-MS), quantitative PCR, RNA sequencing (RNAseq) or fluorescence activated cell sorting (FACS) analysis, fluorescence in situ hybridization (FISH) analysis. In certain embodiments, the tumor specific alterations are determined by using Next-Generation Sequencing (NGS).

In certain embodiments, the present invention provides a method of treating prostate cancer in a subject in need thereof, the method comprising:
  a) isolating a biological sample from the subject;
  b) identifying the subject as a responder for treatment with at least one SMARCA2/4 degrader if at least one of the tumor specific alterations is present in the sample; and
  c) administering a therapeutically effective amount of at least one SMARCA2/4 degrader to the subject, thereby treating the prostate cancer.

In certain embodiments, the present invention provides a method of treating a disease or disorder in a subject in need thereof comprising:
  a) identifying the subject as a responder to treatment with at least one SMARCA2/4 degraders in combination with another therapeutic agent via the steps of:
    i. isolating a biological sample from the subject;
    ii. determining the presence of tumor specific alterations;
    iii. identifying the subject as a responder to the said treatment if at least one of the tumor specific alterations is present; and
  b) administering a therapeutically effective amount of at least one SMARCA2/4 degrader to the subject who is identified to respond to the treatment, thereby treating the disease or disorder.

In one embodiment, potential therapeutic agents include but not restricted to biologic agents, Immune checkpoint modulators, and chemotherapeutic agents such as cytotoxic agents.

As used herein, an immune checkpoint modulator is an antagonist molecule that antagonizes the activity of PD-1, PD-L1 or CTLA-4. Exemplary immune checkpoint modulator include, but not limited to:
  i. PD-1 inhibitors such as Pembrolizumab (formerly MK-3475 or lambrolizumab, Keytruda®), Nivolumab (Opdivo®), pidilizumab, AMP-224, AMP-514, PDR001, and cemiplimab.
  ii. PD-L1 inhibitors such as Atezolizumab (Tecentriq®), Avelumab (Bavencio®), Durvalumab (Imfinzi®), BMS-936559, CK-301 (Iwai, et ak, Journal of Biomedical Science, (2017) 24:26)
  iii. CTLA4 antagonists such as Ipilimumab, also known as MDX-010 or MDX-101, a human anti-CTLA4 antibody, preferably administered at a dose of about 10 mg/kg, and Tremelimumab a human anti-CTLA4 antibody, preferably administered at a dose of about 15 mg/kg. See also Sammartino, et a, Clinical Kidney Journal, 3(2): 135-137 (2010), published online December 2009.

In one embodiment, chemotherapeutic agent are chemical compounds useful in the treatment of cancer. In one embodiment, compounds of the present invention, or a pharmaceutically acceptable composition thereof, are administered in combination with chemotherapeutic agent which includes erlotinib (TARCEVA®, Genentech/OSI Pharm.), bortezomib (VELCADE®, Millennium Pharm.), disulfiram, epigallocatechin gallate salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®., Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5a-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancrati statin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γii and calicheamicin coll (Angew Chem. Intl. Ed. Engl. 1994 33: 183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''- trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, 111.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA*); ibandronate; CPT-11; topoisomerase inhibitor RFS 2000; difluoromethylornithine (DMFO); retinoids such as retinoic acid; and pharmaceutically acceptable salts, acids and derivatives of any of the above.

In one embodiment, biologics agents include antibodies such as alemtuzumab (Campath), bevacizumab (A VASTEST®, Genentech); cetuximab (ERBITUX®, Imclone); panitumumab (VECTIBIX®, Amgen), rituximab (RITUXAN®, Genentech/Biogen Idee), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgGi λ antibody genetically modified to recognize interleukin-12 p40 protein.

In certain embodiments, the present invention is directed to methods for inhibiting the progression of, reduce the size of, the aggregation of, reduce the volume of, and/or otherwise inhibit the growth of a tumor by using at least one of SMARCA2/4 degraders. Also provided herein are methods for treating underlying disease, e.g., prostate cancer, and thereby extending the survival of the subject.

In certain embodiments, the present invention provides a method of inhibiting the growth of a tumor in a subject who is the responder to the treatment with a SMARCA2/4 degrader, in need thereof, wherein the method comprising administering to the said subject an effective amount of a SMARCA2/4 degrader.

In certain embodiments, the present invention provides a method of inhibiting the growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by tumor volume.

In certain embodiments, the present invention provides a method of inhibiting the growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by the absolute size of the tumor.

In certain embodiments, the present invention provides a method of inhibiting the growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by the expression levels of tumor markers for that type of tumor.

In certain embodiments, the present invention provides a method of inhibiting the growth of prostate cancer. In particular embodiments, the present invention provides a method of inhibiting the growth of a castration-resistant prostate cancer.

Accordingly, the present invention also provides a method of treating a prostate cancer in a subject in need thereof, who is identified to respond to the treatment with SMARCA2/4 degraders, in need thereof, wherein the method comprises administering an effective amount of a SMARCA2/4 degrader to the subject.

In certain embodiments, methods are disclosed for the treatment of a prostate cancer or a castration-resistant prostate cancer.

Androgen receptor activity and gene expression profiling has been studied in prostate cancer. In seeking a biomarker, one begins with identifying an up-regulated gene and testing if this gene product can be a candidate biomarker. Gene expression profiling and linking the expression to mechanism of therapeutic resistance has been described by Holzbeierlein et al, Am. J. Path. 164(1), pp 217-227, 2004. While enhanced or reduced expression of certain genes have been identified, genomic alterations in certain genes may also occur in prostate cancer and these include: rearrangement (ETS transcription factors, RAF, KRAS); mutation (androgen receptor, PIK3CA, AKT, RAF, KRAS); amplification (androgen receptor, PIK3CA, MYC, AURKA); loss (PTEN, RBI). Other known tumor specific alterations occur in the SPOP, FOXA1, AURKA, MED 12, MAGI-1 and CHDI genes. ETS fusions can be found it upwards of 50% of PrCa and a targeted therapy or biomarker may be useful, for example targeting inhibition of PARP or DNAPK or analyzing patient samples for the ETS fusions. Oncogene expression, RAS/RAF, MYC, as well as the tumor suppressor gene RBI may be useful biomarkers.

Androgen receptor is known to regulate a large repertoire of genes central to the identity and behavior of prostate cancer cells. Overexpression of long non-coding RNA, for example PCGEM1 and PRNCR1, is associated and has been correlated with susceptibility of prostate cancer. Recently it was reported that both PCGEM1 and PRNCR1 are highly overexpressed in CRPC and they bind to and activate both ligand dependent and ligand independent AR-mediated gene activation programs and can lead to unchecked proliferation in prostate cancer cells. (Yang et al. Nature 2013, 500(7464): 598-602).

In certain embodiments, the present invention provides a method of treating a disease or disorder in a subject in need thereof; wherein the disease or disorder comprises at least one of the tumor specific alterations selected from:
 a) a mutation, an amplification, or an overexpression of Androgen Receptor (AR) gene;
 b) a loss of function or a deleterious mutation in phosphatase and tensin homolog (PTEN); and
 c) a genomic rearrangement that results in translocation between TMPRSS2 and ERG genes.

In certain embodiments, the subject is afflicted with prostate diseases.

In certain embodiments, the prostate disease is prostate cancer.

In certain embodiments, the prostate disease is a castration-resistant prostate cancer.

In certain embodiments, the subject has undergone castration.

In certain embodiments, the subject has undergone anti-androgen therapy.

Compounds Used in the Present Invention

In certain embodiments, the present invention provides a method of treating a disease or disorder in a subject in need thereof, who is identified to respond to the treatment according to the methods escribed herein comprising administering to the subject a therapeutically effective amount of a SMARCA2/4 degrader; wherein the SMARCA2/4 degrader is represented by compound of formula (I):

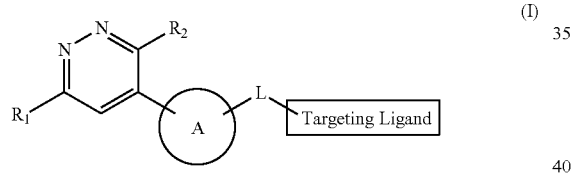

(I)

or a pharmaceutically acceptable salt thereof or a stereoisomer thereof;
wherein,
$R_1$ is hydrogen, halo, alkyl, alkenyl, alkoxy, hydroxy, hydroxyalkyl, —$COOR_a$, —$CON(R_a)_2$ or aryl; wherein, the aryl is optionally substituted with of at least one of hydroxy, alkoxy, halo, alkyl, amino, —ONa, —$COOR_a$ and —$OCOR_a$; wherein $R_a$ at each occurrence is selected from hydrogen and alkyl;
$R_2$ is —$NR_3R_4$ or —$OR_3$; wherein, $R_3$ and $R_4$ are independently selected from hydrogen and alkyl;
Ring A is heterocyclic ring optionally substituted with at least one of hydroxy, halo and alkyl;
L is a linker with a chemical structure of:

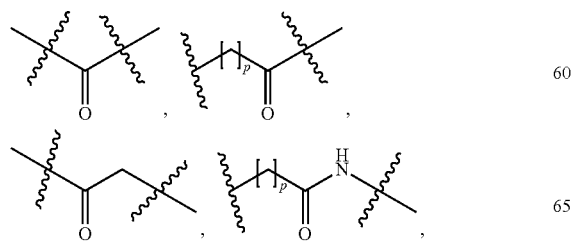

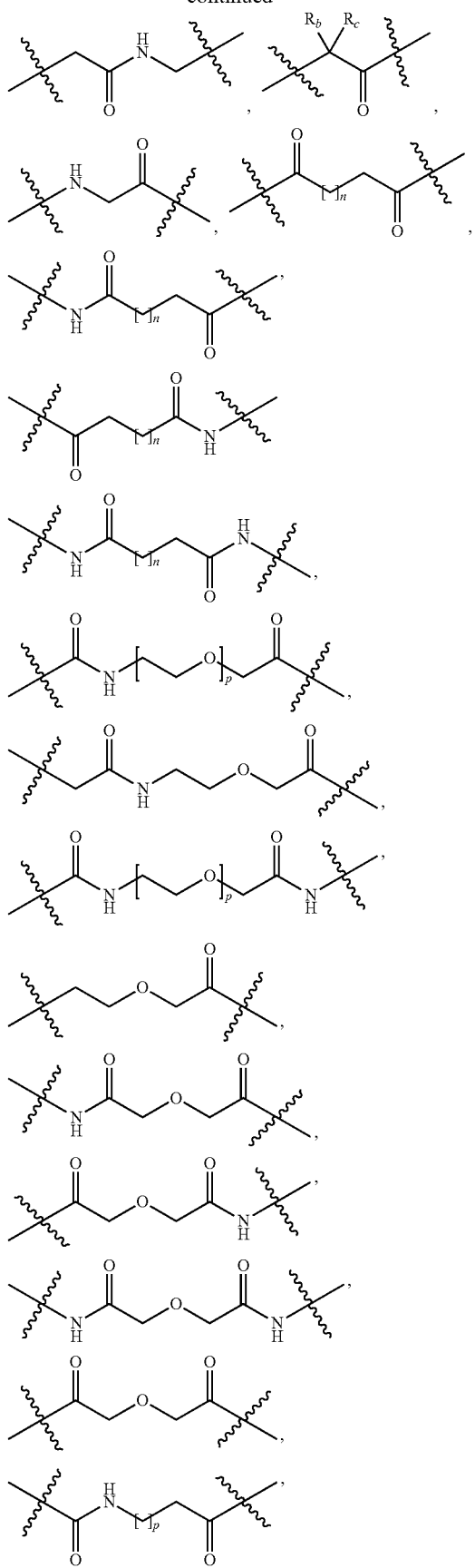

-continued

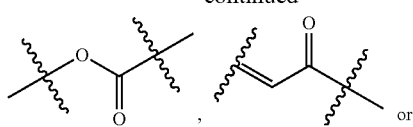

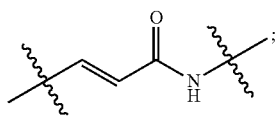

wherein, the left side of the linker is attached with ring A and the right side of the linker is attached with Targeting Ligand (TL);

$R_b$ is hydrogen or alkyl;

$R_c$ is alkyl;

'n' is 0 to 10 and 'p' is 1 to 5;

Targeting Ligand (TL) is

TL-1
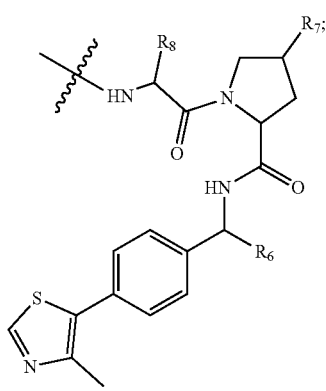

TL-2
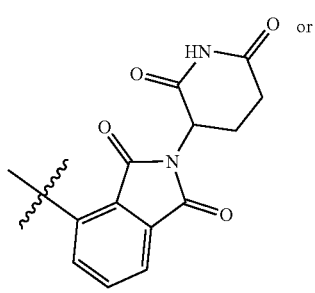

TL-3
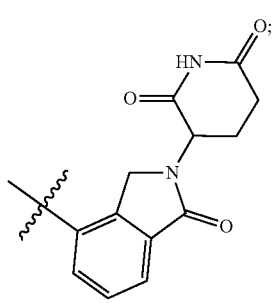

wherein, $R_6$ is selected from hydrogen, alkyl, acyl and haloalkyl;

$R_7$ is selected from —O—$R_5$ and halo; wherein $R_5$ is selected from hydrogen, alkyl, acyl and Na; and $R_8$ is hydrogen or alkyl.

In yet another embodiment of the present invention, it provides a method of treating a disease or disorder in a subject in need thereof, who is identified to respond to the treatment according to the methods described herein comprising administering to the subject a therapeutically effective amount of a SMARCA2/4 degrader; wherein the SMARCA2/4 degrader is represented by compounds of formula (IA):

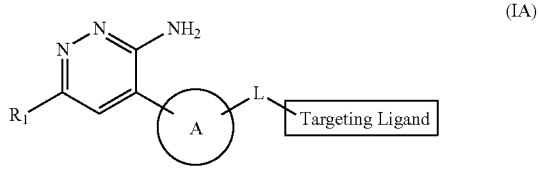

(IA)

or a pharmaceutically acceptable salt thereof or a stereoisomer thereof;

wherein, $R_1$, ring A, L and Targeting Ligand are same as defined in formula (I).

In yet another embodiment of the present invention, it provides a method of treating a disease or disorder in a subject in need thereof, who is identified to respond to the treatment according to the methods described herein comprising administering to the subject a therapeutically effective amount of a SMARCA2/4 degrader; wherein the SMARCA2/4 degrader is represented by compounds of formula (IB):

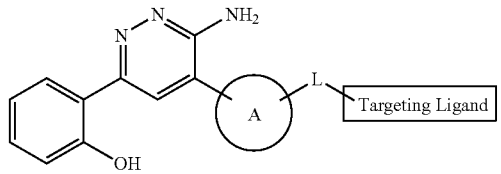

(IB)

or a pharmaceutically acceptable salt thereof or a stereoisomer thereof;

wherein, ring A, L and Targeting Ligand are same as defined in formula (I).

In yet another embodiment of the present invention, it provides a method of treating a disease or disorder in a subject in need thereof, who is identified to respond to the treatment according to the methods described herein comprising administering to the subject a therapeutically effective amount of a SMARCA2/4 degrader; wherein the SMARCA2/4 degrader is represented by compounds of formula (IC):

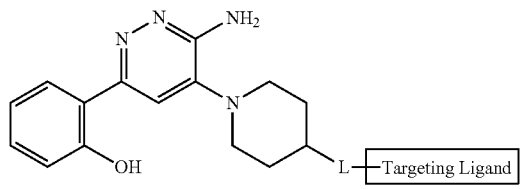

(IC)

or a pharmaceutically acceptable salt thereof or a stereoisomer thereof;

wherein, L and Targeting Ligand are same as defined in formula (I).

In yet another embodiment of the present invention, it provides a method of treating a disease or disorder in a subject in need thereof, who is identified to respond to the treatment according to the methods described herein comprising administering to the subject a therapeutically effective amount of a SMARCA2/4 degrader; wherein the SMARCA2/4 degrader is represented by compounds of formula (ID):

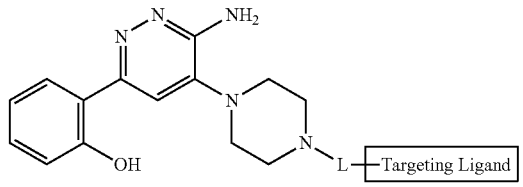

(ID)

or a pharmaceutically acceptable salt thereof or a stereoisomer thereof;

wherein, L and Targeting Ligand are same as defined in formula (I).

In certain embodiments of the methods disclosed herein, wherein the SMARCA2/4 degrader is a compound with the chemical structure of:

| Compound No | Structure |
|---|---|
| 1. | 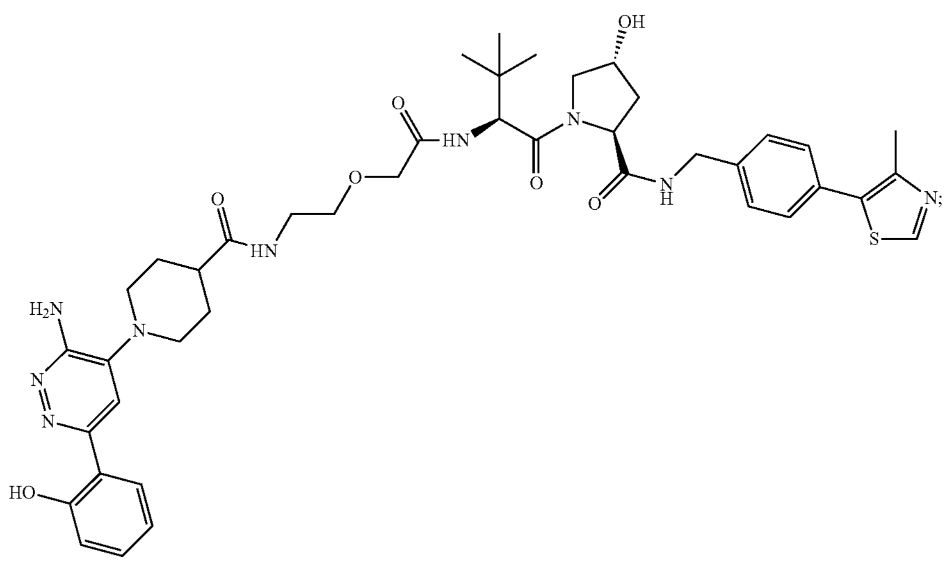 [SMILES: Cc1ncsc1-c1ccc(CNC(=O)[C@@H]2C[C@@H](O)CN2C(=O)[C@@H](NC(=O)COCCNC(=O)C2CCN(c3cc(-c4ccccc4O)nnc3N)CC2)C(C)(C)C)cc1] |
| 2. | 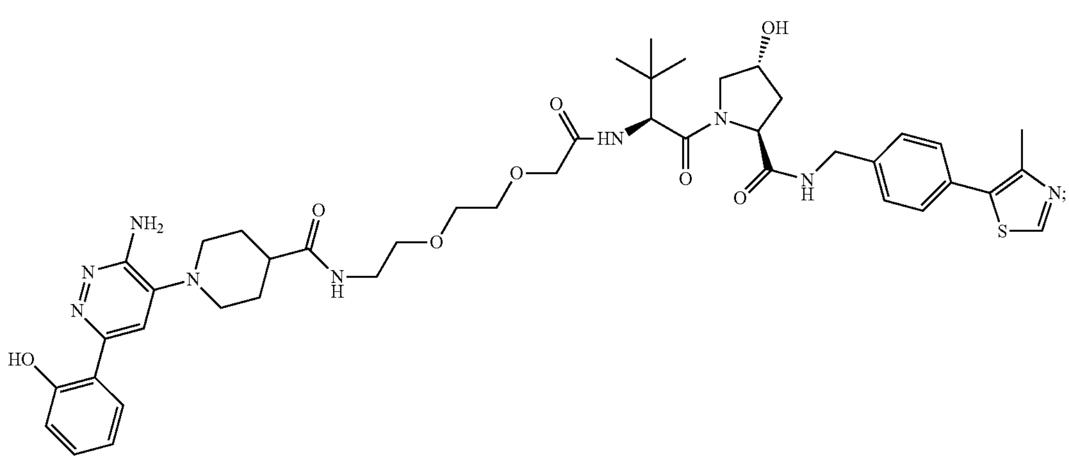 [SMILES: Cc1ncsc1-c1ccc(CNC(=O)[C@@H]2C[C@@H](O)CN2C(=O)[C@@H](NC(=O)COCCOCCNC(=O)C2CCN(c3cc(-c4ccccc4O)nnc3N)CC2)C(C)(C)C)cc1] |

-continued
| Compound No | Structure |
|---|---|
| 3. | 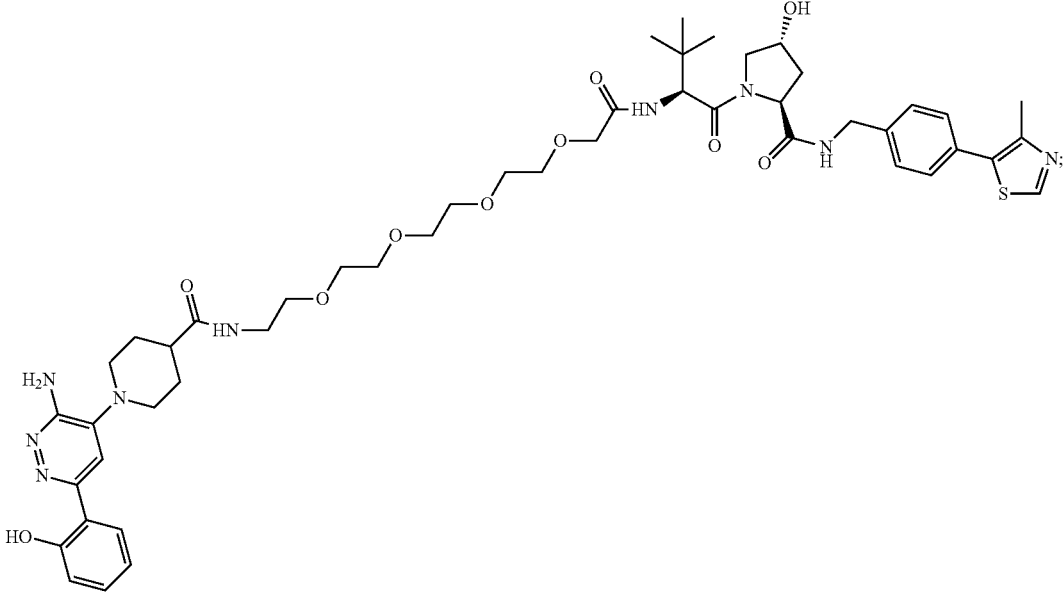 [SMILES: Cc1ncsc1-c1ccc(CNC(=O)[C@@H]2C[C@@H](O)CN2C(=O)[C@@H](NC(=O)COCCOCCOCCOCCNC(=O)C2CCN(c3cc(-c4ccccc4O)nnc3N)CC2)C(C)(C)C)cc1] |
| 4. | 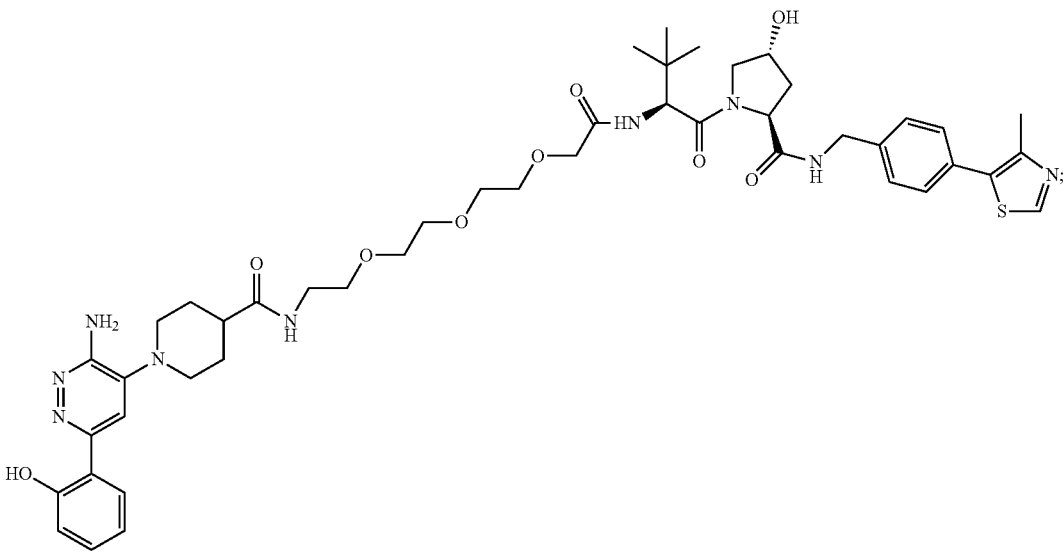 [SMILES: Cc1ncsc1-c1ccc(CNC(=O)[C@@H]2C[C@@H](O)CN2C(=O)[C@@H](NC(=O)COCCOCCOCCNC(=O)C2CCN(c3cc(-c4ccccc4O)nnc3N)CC2)C(C)(C)C)cc1] |
| 5. | 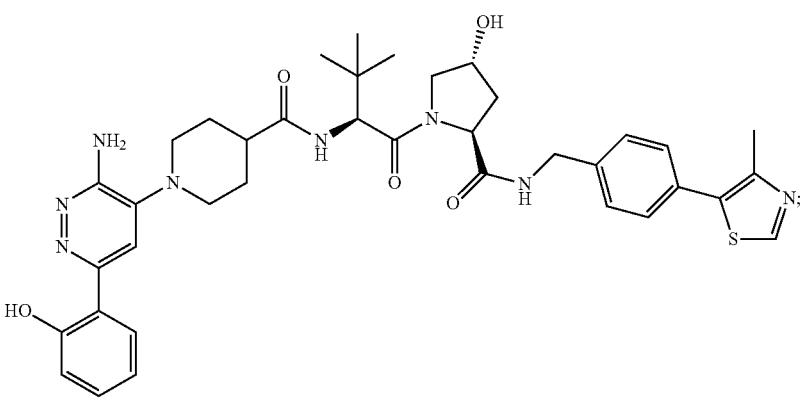 [SMILES: Cc1ncsc1-c1ccc(CNC(=O)[C@@H]2C[C@@H](O)CN2C(=O)[C@@H](NC(=O)C2CCN(c3cc(-c4ccccc4O)nnc3N)CC2)C(C)(C)C)cc1] |

-continued
| Compound No | Structure |
|---|---|
| 6. | 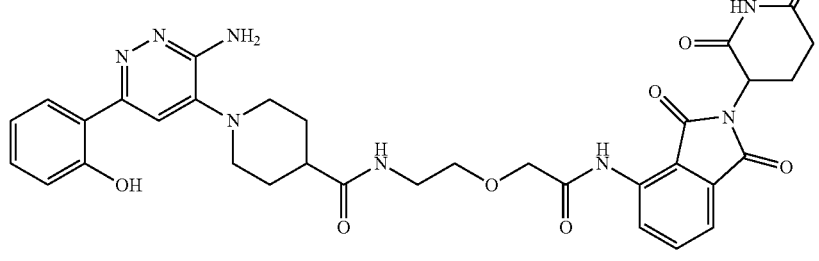 |
| 7. | 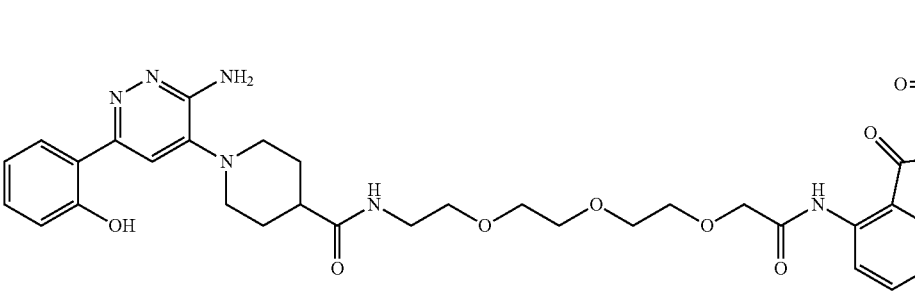 |
| 8. | 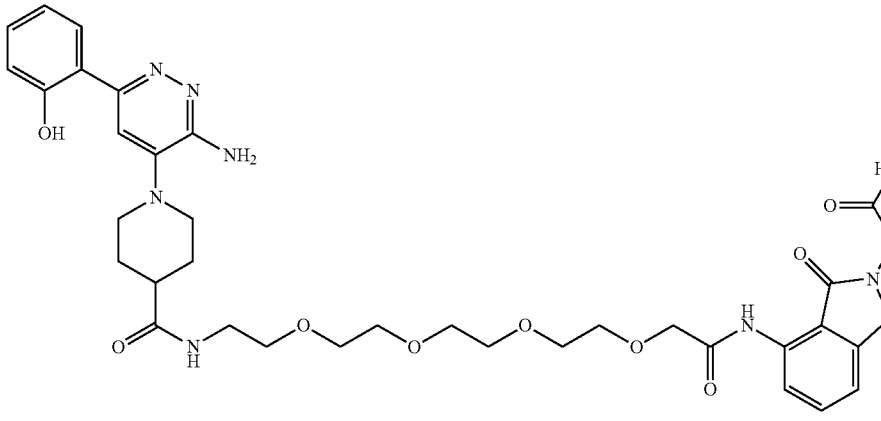 |
| 9. | 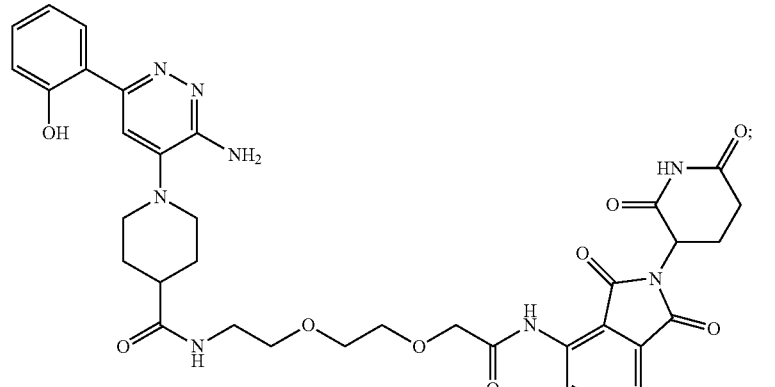 |

-continued
| Compound No | Structure |
|---|---|
| 10. | 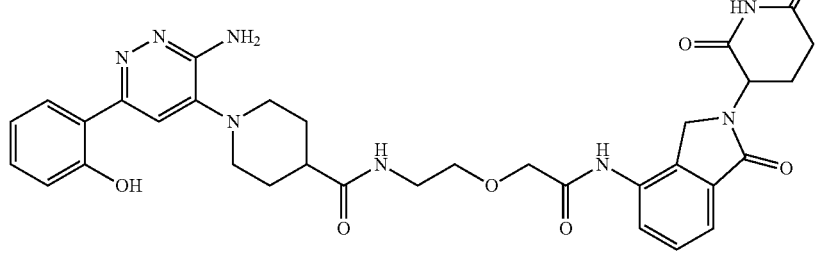 |
| 11. | 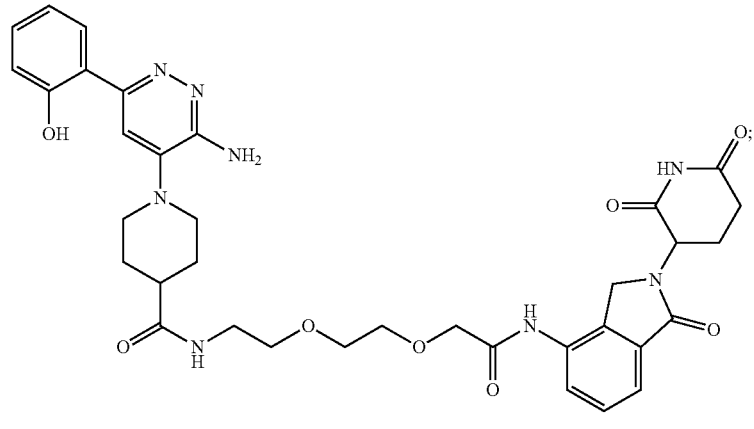 [SMILES: Nc1nnc(-c2ccccc2O)cc1N1CCC(C(=O)NCCOCCOCC(=O)Nc2cccc3c2CN(C2CCC(=O)NC2=O)C3=O)CC1] |
| 12. | 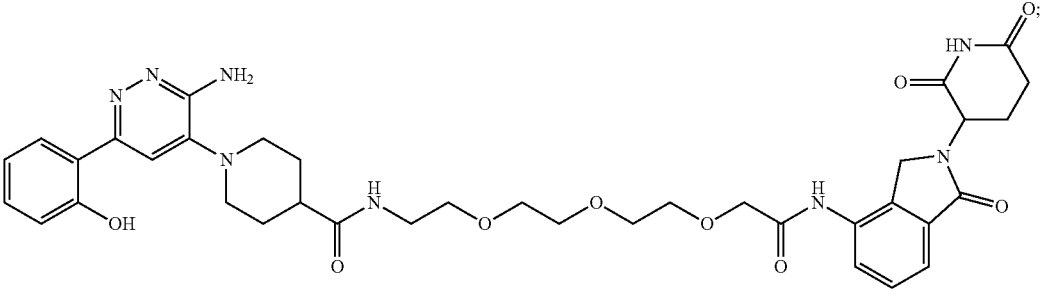 [SMILES: Nc1nnc(-c2ccccc2O)cc1N1CCC(C(=O)NCCOCCOCCOCC(=O)Nc2cccc3c2CN(C2CCC(=O)NC2=O)C3=O)CC1] |
| 13. | 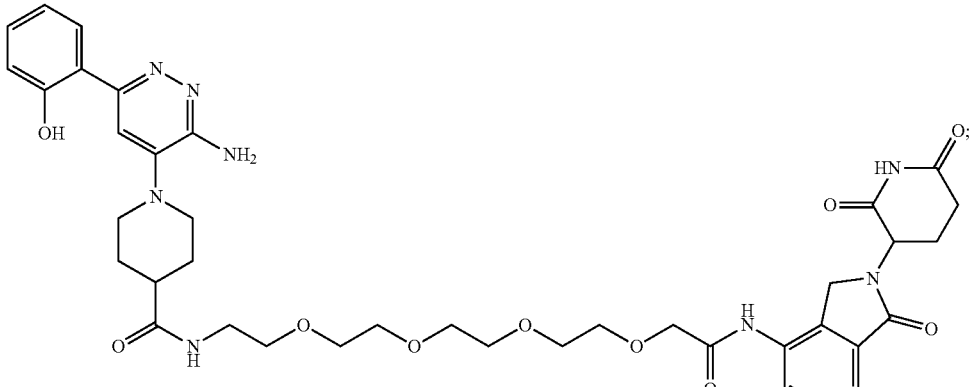 |

| Compound No | Structure |
|---|---|
| 14. | *(chemical structure)* |
| 15. | *(chemical structure)* |
| 16. | *(chemical structure)* |
| 17. | *(chemical structure)* |

-continued

| Compound No | Structure |
|---|---|
| 18. | 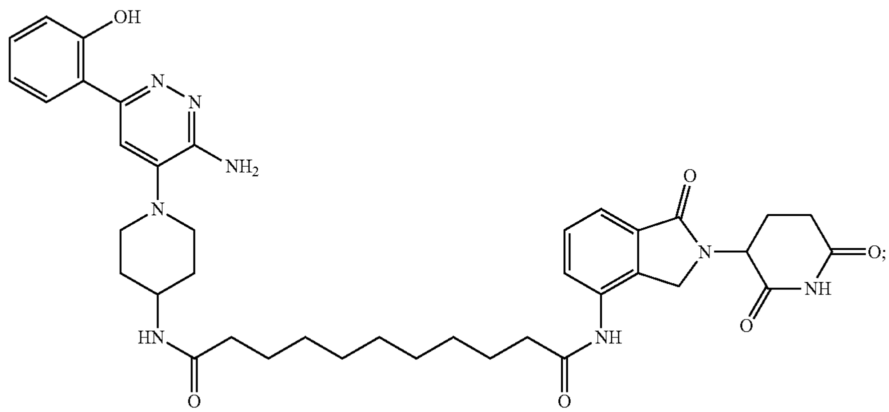 [SMILES: Nc1nnc(-c2ccccc2O)cc1N1CCC(NC(=O)CCCCCCCCCC(=O)Nc2cccc3c2CN(C2CCC(=O)NC2=O)C3=O)CC1] |
| 19. | 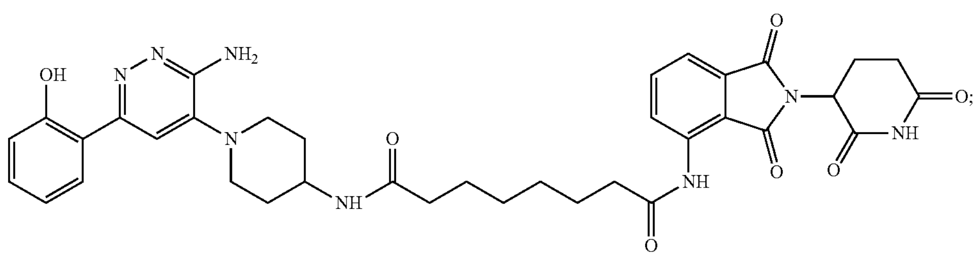 [SMILES: Nc1nnc(-c2ccccc2O)cc1N1CCC(NC(=O)CCCCCCC(=O)Nc2cccc3c2C(=O)N(C2CCC(=O)NC2=O)C3=O)CC1] |
| 20. | 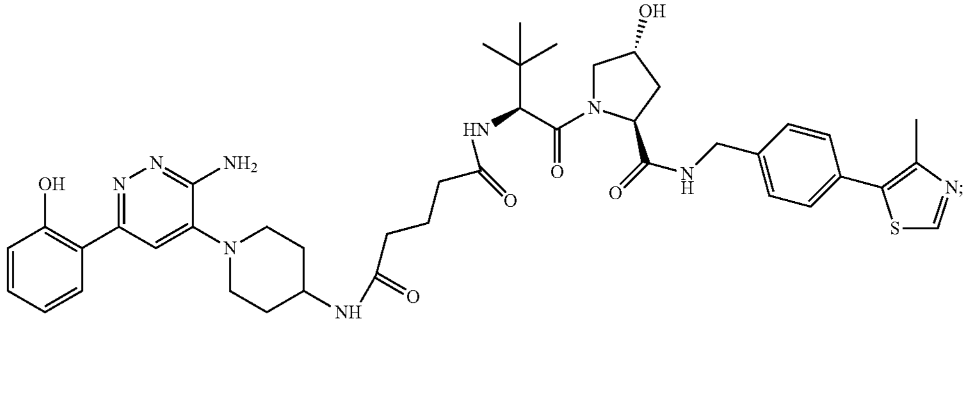 [SMILES: Cc1ncsc1-c1ccc(CNC(=O)[C@@H]2C[C@@H](O)CN2C(=O)[C@@H](NC(=O)CCCC(=O)NC2CCN(c3cc(-c4ccccc4O)nnc3N)CC2)C(C)(C)C)cc1] |

| Compound No | Structure |
|---|---|
| 21. | 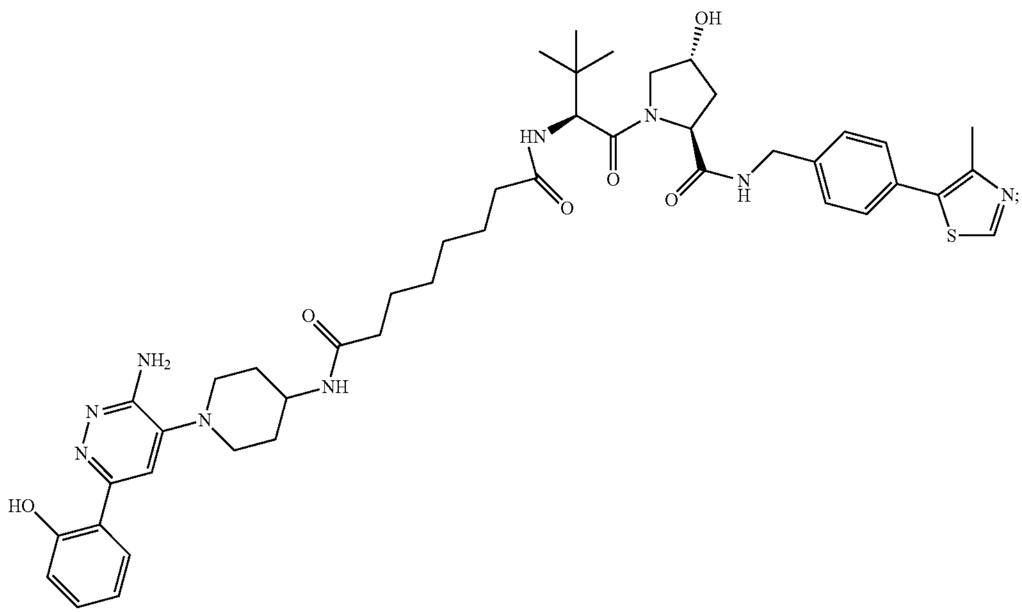 [SMILES: Cc1ncsc1-c1ccc(CNC(=O)[C@@H]2C[C@@H](O)CN2C(=O)[C@@H](NC(=O)CCCCCCC(=O)NC2CCN(c3cc(-c4ccccc4O)nnc3N)CC2)C(C)(C)C)cc1] |
| 22. | 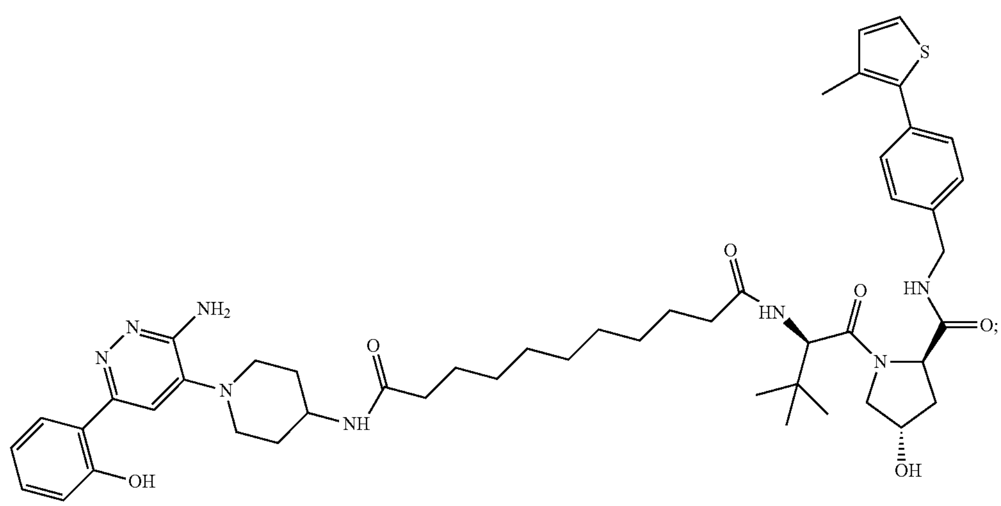 [SMILES: Cc1ccsc1-c1ccc(CNC(=O)[C@H]2C[C@H](O)CN2C(=O)[C@H](NC(=O)CCCCCCCCCC(=O)NC2CCN(c3cc(-c4ccccc4O)nnc3N)CC2)C(C)(C)C)cc1] |

| Compound No | Structure |
|---|---|
| 23. | 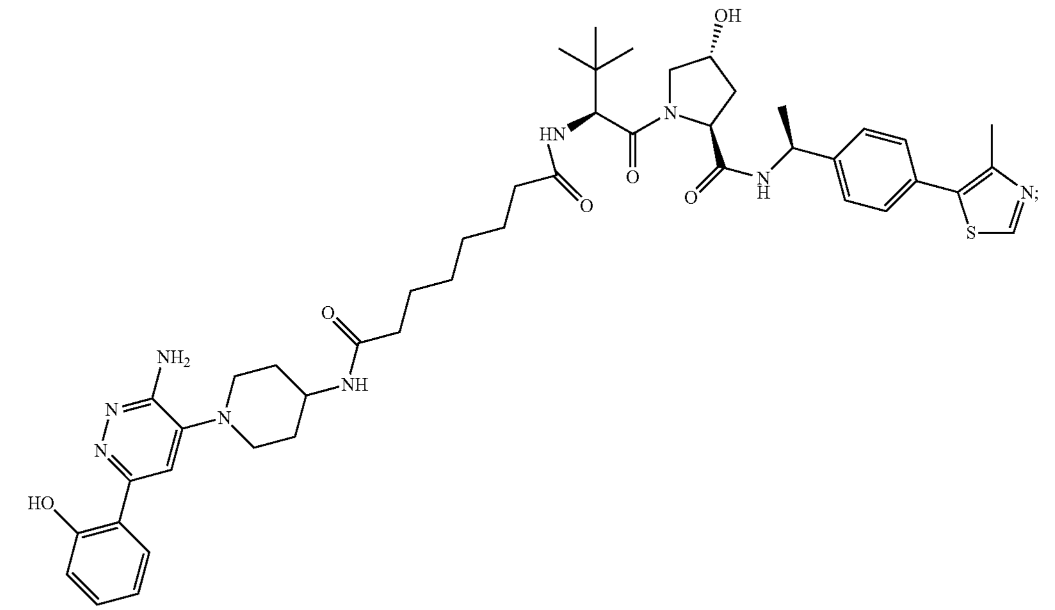 [SMILES: Cc1ncsc1-c1ccc([C@H](C)NC(=O)[C@@H]2C[C@@H](O)CN2C(=O)[C@@H](NC(=O)CCCCCCC(=O)NC2CCN(c3cc(-c4ccccc4O)nnc3N)CC2)C(C)(C)C)cc1] |
| 24. | 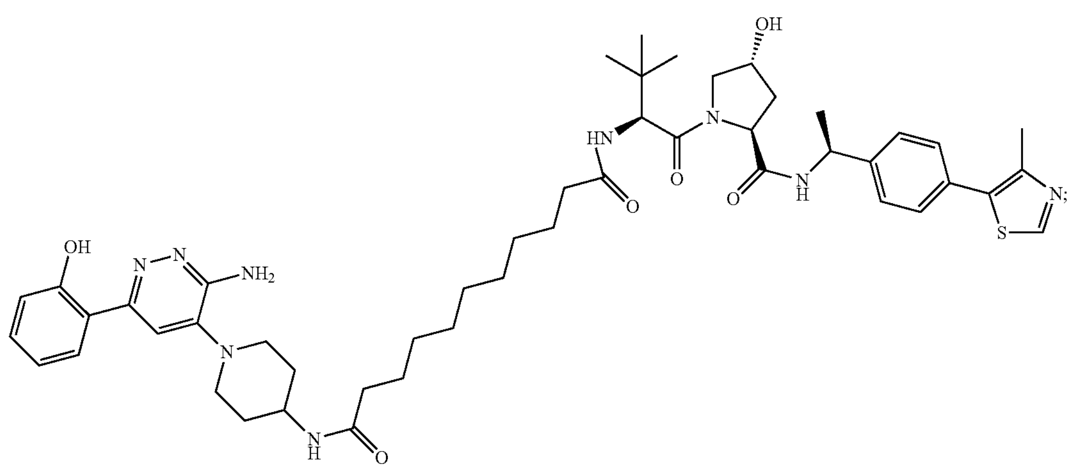 [SMILES: Cc1ncsc1-c1ccc([C@H](C)NC(=O)[C@@H]2C[C@@H](O)CN2C(=O)[C@@H](NC(=O)CCCCCCCCCC(=O)NC2CCN(c3cc(-c4ccccc4O)nnc3N)CC2)C(C)(C)C)cc1] |
| 25. | 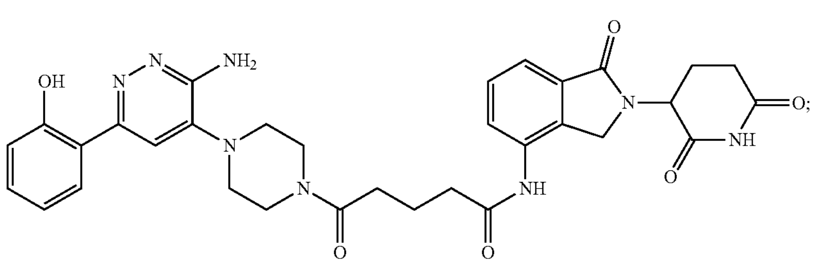 [SMILES: Nc1nnc(-c2ccccc2O)cc1N1CCN(C(=O)COCC(=O)Nc2cccc3c2CN(C2CCC(=O)NC2=O)C3=O)CC1] |

| Compound No | Structure |
|---|---|
| 26. | (chemical structure) |
| 27. | (chemical structure) |
| 28. | (chemical structure) |
| 29. | (chemical structure) |

| Compound No | Structure |
|---|---|
| 30. | 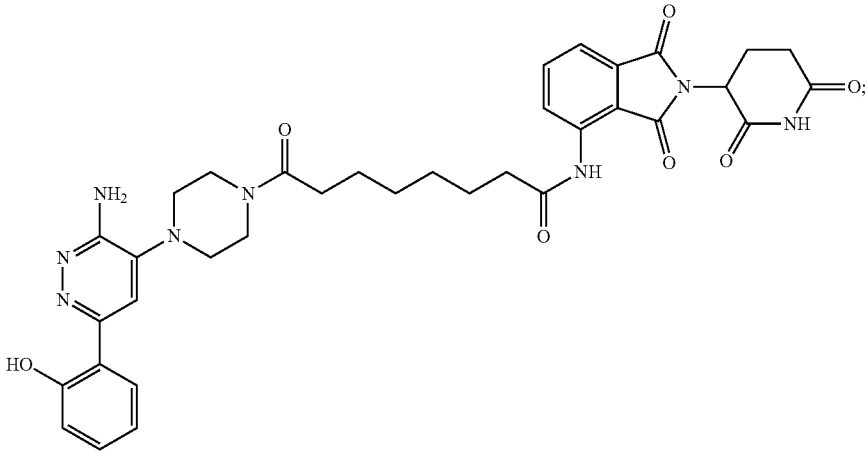 [SMILES: Nc1nnc(-c2ccccc2O)cc1N1CCN(C(=O)CCCCCCC(=O)Nc2cccc3c2C(=O)N(C2CCC(=O)NC2=O)C3=O)CC1] |
| 31. | 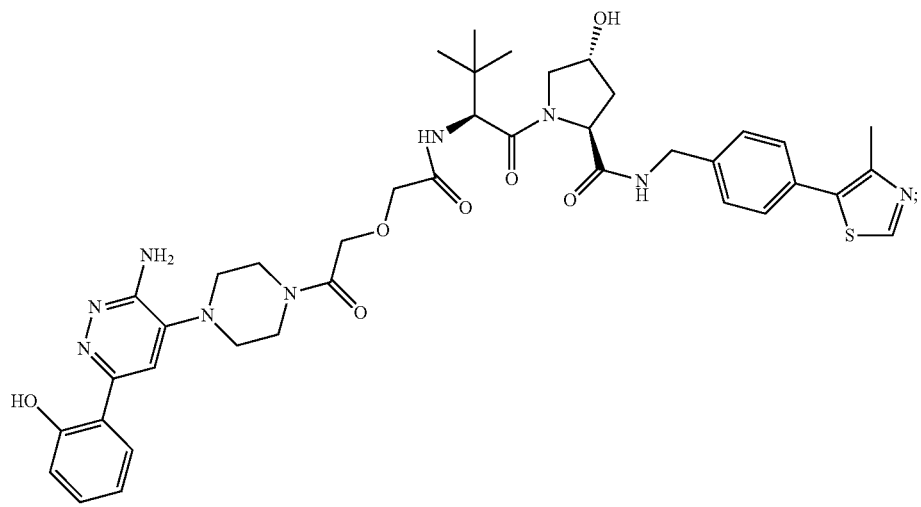 [SMILES: Cc1ncsc1-c1ccc(CNC(=O)[C@@H]2C[C@@H](O)CN2C(=O)[C@@H](NC(=O)COCC(=O)N2CCN(c3cc(-c4ccccc4O)nnc3N)CC2)C(C)(C)C)cc1] |
| 32. | 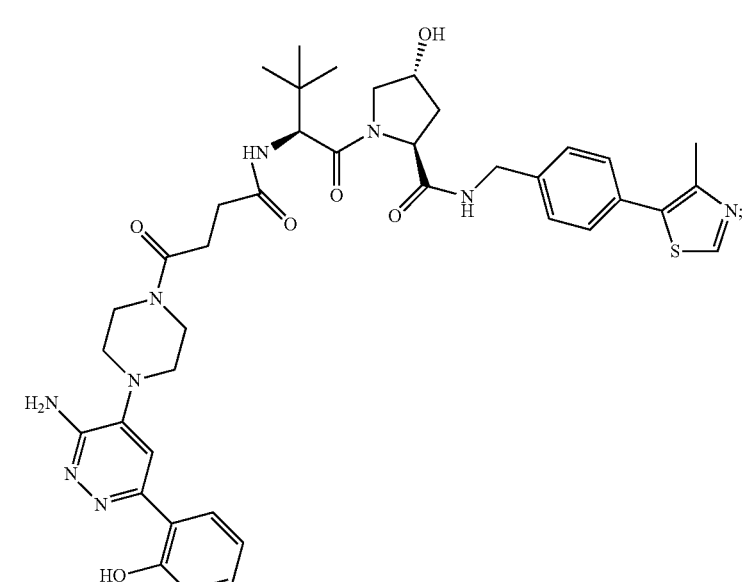 |

| Compound No | Structure |
|---|---|
| 33. | 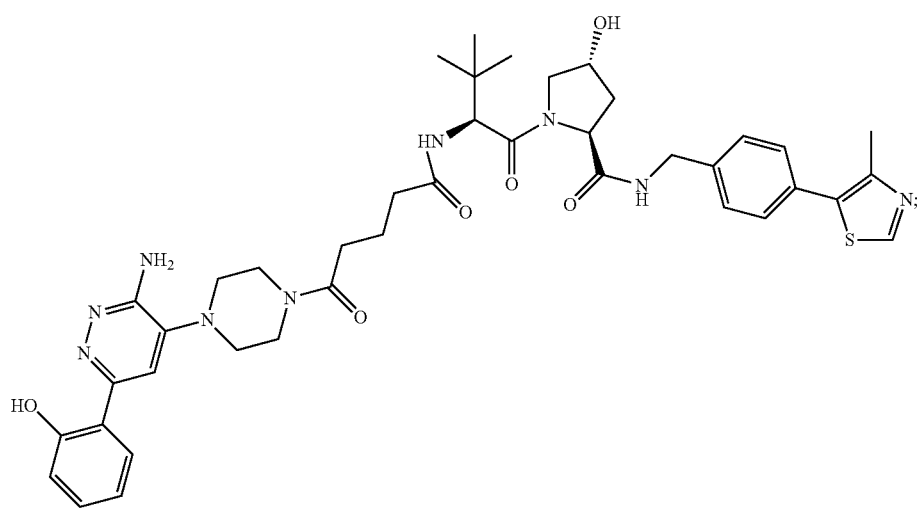 [SMILES: Cc1ncsc1-c1ccc(CNC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] |
| 34. | 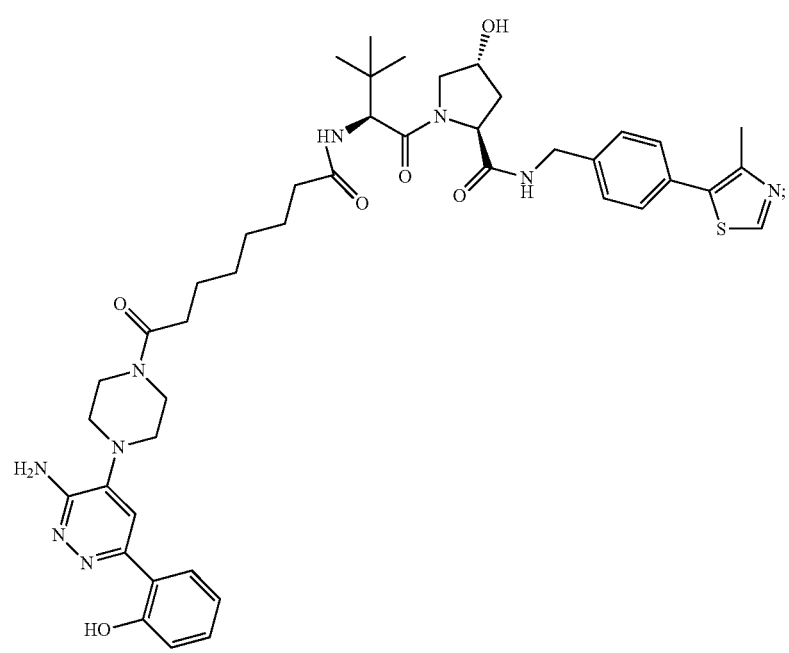 [SMILES: Cc1ncsc1-c1ccc(CNC(=O)[C@@H]2C[C@@H](O)CN2C(=O)[C@@H](NC(=O)CCCCCCC(=O)N2CCN(c3cc(-c4ccccc4O)nnc3N)CC2)C(C)(C)C)cc1] |

| Compound No | Structure |
|---|---|
| 35. | 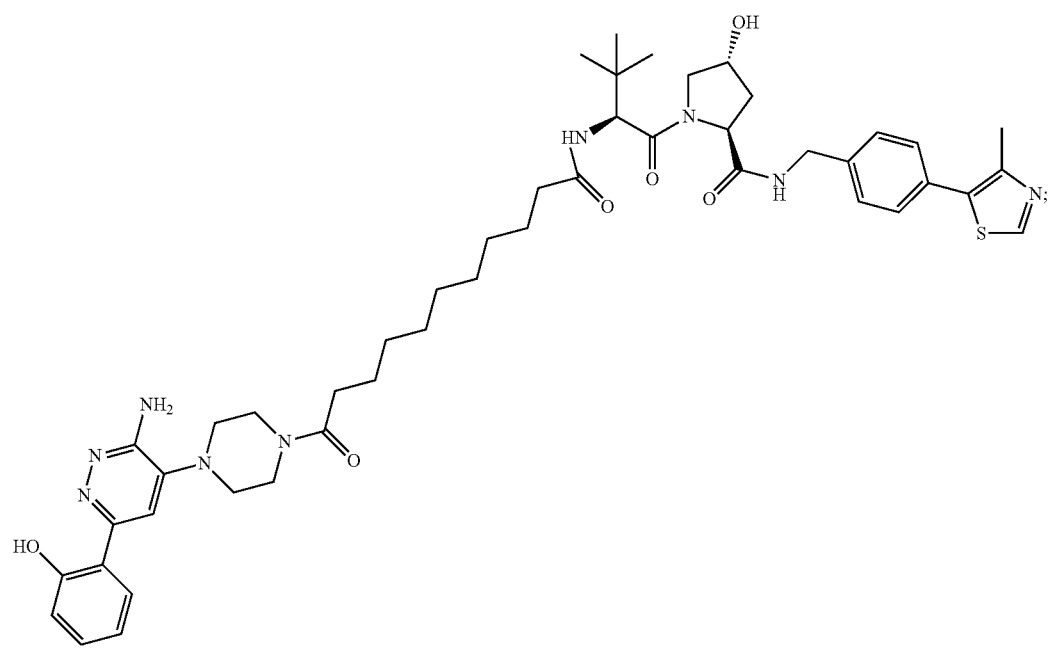 [SMILES: Cc1ncsc1-c1ccc(CNC(=O)[C@@H]2C[C@@H](O)CN2C(=O)[C@@H](NC(=O)CCCCCCCCCC(=O)N2CCN(c3cc(-c4ccccc4O)nnc3N)CC2)C(C)(C)C)cc1] |
| 36. | 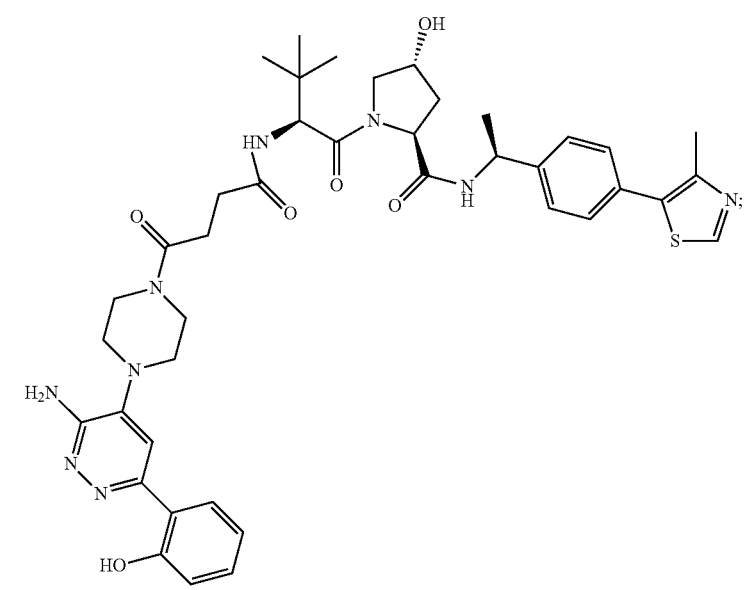 [SMILES: Cc1ncsc1-c1ccc([C@H](C)NC(=O)[C@@H]2C[C@@H](O)CN2C(=O)[C@@H](NC(=O)CCC(=O)N2CCN(c3cc(-c4ccccc4O)nnc3N)CC2)C(C)(C)C)cc1] |

-continued
| Compound No | Structure |
|---|---|
| 37. | 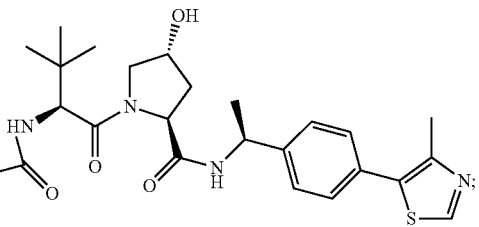 |
| 38. | 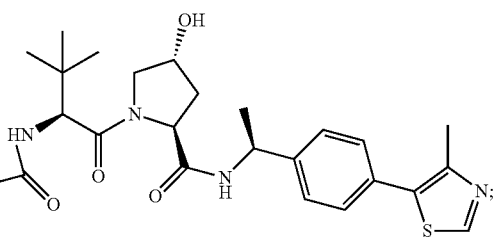 |
| 39. | 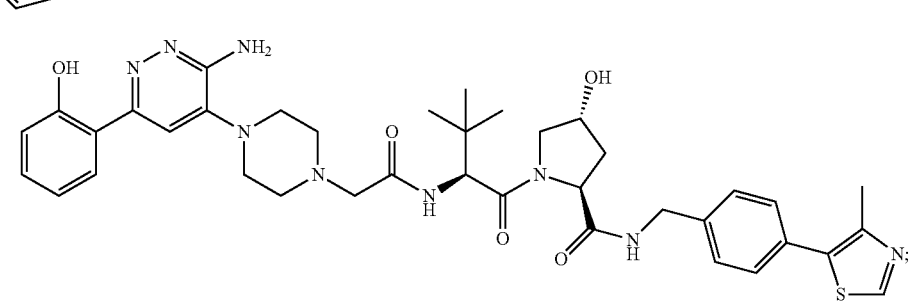 |

| Compound No | Structure |
|---|---|
| 40. | 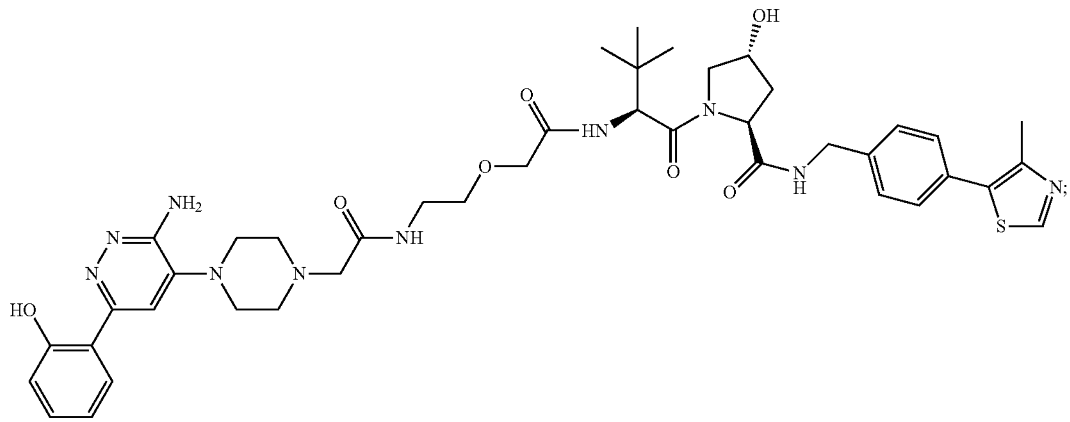 [SMILES: Cc1ncsc1-c1ccc(CNC(=O)[C@@H]2C[C@@H](O)CN2C(=O)[C@@H](NC(=O)COCCNC(=O)CN2CCN(c3cc(-c4ccccc4O)nnc3N)CC2)C(C)(C)C)cc1] |
| 41. | 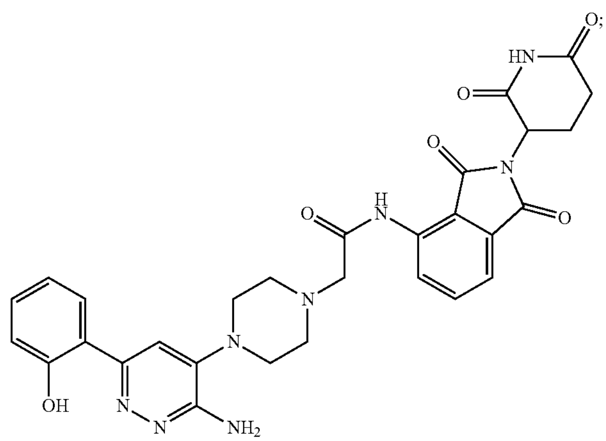 [SMILES: Nc1nnc(-c2ccccc2O)cc1N1CCN(CC(=O)Nc2cccc3c2C(=O)N(C2CCC(=O)NC2=O)C3=O)CC1] |
| 42. | 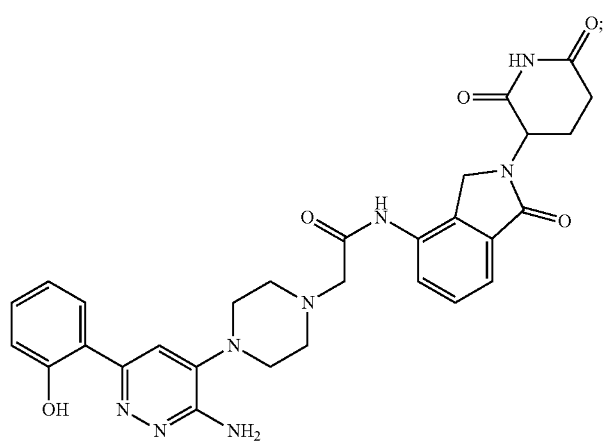 [SMILES: Nc1nnc(-c2ccccc2O)cc1N1CCN(CC(=O)Nc2cccc3c2CN(C2CCC(=O)NC2=O)C3=O)CC1] |
| 43. | 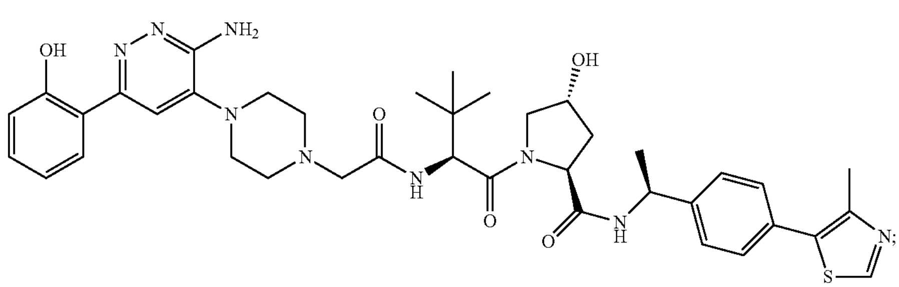 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)(C)C)cc1] |

| Compound No | Structure |
|---|---|
| 44. | 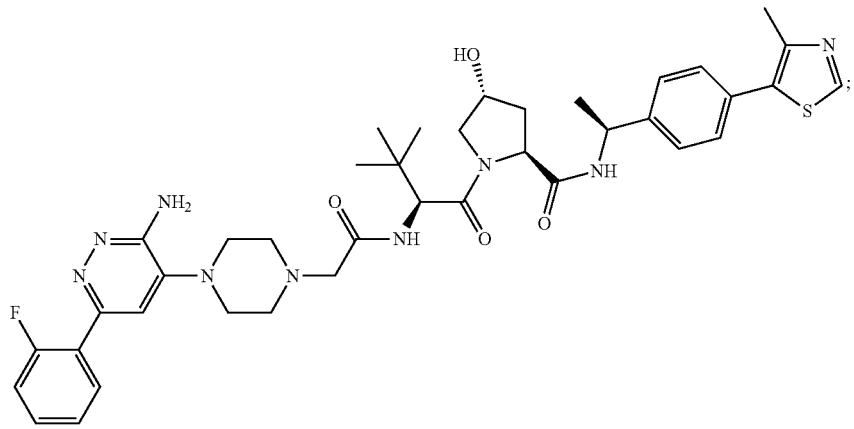 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4F)nnc3N)CC2)C(C)(C)C)cc1 ; ";"] |
| 45. | 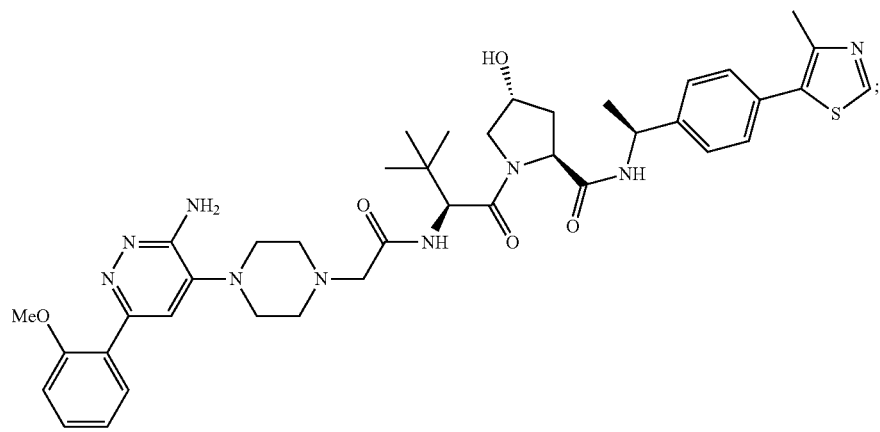 [SMILES: COc1ccccc1-c1cc(N2CCN(CC(=O)N[C@H](C(=O)N3C[C@H](O)C[C@H]3C(=O)N[C@@H](C)c3ccc(-c4scnc4C)cc3)C(C)(C)C)CC2)c(N)nn1 ; ";"] |
| 46. | 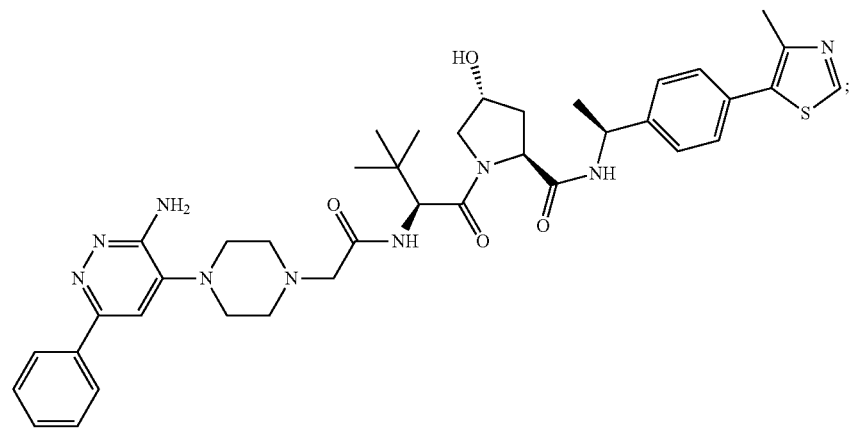 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4)nnc3N)CC2)C(C)(C)C)cc1 ; ";"] |

-continued

| Compound No | Structure |
|---|---|
| 47. | 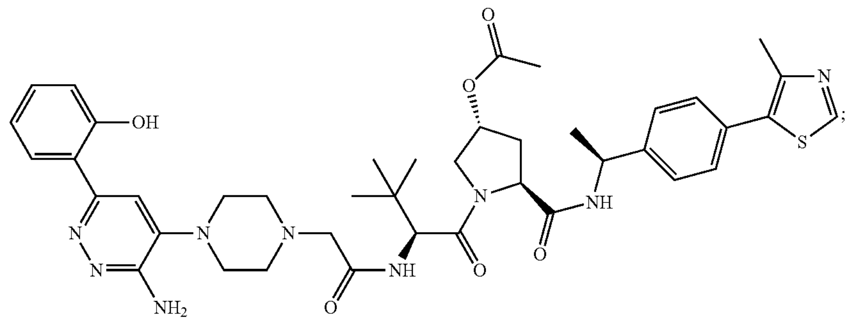 [SMILES: CC(=O)O[C@@H]1C[C@@H](C(=O)N[C@@H](C)c2ccc(-c3scnc3C)cc2)N(C(=O)[C@@H](NC(=O)CN2CCN(c3cc(-c4ccccc4O)nnc3N)CC2)C(C)(C)C)C1 ; ";"] |
| 48. | 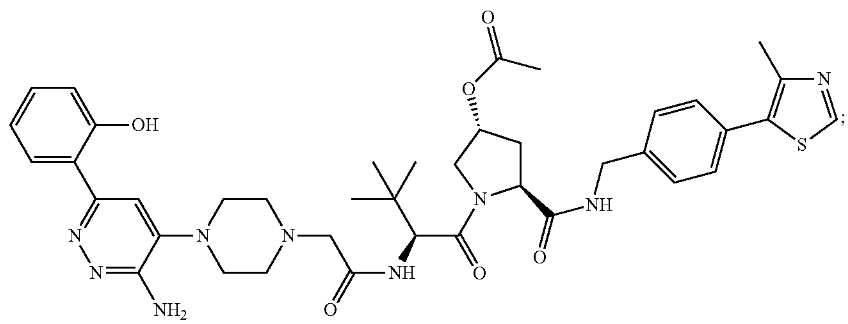 [SMILES: CC(=O)O[C@@H]1C[C@@H](C(=O)NCc2ccc(-c3scnc3C)cc2)N(C(=O)[C@@H](NC(=O)CN2CCN(c3cc(-c4ccccc4O)nnc3N)CC2)C(C)(C)C)C1 ; ";"] |
| 49. | 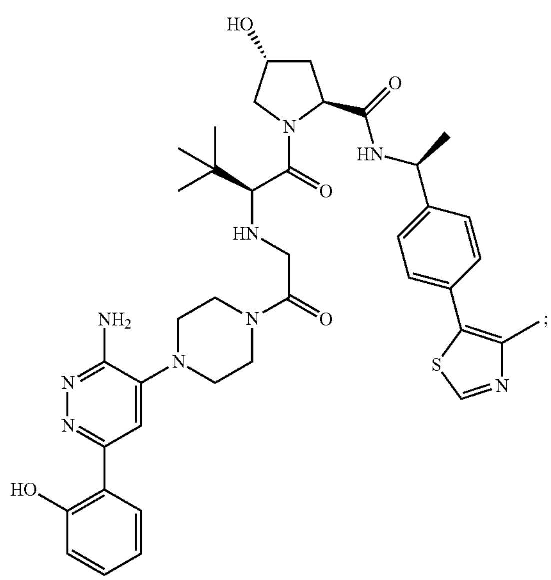 [SMILES: Cc1ncsc1-c1ccc([C@H](C)NC(=O)[C@@H]2C[C@@H](O)CN2C(=O)[C@@H](NCC(=O)N2CCN(c3cc(-c4ccccc4O)nnc3N)CC2)C(C)(C)C)cc1 ; ";"] |

| Compound No | Structure |
|---|---|
| 50. | (chemical structure) |
| 51. | (chemical structure) |
| 52. | (chemical structure) |

-continued
| Compound No | Structure |
|---|---|
| 53. | 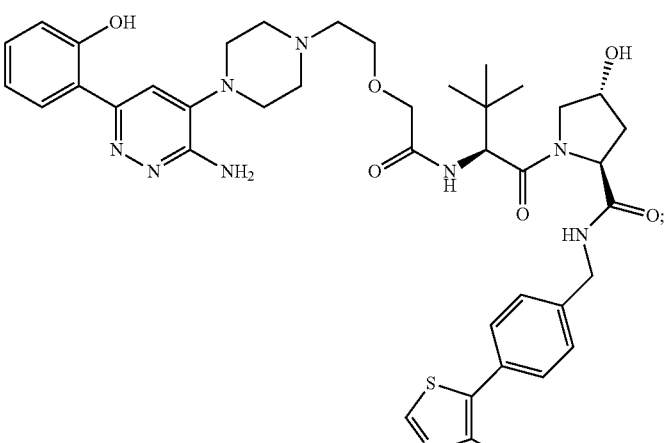 |
| 54. | 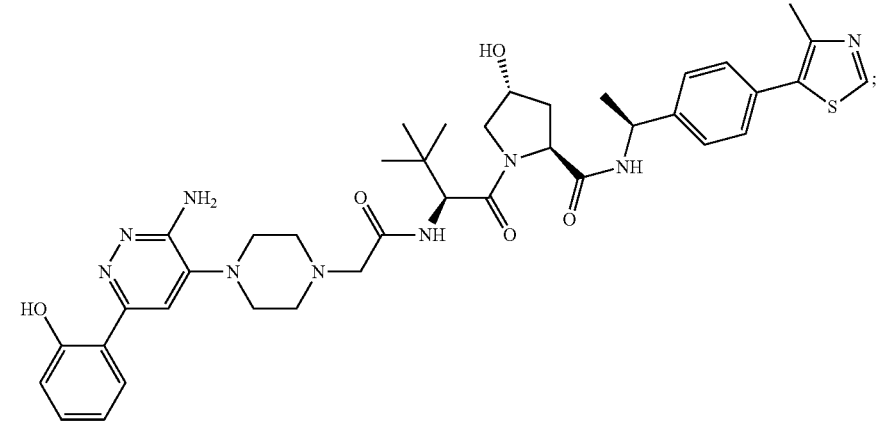 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)(C)C)cc1 ; ";"] |
| 55. | 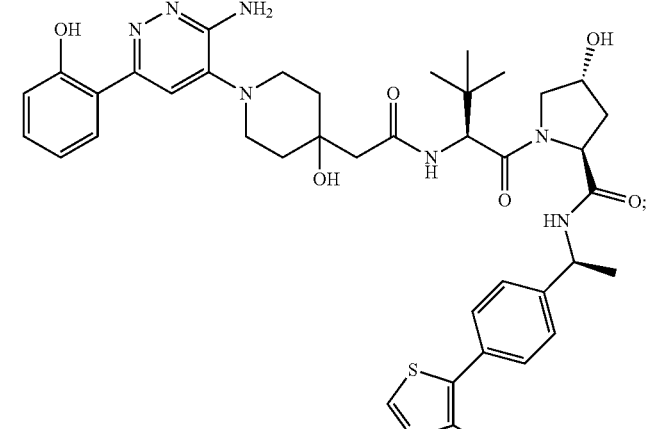 |

| Compound No | Structure |
|---|---|
| 56. | 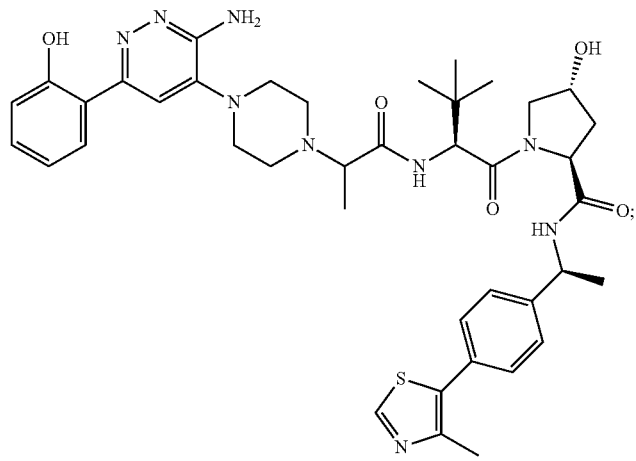 |
| 57. and 58. | 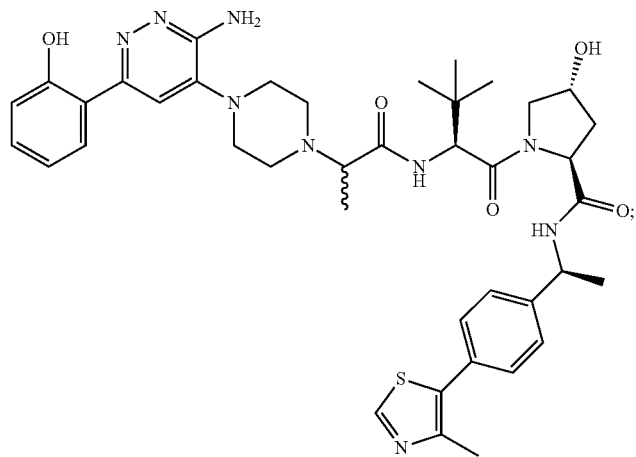 [SMILES: Cc1ncsc1-c1ccc([C@H](C)NC(=O)[C@@H]2C[C@@H](O)CN2C(=O)[C@@H](NC(=O)C(C)N2CCN(c3cc(-c4ccccc4O)nnc3N)CC2)C(C)(C)C)cc1]
Isomer-1 and Isomer-2 |
| 59. | 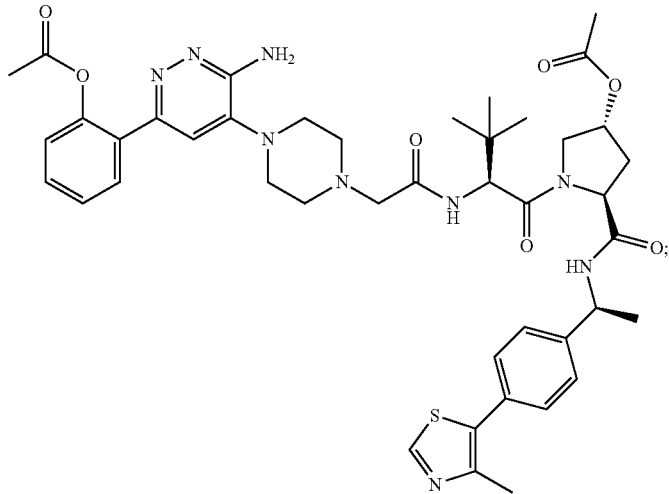 [SMILES: CC(=O)Oc1ccccc1-c1cc(N2CCN(CC(=O)N[C@H](C(=O)N3C[C@H](OC(C)=O)C[C@H]3C(=O)N[C@@H](C)c3ccc(-c4scnc4C)cc3)C(C)(C)C)CC2)c(N)nn1] |

| Compound No | Structure |
|---|---|
| 60. | 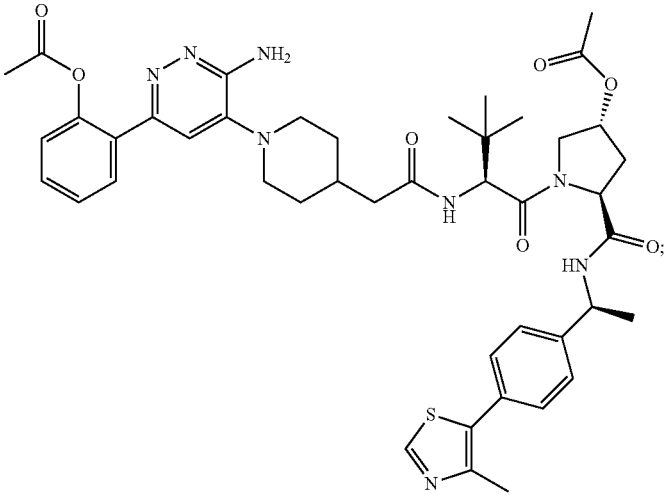 [SMILES: CC(=O)Oc1ccccc1-c1cc(N2CCC(CC(=O)N[C@H](C(=O)N3C[C@H](OC(C)=O)C[C@H]3C(=O)N[C@@H](C)c3ccc(-c4scnc4C)cc3)C(C)(C)C)CC2)c(N)nn1] |
| 61. | 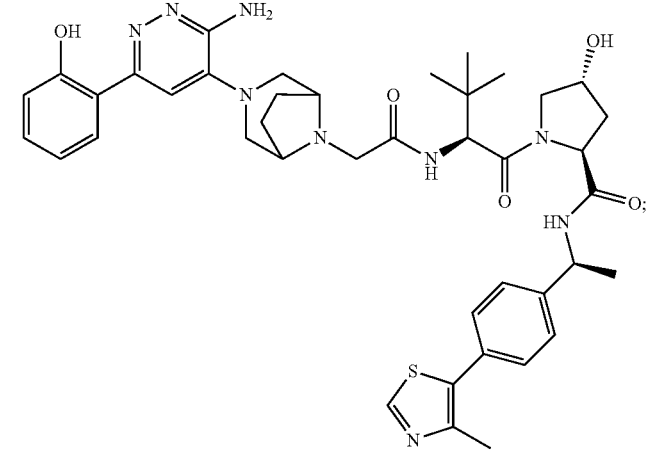 [SMILES: Cc1ncsc1-c1ccc([C@H](C)NC(=O)[C@@H]2C[C@@H](O)CN2C(=O)[C@@H](NC(=O)CN2C3CCC2CN(c2cc(-c4ccccc4O)nnc2N)C3)C(C)(C)C)cc1] |
| 62. | 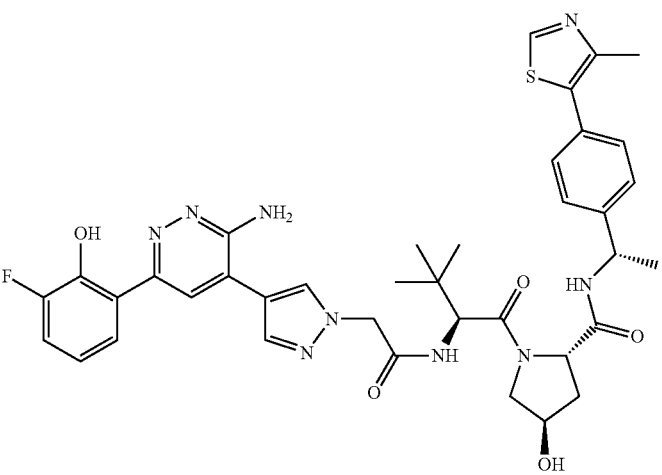 |

| Compound No | Structure |
|---|---|
| 63. | (structure) |
| 64. | (structure) |
| 65. | (structure) |

| Compound No | Structure |
|---|---|
| 66. | 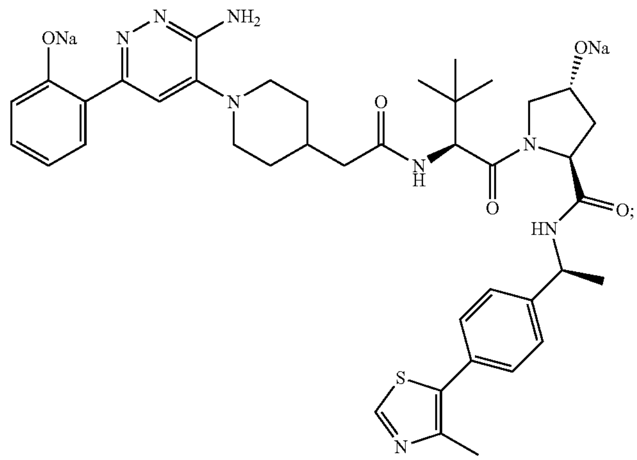 |
| 67. | 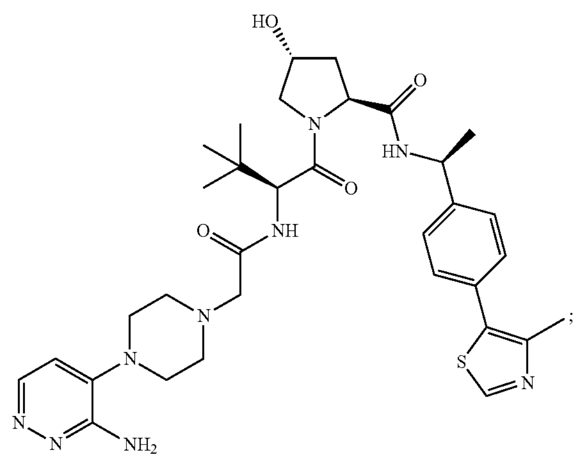 |
| 68. | 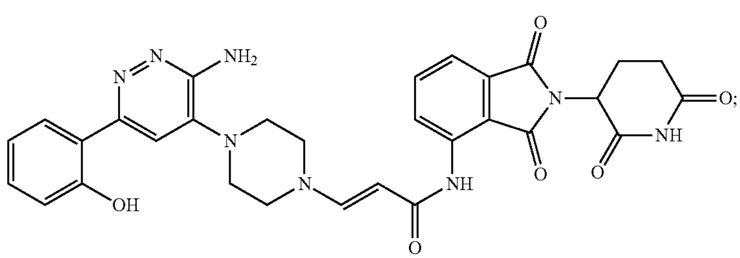 [SMILES: Nc1nnc(-c2ccccc2O)cc1N1CCN(/C=C/C(=O)Nc2cccc3c2C(=O)N(C2CCC(=O)NC2=O)C3=O)CC1] |
| 69. | 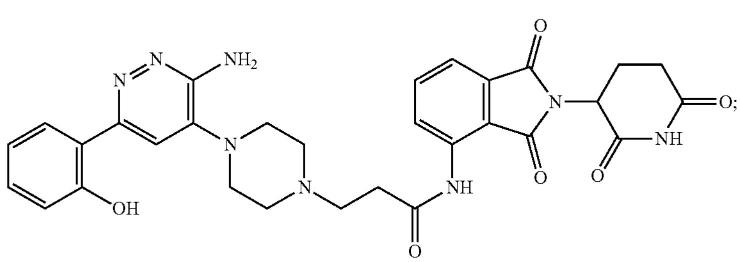 [SMILES: Nc1nnc(-c2ccccc2O)cc1N1CCN(CCC(=O)Nc2cccc3c2C(=O)N(C2CCC(=O)NC2=O)C3=O)CC1] |

| Compound No | Structure |
|---|---|
| 70. | 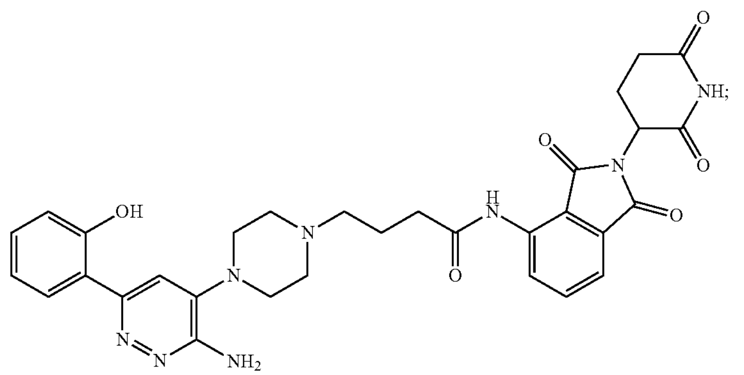 [SMILES: Nc1nnc(-c2ccccc2O)cc1N1CCN(CCCC(=O)Nc2cccc3c2C(=O)N(C2CCC(=O)NC2=O)C3=O)CC1] |
| 71. | 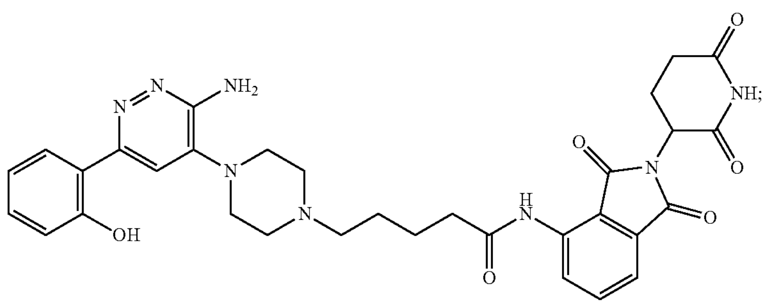 [SMILES: Nc1nnc(-c2ccccc2O)cc1N1CCN(CCCCC(=O)Nc2cccc3c2C(=O)N(C2CCC(=O)NC2=O)C3=O)CC1] |
| 72. | 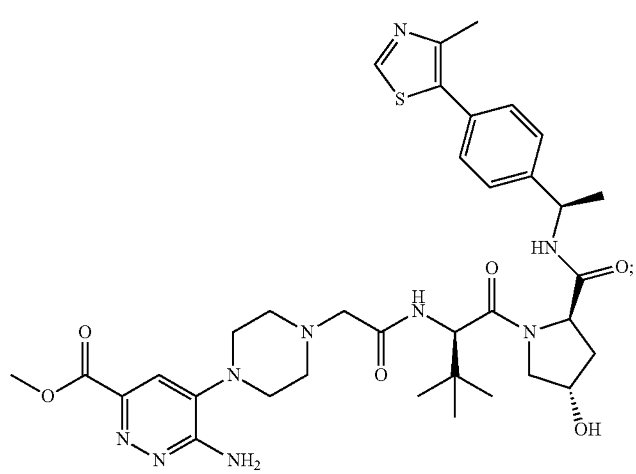 [SMILES: COC(=O)c1cc(N2CCN(CC(=O)N[C@@H](C(=O)N3C[C@@H](O)C[C@@H]3C(=O)N[C@H](C)c3ccc(-c4scnc4C)cc3)C(C)(C)C)CC2)c(N)nn1] |

| Compound No | Structure |
|---|---|
| 73. | 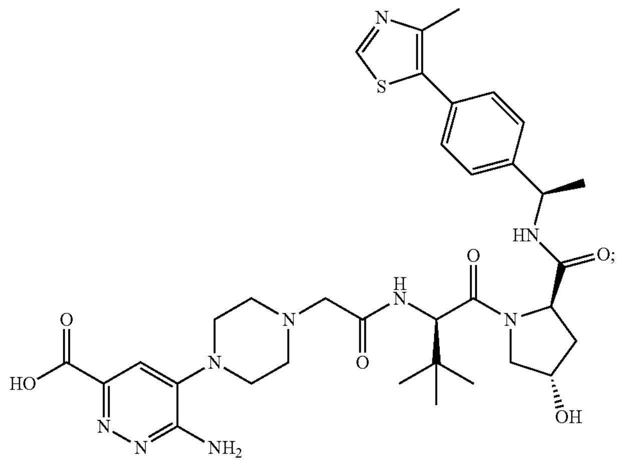 [SMILES: Cc1ncsc1-c1ccc([C@@H](C)NC(=O)[C@H]2C[C@H](O)CN2C(=O)[C@H](NC(=O)CN2CCN(c3cc(C(=O)O)nnc3N)CC2)C(C)(C)C)cc1] |
| 74. | 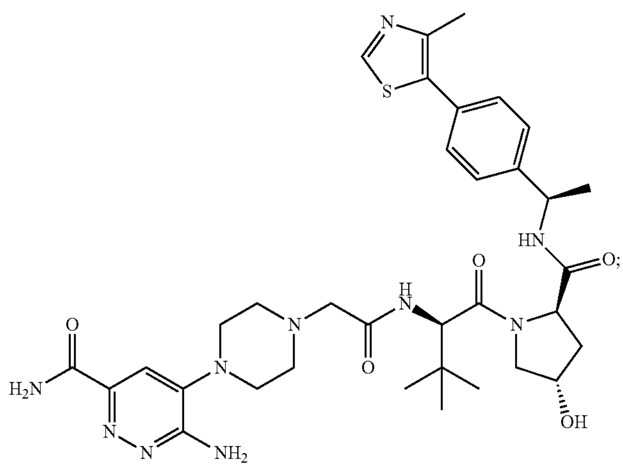 [SMILES: Cc1ncsc1-c1ccc([C@@H](C)NC(=O)[C@H]2C[C@H](O)CN2C(=O)[C@H](NC(=O)CN2CCN(c3cc(C(N)=O)nnc3N)CC2)C(C)(C)C)cc1] |
| 75. | 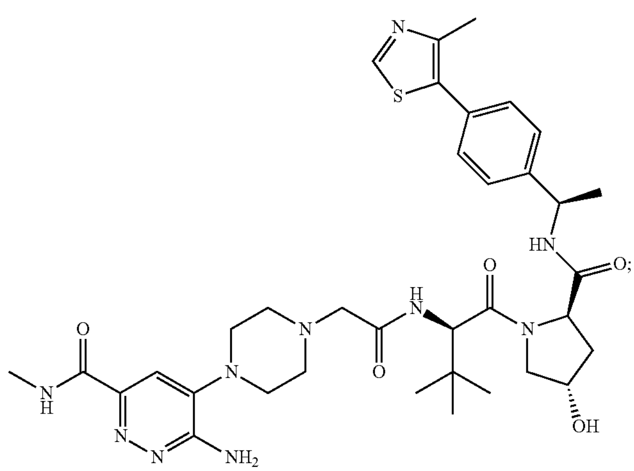 [SMILES: CNC(=O)c1cc(N2CCN(CC(=O)N[C@@H](C(=O)N3C[C@@H](O)C[C@@H]3C(=O)N[C@H](C)c3ccc(-c4scnc4C)cc3)C(C)(C)C)CC2)c(N)nn1] |

| Compound No | Structure |
|---|---|
| 76. | 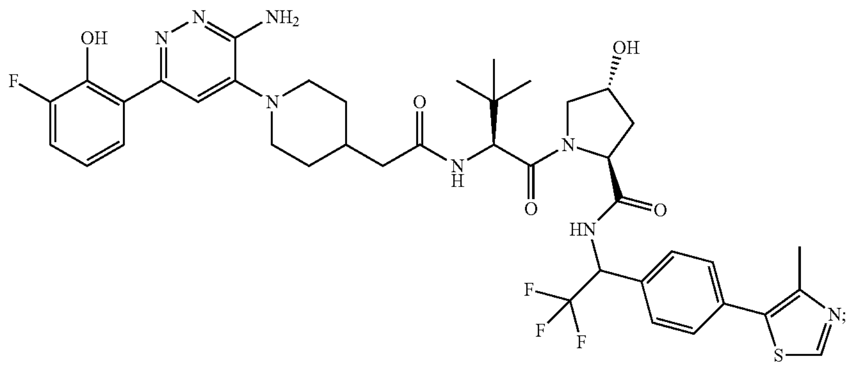 [SMILES: Cc1ncsc1-c1ccc(C(NC(=O)[C@@H]2C[C@@H](O)CN2C(=O)[C@@H](NC(=O)CC2CCN(c3cc(-c4cccc(F)c4O)nnc3N)CC2)C(C)(C)C)C(F)(F)F)cc1] |
| 77. and 78. | Isomer-1 and Isomer-2 |
| 79. | 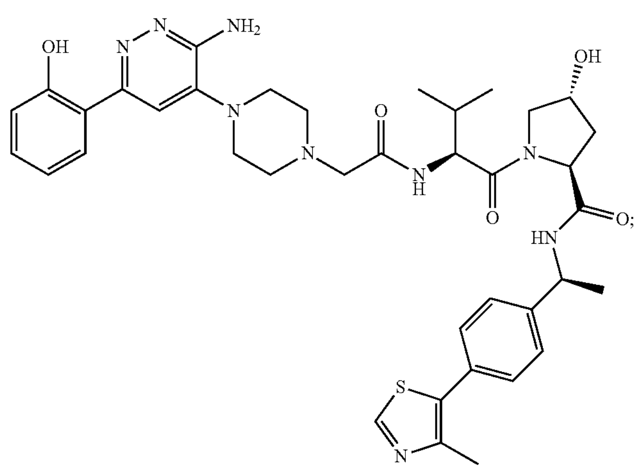 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)C)cc1] |

| Compound No | Structure |
|---|---|
| 80. | 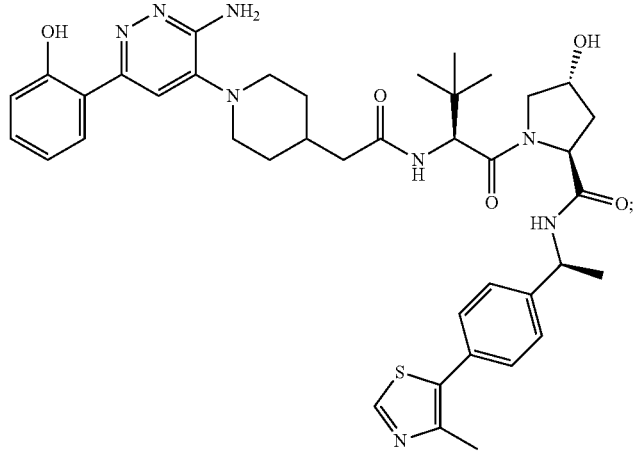 [SMILES: Cc1ncsc1-c1ccc([C@H](C)NC(=O)[C@@H]2C[C@@H](O)CN2C(=O)[C@@H](NC(=O)CC2CCN(c3cc(-c4ccccc4O)nnc3N)CC2)C(C)(C)C)cc1] |
| 81. | 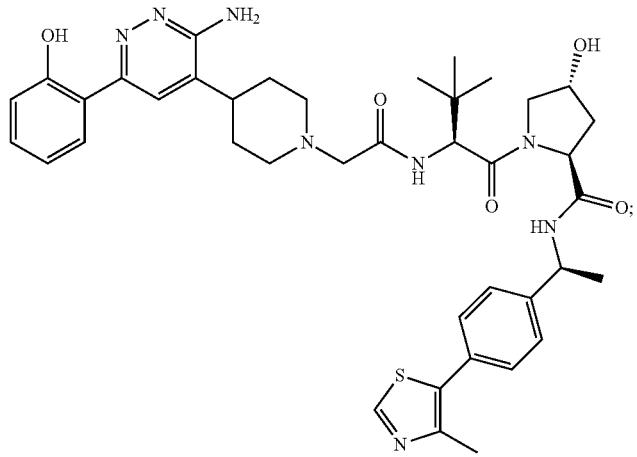 [SMILES: Cc1ncsc1-c1ccc([C@H](C)NC(=O)[C@@H]2C[C@@H](O)CN2C(=O)[C@@H](NC(=O)CN2CCC(c3cc(-c4ccccc4O)nnc3N)CC2)C(C)(C)C)cc1] |
| 82. | 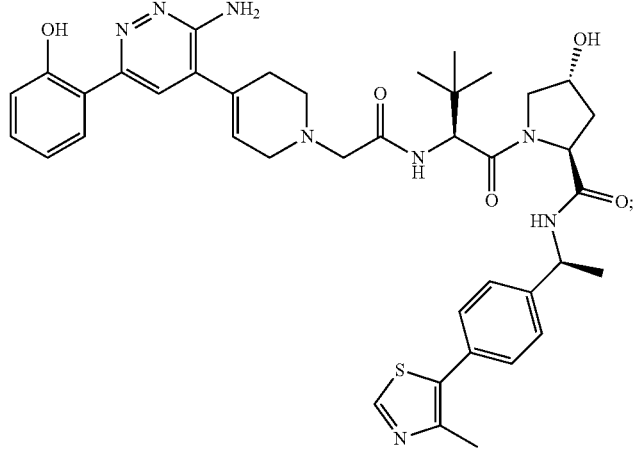 [SMILES: Cc1ncsc1-c1ccc([C@H](C)NC(=O)[C@@H]2C[C@@H](O)CN2C(=O)[C@@H](NC(=O)CN2CC=C(c3cc(-c4ccccc4O)nnc3N)CC2)C(C)(C)C)cc1] |

-continued
| Compound No | Structure |
|---|---|
| 83. and 84. | 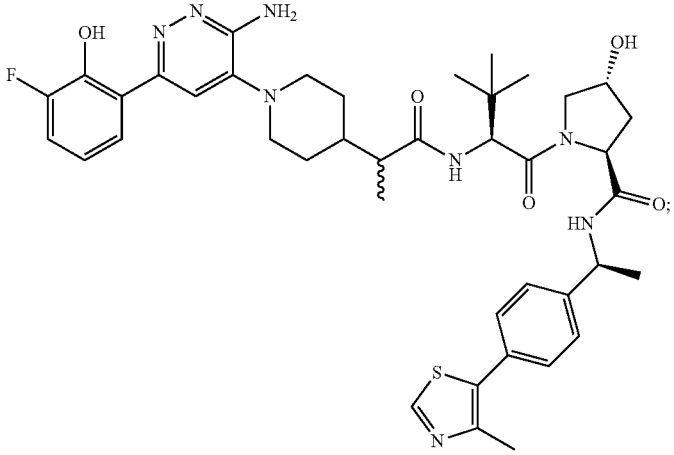<br>Isomer-1 and Isomer-2 |
| 85. | 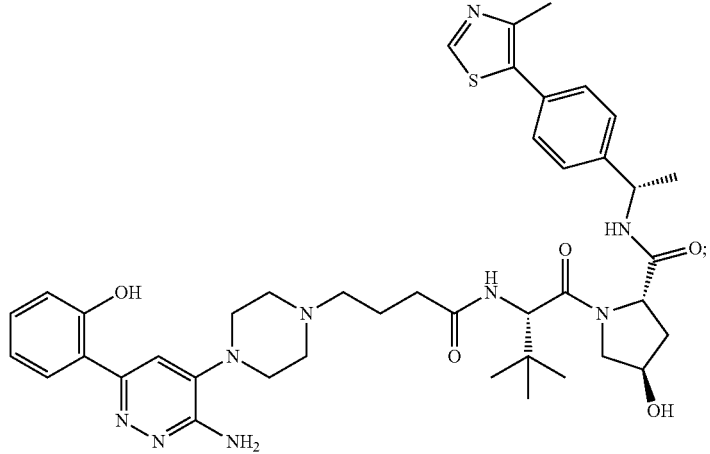 [SMILES: Cc1ncsc1-c1ccc([C@H](C)NC(=O)[C@@H]2C[C@@H](O)CN2C(=O)[C@@H](NC(=O)CCCN2CCN(c3cc(-c4ccccc4O)nnc3N)CC2)C(C)(C)C)cc1] |
| 86. | 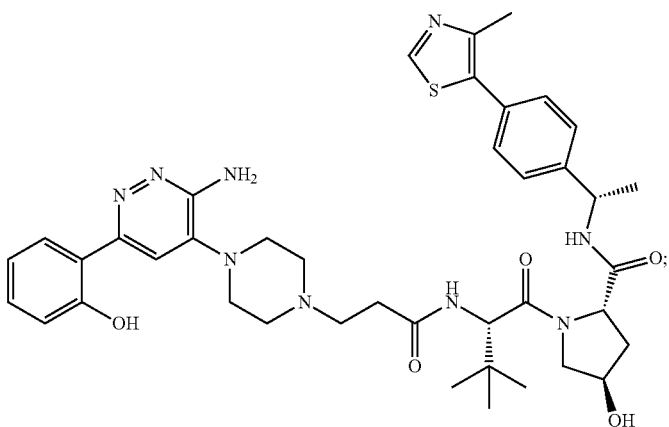 [SMILES: Cc1ncsc1-c1ccc([C@H](C)NC(=O)[C@@H]2C[C@@H](O)CN2C(=O)[C@@H](NC(=O)CCN2CCN(c3cc(-c4ccccc4O)nnc3N)CC2)C(C)(C)C)cc1] |

| Compound No | Structure |
|---|---|
| 87. | 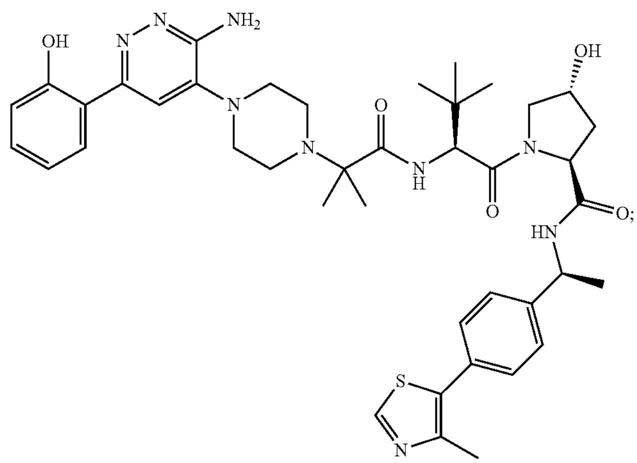 [SMILES: Cc1ncsc1-c1ccc([C@H](C)NC(=O)[C@@H]2C[C@@H](O)CN2C(=O)[C@@H](NC(=O)C(C)(C)N2CCN(c3cc(-c4ccccc4O)nnc3N)CC2)C(C)(C)C)cc1] |
| 88. | 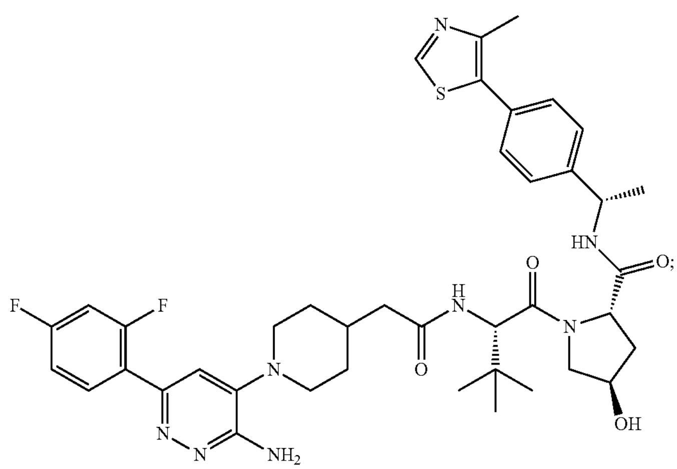 [SMILES: Cc1ncsc1-c1ccc([C@H](C)NC(=O)[C@@H]2C[C@@H](O)CN2C(=O)[C@@H](NC(=O)CC2CCN(c3cc(-c4ccc(F)cc4F)nnc3N)CC2)C(C)(C)C)cc1] |
| 89. | 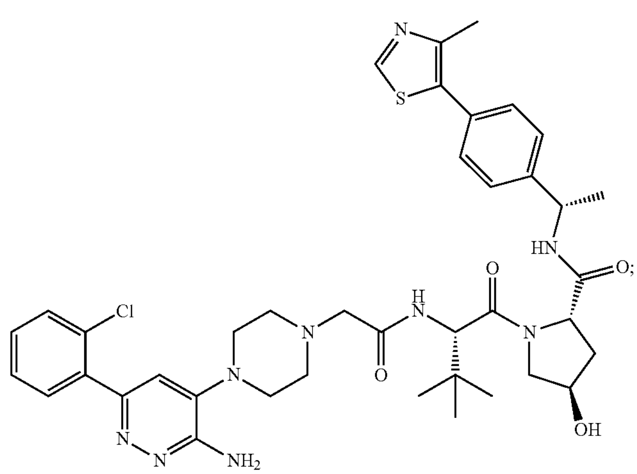 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4Cl)nnc3N)CC2)C(C)(C)C)cc1] |

| Compound No | Structure |
|---|---|
| 90. | 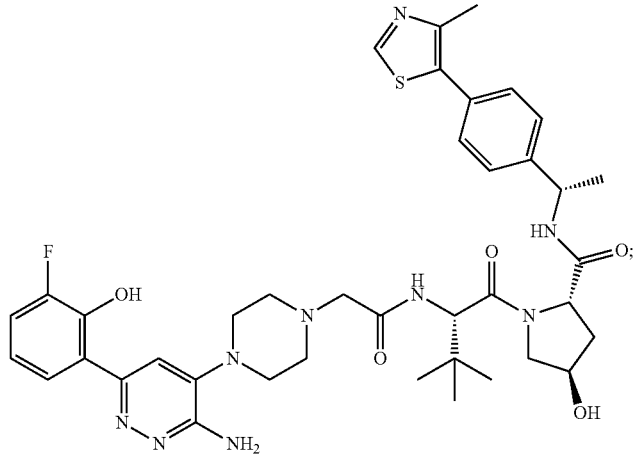 |
| 91. | 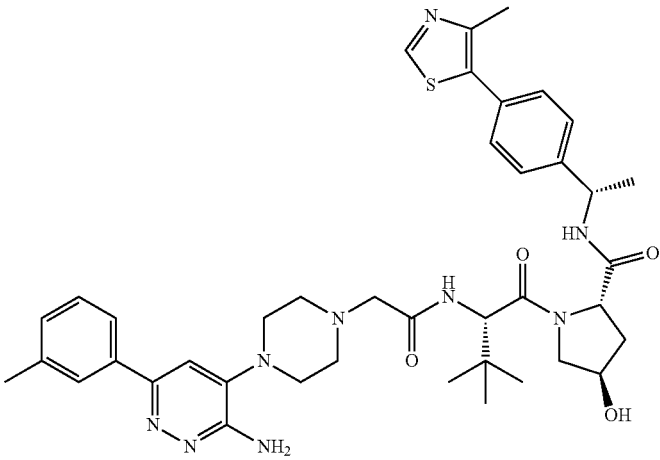 |
| 92. | 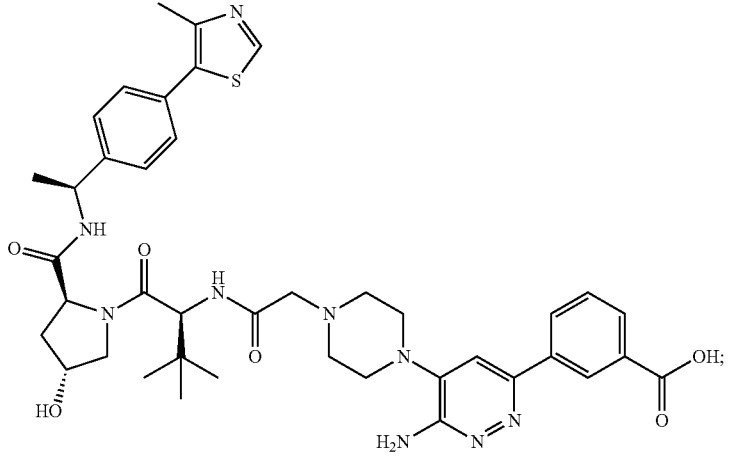 [SMILES: Cc1ncsc1-c1ccc([C@H](C)NC(=O)[C@@H]2C[C@@H](O)CN2C(=O)[C@@H](NC(=O)CN2CCN(c3cc(-c4cccc(C(=O)O)c4)nnc3N)CC2)C(C)(C)C)cc1] |

| Compound No | Structure |
|---|---|
| 93. | 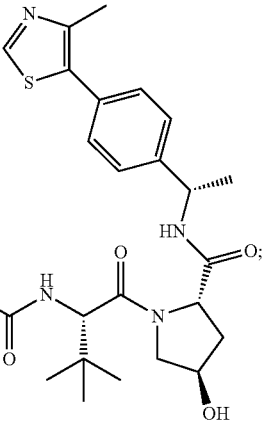 |
| 94. | 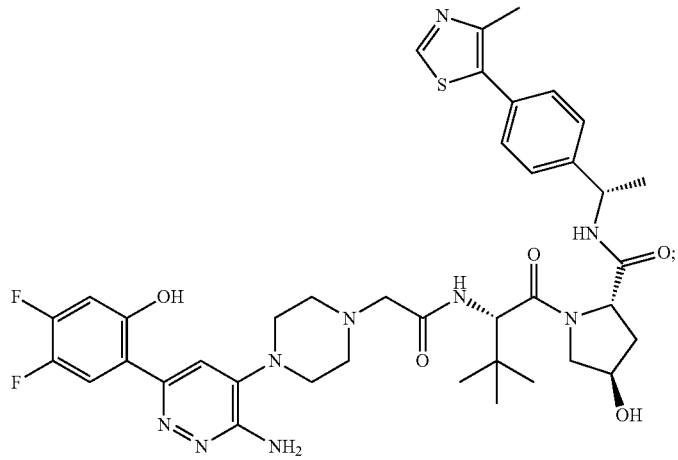 [SMILES: Cc1ncsc1-c1ccc([C@H](C)NC(=O)[C@@H]2C[C@@H](O)CN2C(=O)[C@@H](NC(=O)CN2CCN(c3cc(-c4cc(F)c(F)cc4O)nnc3N)CC2)C(C)(C)C)cc1] |
| 95. | 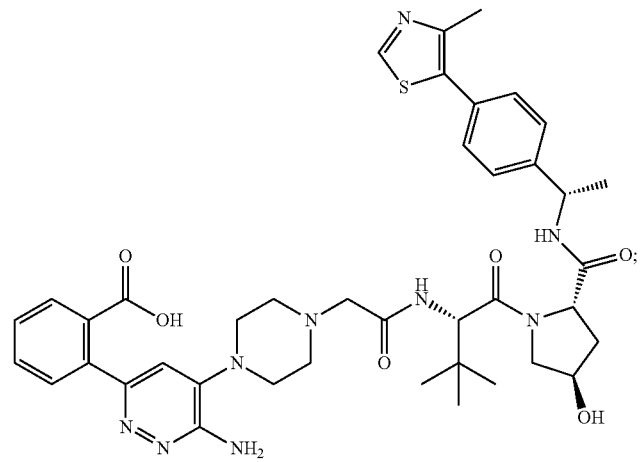 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4C(=O)O)nnc3N)CC2)C(C)(C)C)cc1] |

| Compound No | Structure |
|---|---|
| 96. | 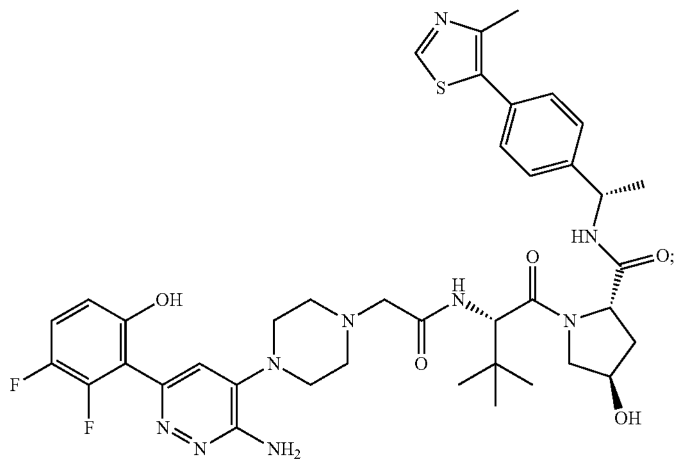 [SMILES: Cc1ncsc1-c1ccc([C@H](C)NC(=O)[C@@H]2C[C@@H](O)CN2C(=O)[C@@H](NC(=O)CN2CCN(c3cc(-c4c(O)ccc(F)c4F)nnc3N)CC2)C(C)(C)C)cc1] |
| 97. | 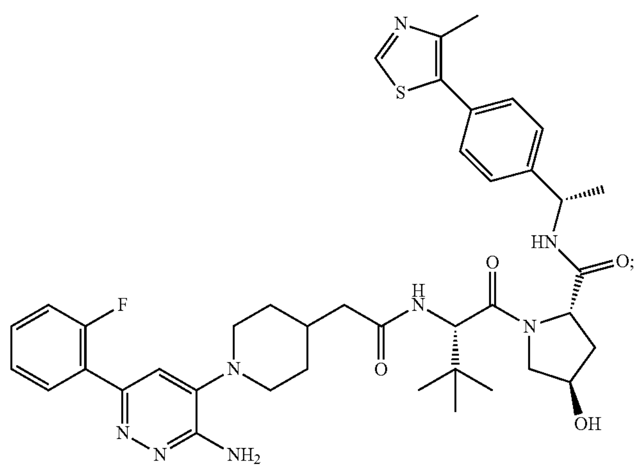 [SMILES: Cc1ncsc1-c1ccc([C@H](C)NC(=O)[C@@H]2C[C@@H](O)CN2C(=O)[C@@H](NC(=O)CC2CCN(c3cc(-c4ccccc4F)nnc3N)CC2)C(C)(C)C)cc1] |
| 98. | 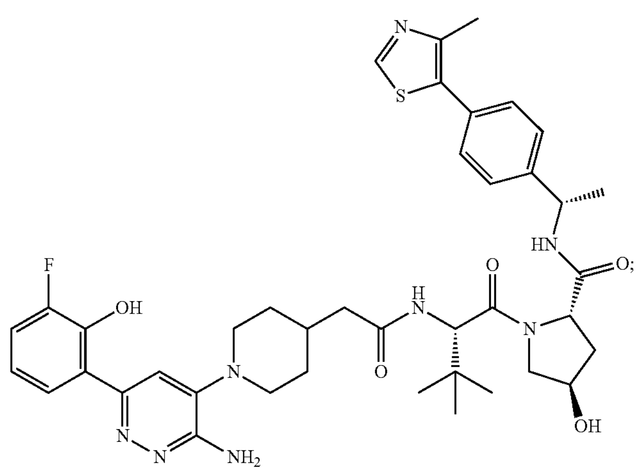 [SMILES: Cc1ncsc1-c1ccc([C@H](C)NC(=O)[C@@H]2C[C@@H](O)CN2C(=O)[C@@H](NC(=O)CC2CCN(c3cc(-c4cccc(F)c4O)nnc3N)CC2)C(C)(C)C)cc1] |

| Compound No | Structure |
|---|---|
| 99. | 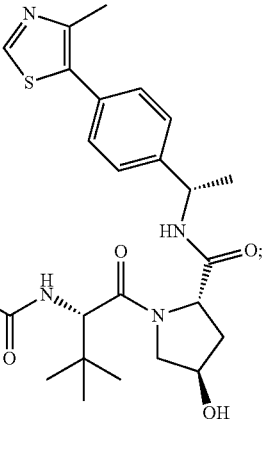 |
| 100. | 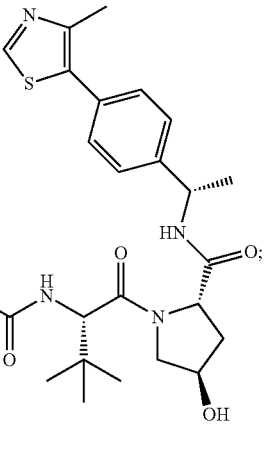 |
| 101. | 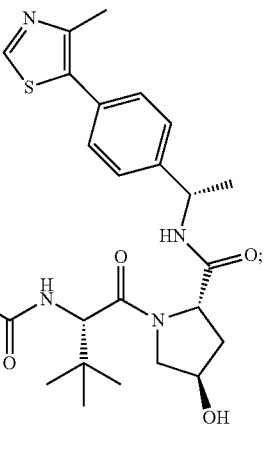 |

| Compound No | Structure |
|---|---|
| 102. | (structure) |
| 103. | (structure) |
| 104. | (structure) |

| Compound No | Structure |
|---|---|
| 105. | 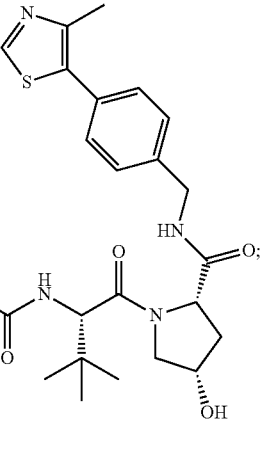 |
| 106. | 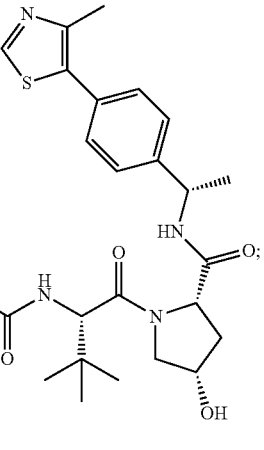 |
| 107. | 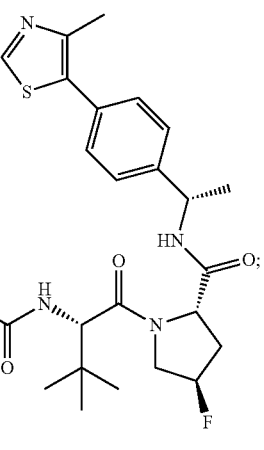 |

| Compound No | Structure |
|---|---|
| 108. | (chemical structure) |
| 109. | (chemical structure) |
| 110. | (chemical structure) |

| Compound No | Structure |
|---|---|
| 111. | 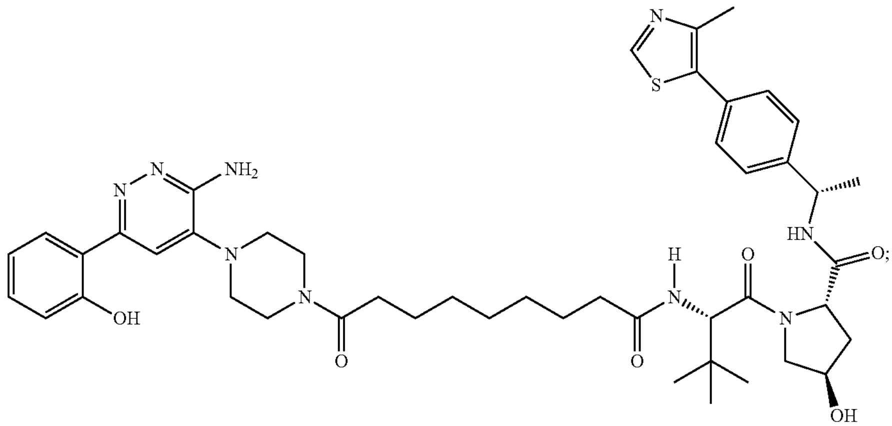 [SMILES: Cc1ncsc1-c1ccc([C@H](C)NC(=O)[C@@H]2C[C@@H](O)CN2C(=O)[C@@H](NC(=O)CCCCCCCC(=O)N2CCN(c3cc(-c4ccccc4O)nnc3N)CC2)C(C)(C)C)cc1] |
| 112. | 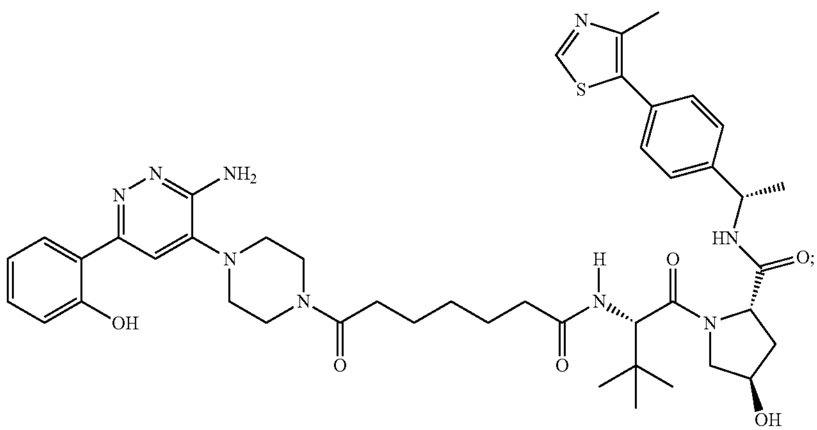 [SMILES: Cc1ncsc1-c1ccc([C@H](C)NC(=O)[C@@H]2C[C@@H](O)CN2C(=O)[C@@H](NC(=O)CCCCCC(=O)N2CCN(c3cc(-c4ccccc4O)nnc3N)CC2)C(C)(C)C)cc1] |
| 113. | 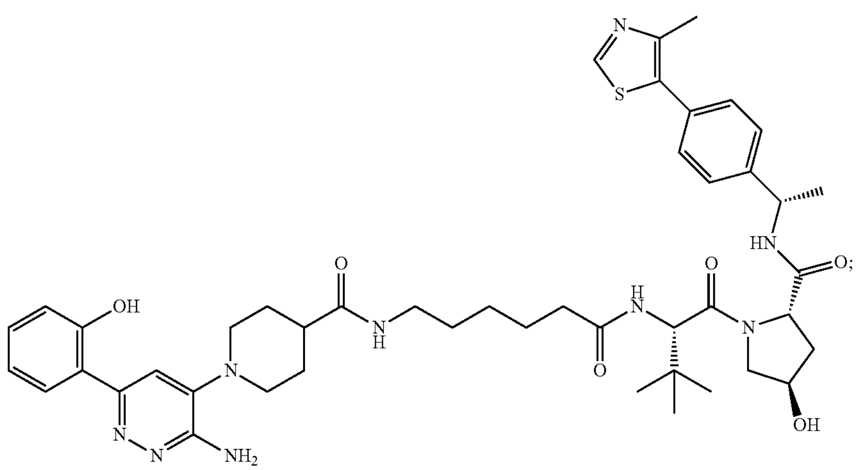 [SMILES: Cc1ncsc1-c1ccc([C@H](C)NC(=O)[C@@H]2C[C@@H](O)CN2C(=O)[C@@H](NC(=O)CCCCCNC(=O)C2CCN(c3cc(-c4ccccc4O)nnc3N)CC2)C(C)(C)C)cc1] |

-continued

| Compound No | Structure |
|---|---|
| 114. | 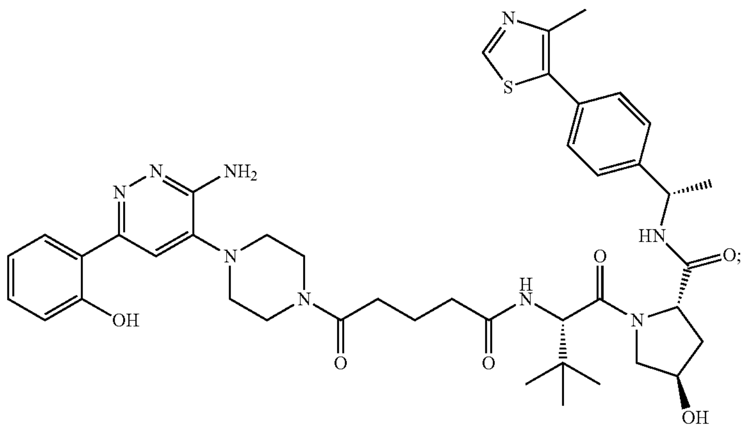 [SMILES: Cc1ncsc1-c1ccc([C@H](C)NC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] |
| 115. | 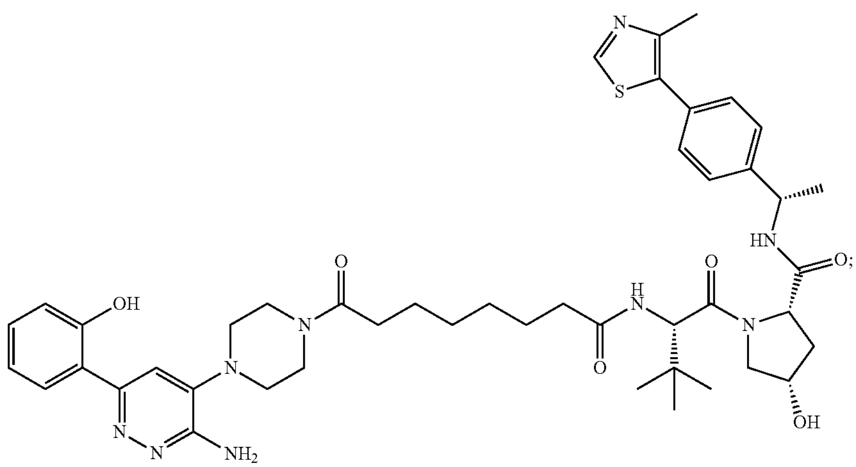 [SMILES: Cc1ncsc1-c1ccc([C@H](C)NC(=O)[C@@H]2C[C@H](O)CN2C(=O)[C@@H](NC(=O)CCCCCCC(=O)N2CCN(c3cc(-c4ccccc4O)nnc3N)CC2)C(C)(C)C)cc1] |
| 116. | 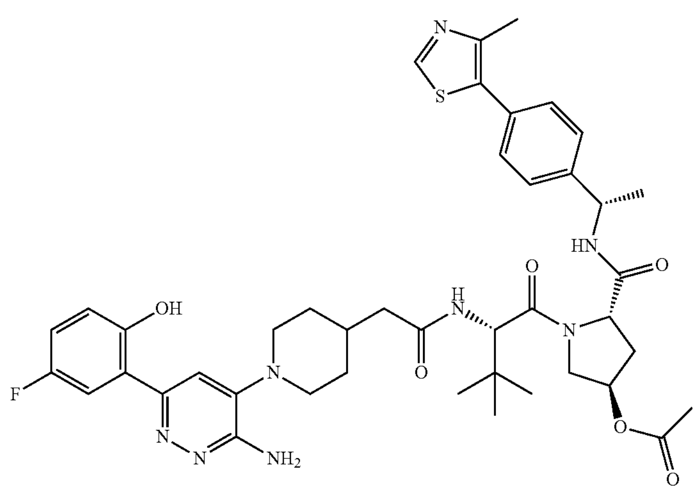 |

| Compound No | Structure |
|---|---|
| 117. | 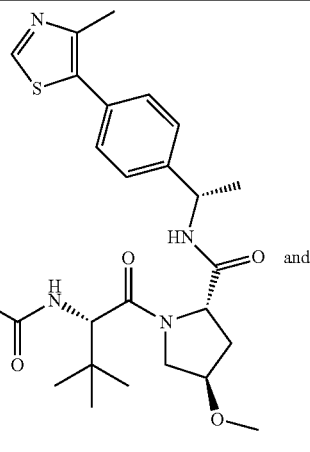 and |
| 118. | 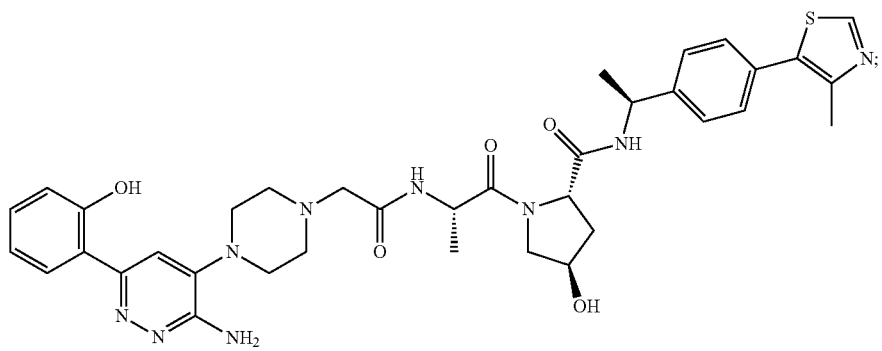 [SMILES: Cc1ncsc1-c1ccc([C@H](C)NC(=O)[C@@H]2C[C@@H](O)CN2C(=O)[C@H](C)NC(=O)CN2CCN(c3cc(-c4ccccc4O)nnc3N)CC2)cc1] | or a pharmaceutically acceptable salt or a stereoisomer thereof.

In certain embodiments, the present invention provides a method of selecting a patient with prostate cancer for treatment with a SMARCA2/4 degrader, comprising:
a) isolating a biological sample from the patient;
b) determining whether one or more tumor specific alterations are present; wherein the tumor specific alterations comprise; and
c) selecting the patient for the treatment with the SMARCA2/4 degrader in whose sample at least one of the tumor specific alterations is present.

In certain embodiments, the present invention provides a method of selecting a patient with prostate cancer for treatment with a SMARCA2/4 degrader, comprising:
a) isolating a biological sample from the patient;
b) determining whether one or more tumor specific alterations are present; wherein the tumor specific alterations comprise; and
c) selecting the patient for the treatment with the SMARCA2/4 degrader in whose sample at least one of the tumor specific alterations is present; and
d) administering the treatment comprising a therapeutically effective amount of at least one SMARCA2/4 degrader to the selected patient.

In certain embodiments, the present invention provides a method of selecting a patient with prostate cancer for treatment with a SMARCA2/4 degrader, comprising:
a) isolating a biological sample from the patient;
b) determining whether one or more tumor specific alterations are present; wherein the tumor specific alterations comprise;
   a mutation, an amplification, or an overexpression of Androgen Receptor (AR) gene;
   a loss of function or a deleterious mutation in phosphatase and tensin homolog (PTEN); or
   a genomic rearrangement that results in translocation between TMPRSS2 and ERG genes; and
c) selecting the patient for the treatment with the SMARCA2/4 degrader in whose sample at least one of the tumor specific alterations is present.

In certain embodiments, the present invention provides a method of selecting a patient with prostate cancer for treatment with a SMARCA2/4 degrader in combination with another therapeutic agent, wherein the method comprising:
a) isolating a biological sample from the patient;
b) determining whether one or more tumor specific alterations are present; wherein the tumor specific alterations comprise; and
c) selecting the patient for the treatment with the SMARCA2/4 degrader in whose sample at least one of the tumor specific alterations is present; and
d) administering the treatment comprising a therapeutically effective amount of at least one SMARCA2/4 degrader to the selected patient.

In certain embodiments, the present invention provides a method of selecting a subject with prostate disease for treatment with a SMARCA2/4 degrader, comprising:
a) isolating a biological sample from the subject;
b) determining whether one or more tumor specific alterations are present in the biological sample;
c) selecting the subject for the treatment with the SMARCA2/4 degrader in whose sample at least one tumor specific alterations is present; and
d) administering the treatment comprising a therapeutically effective amount of at least one SMARCA2/4 degrader to the selected subject.

In certain embodiments, the present invention provides a method of selecting a subject with prostate disease for treatment with a SMARCA2/4 degrader wherein the method is in-vitro.

In certain embodiments, the present invention provides compound of formula (I) or a pharmaceutically acceptable salt thereof or a stereoisomer thereof for use in method of selecting the subject with prostate cancer for treatment with a SMARCA2/4 degrader.

In certain embodiments, the present invention provides a method of inhibiting proliferation of prostate cancer cells, comprising the step of contacting the prostate cancer cells with at least one SMARCA2/4 degrader.

In one embodiment, the present invention provides a method of inhibiting proliferation of prostate cancer cells in a subject, comprising:
i. isolating a biological sample from the subject;
ii. determining the presence of tumor specific alterations selected from:
   a mutation, an amplification, or an overexpression of Androgen Receptor (AR) gene;
   a loss of function or a deleterious mutation in phosphatase and tensin homolog (PTEN); and
   a genomic rearrangement that results in a translocation between a TMPRSS2 gene and an ERG gene;
iii. administering a therapeutically effective amount of at least one SMARCA2/4 degrader to the subject if at least one of tumor specific alterations is present.

In certain embodiments, the present invention provides a method of inhibiting proliferation of prostate cancer cells, comprising the step of contacting the prostate cancer cells with at least one SMARCA2/4 degrader; wherein the SMARCA2/4 degrader is represented by compound of formula (I).

In certain embodiments, the present invention provides a method of inhibiting proliferation of prostate cancer cells harboring one or more tumor specific alterations, comprising the step of contacting the prostate cancer cells with at least one SMARCA2/4 degrader; wherein the SMARCA2/4 degrader is represented by compound of formula (I).

In certain embodiments, the present invention provides a method of inhibiting proliferation of prostate cancer cells, comprising the step of contacting the prostate cancer cells with at least one SMARCA2/4 degrader; wherein the SMARCA2/4 degrader is a compound described in Table-A.

In certain embodiments, the present invention provides a method of inhibiting proliferation of prostate cancer cells harboring one or more tumor specific alterations, comprising the step of contacting the prostate cancer cells with at least one SMARCA2/4 degrader; wherein the SMARCA2/4 degrader is a compound described in Table-A.

In certain embodiments, the present invention provides a method of inhibiting proliferation of prostate cancer cells, wherein the prostate cancer cells comprise a prostate tumor in a subject.

In certain embodiments, the present invention provides a method of inhibiting proliferation of prostate cancer cells, wherein the method is in-vitro.

Definitions:

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein, the term "tumor specific alterations" refers to any change in the genome leading to a change in DNA sequence, mRNA sequence, protein sequence, changes in gene expression (either mRNA or protein abundance), or combinations thereof. Tumor specific alterations includes, but not limited to, deleterious mutations (e.g., mutations that reduce or abolish either gene function or gene expression), loss of function mutations, gain of function mutations and others. Tumor specific alterations includes insertions of viral genetic material into the genome of infected host cells (e.g., human papillomavirus). Tumor specific alterations also includes microsatellites or other repetitive tracts of DNA (e.g., short tandem repeats or simple sequence repeats).

As used herein, the phrase "gain of function mutation" with respect to any specific gene or gene product, refers to a type of mutation in which the altered gene product possesses a new molecular function or a new pattern of gene expression.

As used herein, "loss of function" (LOF) mutation refers to a mutation or allele of a gene, the result of which is that the gene product (such as the encoded protein) has less than normal or no function in a cell or organism (including a human cell or human being). When the allele has a complete loss of function (null allele) it is often called an amorphic mutation. Phenotypes associated with loss of function mutations are often recessive.

As used herein, the term "overexpression" when referring to a gene (e.g., an oncogenic driver gene), refers to any increase in mRNA, protein, or combinations thereof corresponding to a gene compared to normal level. For instance, the term "overexpression of AR gene" refers to any increase in mRNA level, protein level, or combinations thereof corresponding to AR gene.

As used herein, the term "genomic rearrangement of the TMPRSS2 and ERG genes" refers to any rearrangement of the TMPRSS2 and ERG genes that is associated with prostate cancer and can include a gene fusion between the TMPRSS2 gene and the ERG. Such genomic rearrangement may result in translocation between TMPRSS2 and ERG genes.

As used herein, the term "therapeutically effective amount" of a pharmaceutical agent or combination of agents is intended to refer to an amount of agent(s) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific pharmaceutical agent employed; the duration of the treatment; and like factors as is well known in the medical arts.

As used herein, the term "treatment" (also "treat" or "treating") refers to any administration of a pharmaceutical agent, remedy, or medicament that partially or completely alleviates, ameliorates, relieves, inhibits, delays onset of, reduces severity of and/or reduces incidence of one or more symptoms or features of a particular disease, disorder, syndrome and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as the event or circumstance where the alkyl is not substituted.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an oxo, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heteroaryl, a heterocycloalkyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to saturated aliphatic groups, including but not limited to $C_1$-$C_{10}$ straight-chain alkyl groups or $C_3$-$C_{10}$ branched-chain alkyl groups. Preferably, the "alkyl" group refers to $C_1$-$C_6$ straight-chain alkyl groups or $C_3$-$C_6$ branched-chain alkyl groups. Most preferably, the "alkyl" group refers to $C_1$-$C_4$ straight-chain alkyl groups or $C_3$-$C_8$ branched-chain alkyl groups. Examples of "alkyl" include, but are not limited to, methyl, ethyl, 1-propyl, 2-propyl, isopropyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. The "alkyl" group may be optionally substituted.

As used herein, the term "haloalkyl" refers to alkyl substituted with one or more halogen atoms, wherein the halo and alkyl groups are as defined above. Examples of "haloalkyl" include but are not limited to fluoromethyl, difluoromethyl, chloromethyl, trifluoromethyl and 2,2,2-trifluoroethyl.

As used herein, the term "hydroxylalkyl" or "hydroxyalkyl" refers to an alkyl group, as defined above, wherein one or more of the alkyl group's hydrogen atoms have been replaced with hydroxyl group. Examples of hydroxylalkyl moieties include but are not limited to —$CH_2OH$, —$CH_2CH_2OH$, —$CH_2CH_2CH_2OH$, —$CH_2CH(OH)$ $CH_2OH$, —$CH_2CH(OH)$ $CH_3$, —$CH(CH_3)CH_2OH$.

As used herein, the term "heterocycloalkyl" refers to a non-aromatic, saturated or partially saturated, bridged bicyclic, spirocyclic, monocyclic or polycyclic ring system of 3 to member having at least one heteroatom or heterogroup selected from O, N, S, S(O), $S(O)_2$, NH and C(O) with the remaining ring atoms being independently selected from the group consisting of carbon, oxygen, nitrogen, and sulfur. The term "heterocycloalkyl" also refers to the bridged bicyclic ring system having at least one heteroatom or hetero group selected from O, N, S, S(O), $S(O)_2$, NH and C(O). Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, dihydropyridinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, isoindolinyl, oxoisoindolinyl, dioxoisoindolinyl, aza-bicyclooctanyl, diazabicyclooctanyl, azocinyl, chromanyl, isochromanyl xanthenyl, 2-oxa-6-azaspiro[3.3]heptanyl, thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, and thiomorpholinyl thereof. All heterocycloalkyl are optionally substituted by one or more aforesaid groups.

As used herein, the term "heteroaryl" alone or in combination with other term(s) means a completely unsaturated ring system containing a total of 5 to 14 ring atoms. At least one of the ring atoms is a heteroatom (i.e., oxygen, nitrogen, or sulfur), with the remaining ring atoms/groups being independently selected from carbon, oxygen, nitrogen or sulfur. A heteroaryl may be a single-ring (monocyclic) or multiple rings (bicyclic, tricyclic or polycyclic) fused together or linked covalently. Preferably, "heteroaryl" is a 5- to 6-membered ring. The rings may contain from 1 to 4 additional heteroatoms selected from N, O and S, wherein the N atom is optionally quarternized. Any suitable ring position of the heteroaryl moiety may be covalently linked to the defined chemical structure. Examples of "heteroaryl" include but are not limited to furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, 3-fluoropyridyl, pyrimidinyl, pyrazinyl, pyridazinyl, benzoxazolyl, benzisoxazolyl; benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carbolinyl, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and the like. Heteroaryl group may be optionally further substituted.

As used herein, the term "alkenyl" refers to a carbon chain which contains at least one carbon-carbon double bond, and which may be linear or branched or combinations thereof. Examples of "alkenyl" include, but not limited to, vinyl, allyl, isopropenyl, pentenyl, hexenyl, heptenyl, 1-propenyl, 2-butenyl and 2-methyl-2-butenyl.

As used herein, the term "amino" refers to an —$NH_2$ group.

As used herein, the term "halo" or "halogen" alone or in combination with other term(s) means fluorine, chlorine, bromine or iodine.

As used herein, the term "hydroxy" or "hydroxyl" alone or in combination with other term(s) means —OH.

As used herein, the term "oxo" refers to =O group.

As used herein, the term "alkoxy" refers to the group —O-alkyl, where alkyl groups are as defined above. Exemplary $C_1$-$C_{10}$ alkoxy group include but are not limited to methoxy, ethoxy, n-propoxy, n-butoxy or t-butoxy. An alkoxy group can be optionally substituted with one or more suitable groups.

As used herein, the term "aryl" is optionally substituted monocyclic, bicyclic or polycyclic aromatic hydrocarbon ring system of about 6 to 14 carbon atoms. Examples of a $C_6$-$C_{14}$ aryl group include, but are not limited to phenyl, naphthyl, biphenyl, anthryl, fluorenyl, indanyl, biphenylenyl and acenaphthyl. Aryl group can be unsubstituted or substituted with one or more suitable groups.

The term "acyl" refers to a group R—CO— or —CO—R wherein R is an optionally substituted alkyl group defined above. Examples of 'acyl' group includes, but not limited to $CH_3CO$—, $CH_3CH_2CO$—, $CH_3CH_2CH_2CO$— or $(CH_3)_2CHCO$—. The term "—O-acyl" refers to —O—CO—R wherein R is an alkyl as defined above.

The term "heteroatom" as used herein designates a sulfur, nitrogen or oxygen atom.

The term "subject" denotes a mammal, for example human. In one embodiment of the invention, a subject refers to any subject afflicted with a prostate disease. In another embodiment of the invention, the term "subject" refers to any subject afflicted with prostate cancer. In another embodiment of the invention, the term "subject" refers to any subject afflicted with a castration-resistant prostate cancer. In another embodiment of the invention, the term "subject" refers to any subject who has undergone castration. In another embodiment of the invention, the term "subject" refers to any subject who has undergone anti-androgen therapy. In another embodiment, the term "subject" refers to any subject afflicted with castration-resistant prostate cancer receiving a SMARCA2/4 degrader first-line therapy. In another embodiment, the term "subject" refers to any subject afflicted with a castration-resistant prostate cancer receiving a combination therapy of SMARCA2/4 degrader and any other therapeutic agents.

The term 'moderate responder' to the treatment with SMARCA2/4 degrader, when referred to the subject of the present invention, shall mean the subject harboring any one of the tumor specific alterations of the present invention.

The term 'high responder' to the treatment with SMARCA2/4 degrader, when referred to the subject of the present invention, shall mean the subject harboring at least two of the tumor specific alterations of the present invention. For example, the subject can be referred as 'high responder' to the treatment with SMARCA2/4 degrader when the following alteration occurs:

i. a mutation, an amplification, or an overexpression of Androgen Receptor (AR) gene; and a loss of function or a deleterious mutation in phosphatase and tensin homolog (PTEN);

ii. a loss of function or a deleterious mutation in phosphatase and tensin homolog (PTEN); and a genomic rearrangement that results in translocation between TMPRSS2 and ERG genes; and iii. a mutation, an amplification, or an overexpression of Androgen Receptor (AR) gene; and a genomic rearrangement that results in translocation between TMPRSS2 and ERG genes.

EXPERIMENTAL

The synthetic procedures for the preparation of compounds of the present invention were described in International application PCT/IB2019/053443 which is hereby incorporated in its entirety.

Example—1

Determination of Anti-Proliferative Activity of SMARCA2/4 Degrader in Cells by Cell Titer Glo® (Promega) Assay The prostate cancer cell lines, Vcap (ATCC #CRL-2876), LNCaP-FGC (ATCC CRL-1740), 22RV1 (ATCC CRL-2505), PC-3 (ATCC CRL-1435), DU-145 (ATCC HTB-81) and RWPE-1 (ATCC CRL-11609) were seeded in 96 well plate flat black clear bottom plates (Corning, Cat. No 3904) using respective complete media. Simultaneously cells were seeded for day 0 measurement.

On the following day, compound 43 of the present invention was added to cells from 10 mM stocks made in DMSO (Sigma Cat no. D2650). DMSO alone was used a vehicle control. Day 0 plate was terminated on day of compound addition using 50 µl of Cell Titer Glo® reagent (Promega, Cat. no G7572). Compound was incubated for 8 days, except for 22RV1 which was incubated for 6 days. Media was replenished with fresh compound on day 4. After the compound incubation, assay was terminated using 50 µl of CellTiter Glo® reagent. CellTiter Glo® Luminescent reagent determines the number of viable cells based on quantitation of ATP present which is an indicator of cell number and metabolic activity. Luminescence readings were taken in fluorescent plate reader.

Day 0 CTG measurement is designated as time zero (Tz), final CTG measurement in Vehicle control is designated as control growth DMSO (C) and test growth in the presence of drug at the nine concentration levels is designated as (Ti).

Using the measurements [time zero (Tz), growth control DMSO (C) and test growth in the presence of drug at the nine concentration levels (Ti)] the percentage growth is calculated at each of the drug concentration levels. Percentage response is calculated as:

$[(Ti-Tz)/(C-Tz)] \times 100$ for Concentrations for which $Ti \geq Tz$ $[(Ti-Tz)/Tz] \times 100$ for Concentrations for which $Ti < Tz$ Three dose response parameters are calculated for each experimental agent. Growth inhibition of 50% ($GI_{50}$) is calculated from $[(Ti-Tz)/(C-Tz)] \times 100 = 50$, which is the drug concentration resulting in a 50% reduction in the net luminescence increase (measured ATP) in control cells during the drug incubation. The results are given in Table-II.

The $LC_{50}$ (concentration of drug resulting in a 50% reduction in the measured ATP at the end of the drug treatment as compared to that at the beginning) indicating a net loss of cells following treatment is calculated from $[(Ti-Tz)/Tz] \times 100 = -50$.

Determination of Sensitivity of Prostate Cancer Cell Lines to SMARCA2/4 Degrader Compound 43 of the present invention was analyzed against several cell lines representing normal and prostate cancer cells. The cell lines used in the present invention are harboring one or more tumor specific alterations such as presence of AR, PTEN mutations or TMPRSS2-ERG fusion which are presented below.

TABLE I

| Cell line | $GI_{50}$ (nM) | Observed cell killing | Tumor-specific alterations of present invention | | |
|---|---|---|---|---|---|
| | | | AR Dependence | PTEN mutation | TMPRSS2-ERG fusion |
| RWPE (Normal) | 260* | No | Normal AR | – | – |
| DU145 | >10000 | No | – | – | – |
| 22RV1 | 14 | No | + | – | – |
| PC3 | 51 | Yes ($LC_{50}$ = 3406 nM) | – | + | – |
| VCap | 3 | Yes ($LC_{50}$ = 11 nM) | + | – | + |
| LnCapF GC | 5 | Yes ($LC_{50}$ = 22 nM) | + | + | – |

Figure 2:
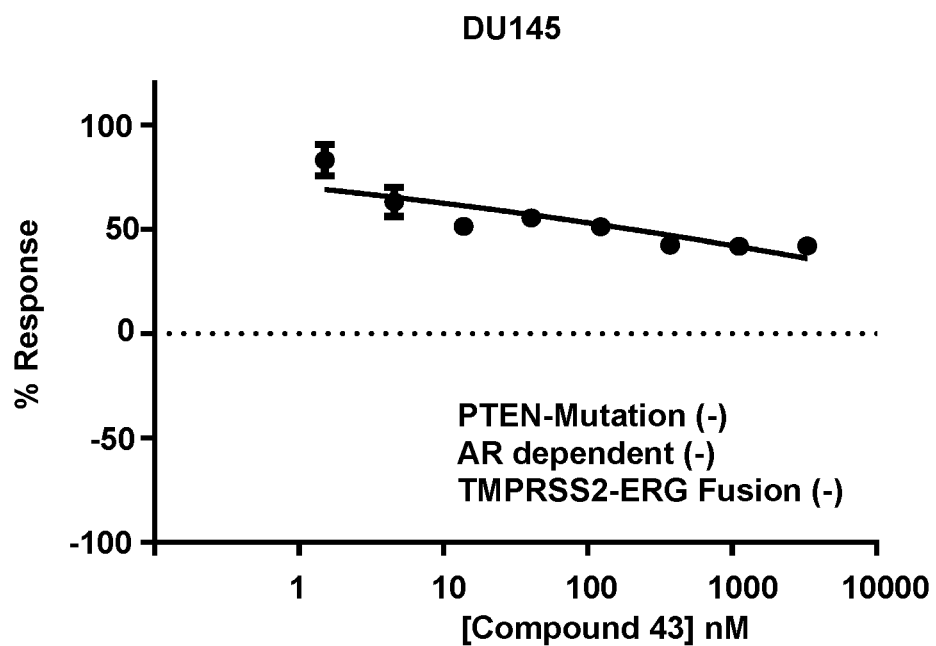
FIG. 2: Anti-proliferative activity of SMARCA2/4 degrader of present invention in DU145 cells wherein no tumor specific alterations described herein is present.
Figure 3A:
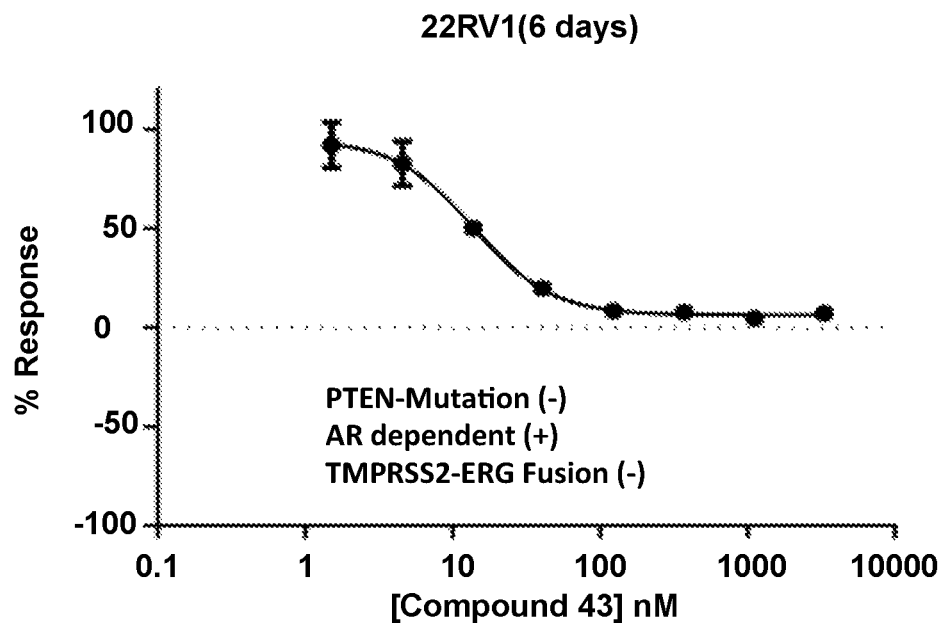
FIG. 3A: Anti-proliferative activity of SMARCA2/4 degrader of present invention in 22RV1 cells wherein the tumor specific alterations PTEN-Mutation (−), AR dependent (+), TMPRSS2-ERG Fusion (−) are met.
Figure 3B:
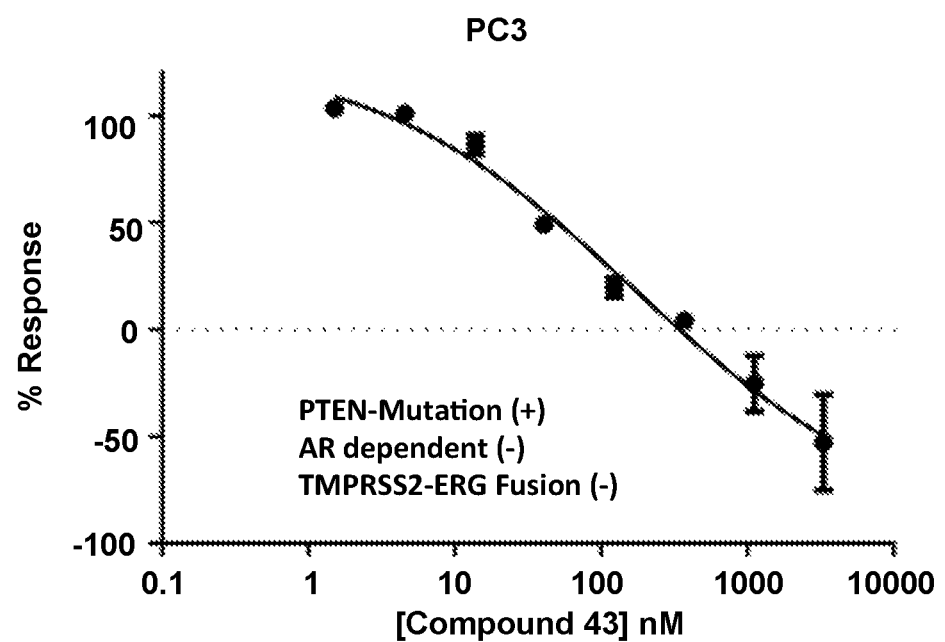
FIG. 3B: Anti-proliferative activity of SMARCA2/4 degrader of present invention in PC3 cells wherein the tumor specific alterations PTEN-Mutation (+), AR dependent (−), TMPRSS2-ERG Fusion (−) are met.
Figure 4A:
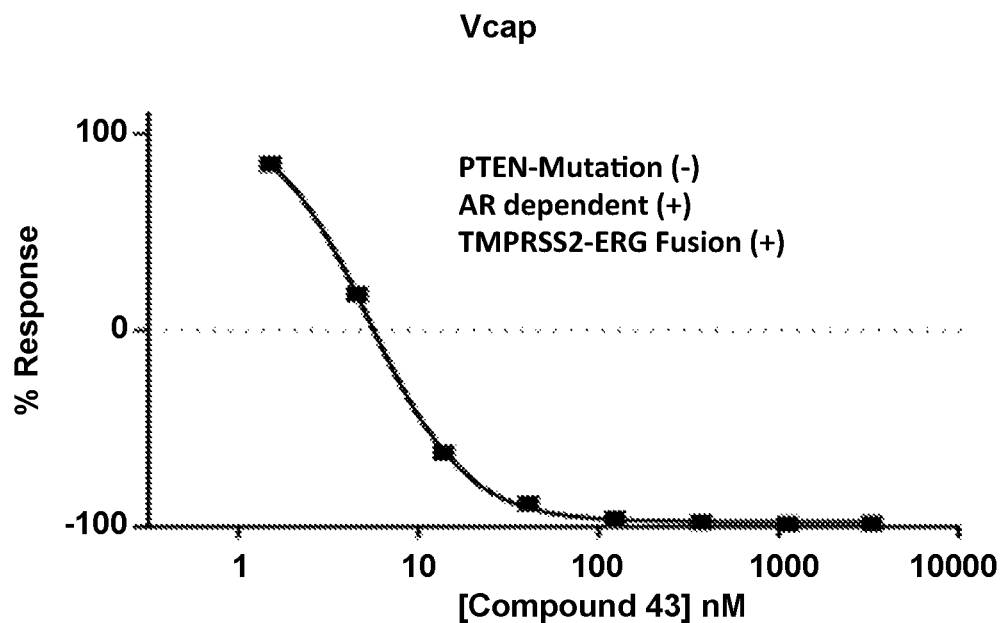
FIG. 4A: Anti-proliferative activity of SMARCA2/4 degrader of present invention in Vcap cells wherein the tumor specific alterations PTEN-Mutation (−), AR dependent (+), TMPRSS2-ERG Fusion (+) are met.
Figure 4B:
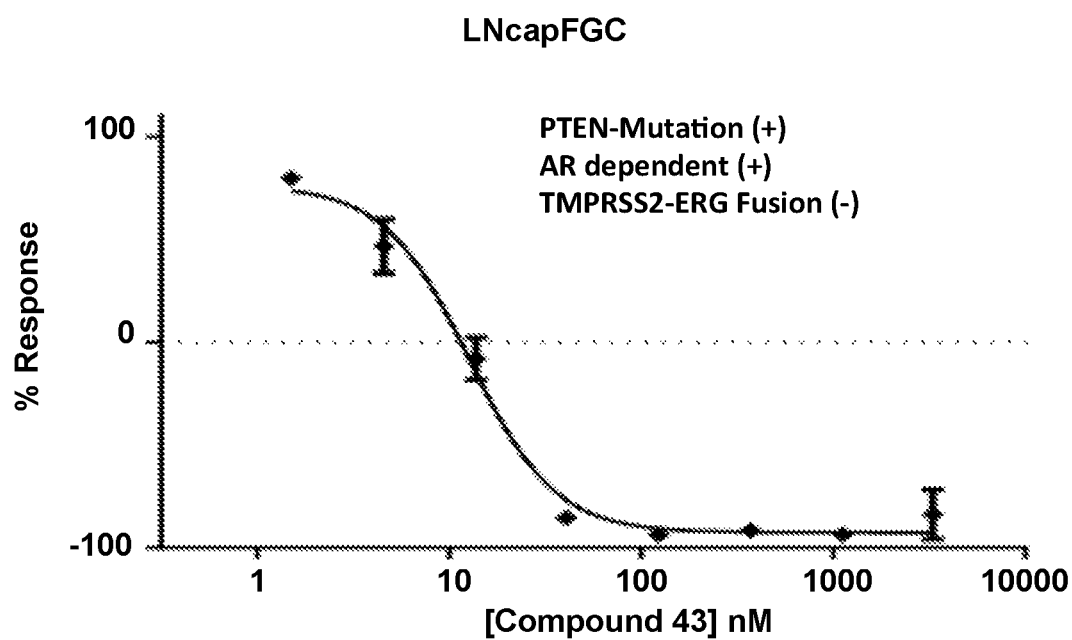
FIG. 4B: Anti-proliferative activity of SMARCA2/4 degrader of present invention in LnCap cells wherein the tumor specific alterations PTEN-Mutation (+), AR dependent (+), TMPRSS2-ERG Fusion (−) are met.

'+' sign indicates the presence of particular tumor-specific alteration in the respective cell line
'–' sign indicates the absence of particular tumor-specific alteration in the respective cell line In normal cell (RWPE), it was observed that the compound did not show any inhibition and cell killing (FIG. 1). In prostate cancer cell line DU145 with none of the tumor specific alterations is present, neither inhibition of cell growth nor cell killing was observed and hence DU145 was determined to be no or poor responder to SMARCA2/4 degrader (FIG. 2). Growth of 22RV1 and PC3, cell lines with one of the said tumor-specific alterations is present, was potently inhibited with no or moderate cell killing (FIGS. 3A-3B). And, both growth and cell killing were potently impacted in VCap and LnCapFGC, cell lines with two of the said three tumor specific alterations (FIGS. 4A-4B).

These observations support the use of AR dependence, PTEN mutation and the presence of TMPRSS2-ERG genes fusion as the biomarker to determine the sensitivity of prostate cancer cell lines to SMARCA2/4 degraders.

The invention claimed is:

1. A method of treating a prostate disease in a subject in need thereof comprising:
   a) identifying the subject as a responder to treatment with at least one SMARCA2/4 degraders when at least one tumor specific alteration is present in the subject, wherein said tumor specific alteration is:
      a mutation, an amplification, or an overexpression of Androgen Receptor (AR) gene;
      a loss of function or a deleterious mutation in phosphatase and tensin homolog (PTEN); or
      a genomic rearrangement that results in a translocation between a TMPRSS2 gene and an ERG gene; and
   the SMARCA2/4 degrader is a compound of formula (I):

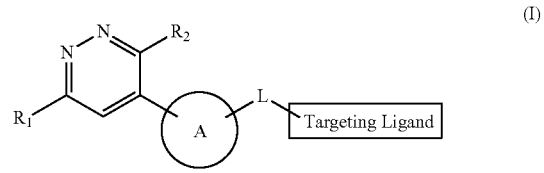

(I)

or a pharmaceutically acceptable salt thereof or a stereoisomer thereof; wherein, $R_1$ is hydrogen, halo, alkyl, alkenyl, alkoxy, hydroxy, hydroxyalkyl, —$COOR_a$—$CON(R_a)_2$, or aryl; wherein the aryl is optionally substituted independently with at least one of hydroxy, alkoxy, halo, alkyl, amino, —ONa, —$COOR_a$, or —$OCOR_a$; wherein $R_a$ at each occurrence is hydrogen or alkyl;

$R_2$ is —$NR_3R_4$ or —$OR_3$; wherein, $R_3$ and $R_4$ are independently hydrogen or alkyl;

Ring A is a heterocycloalkyl ring or a heteroaryl ring, each optionally substituted independently with at least one of hydroxy, halo or alkyl;

L is a linker with a chemical structure of:

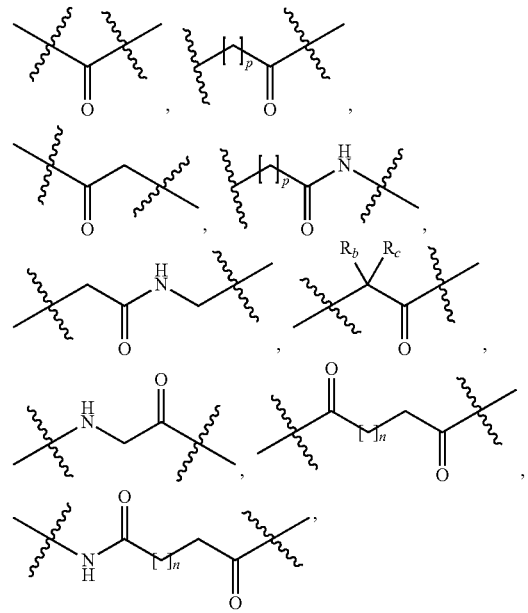

-continued

[chemical structure diagrams of linker groups]

wherein,
the left side of the linker is attached with ring A and the right side of the linker is attached with Targeting Ligand (TL);

$R_b$ is hydrogen or alkyl;

$R_c$ is alkyl;

n is 0 to 10; and p is 1 to 5;

Targeting Ligand (TL) is

[TL-1 structure with $R_8$, $R_7$, $R_6$, thiazole-methyl]

TL-1

[TL-2 structure — glutarimide-phthalimide]

TL-2

[TL-3 structure — glutarimide-isoindolinone]

TL-3 wherein $R_6$ is hydrogen, alkyl, acyl, or haloalkyl;

$R_7$ is —O—$R_5$ or halo; wherein $R_5$ is hydrogen, alkyl, acyl, or Na; and $R_8$ is hydrogen or alky; and b) administering a therapeutically effective amount of at least one SMARCA2/4 degrader to the subject who is identified to respond to the treatment, thereby treating the prostate disease.

2. The method of claim 1, wherein
the subject is identified as a moderate responder to the treatment with the SMARCA2/4 degraders if one of the tumor specific alterations is present; or
the subject is identified as a high responder to the treatment with the SMARCA2/4 degraders if at least two of the tumor specific alterations are present.

3. The method of claim 1, wherein the prostate disease is a prostate cancer.

4. The method of claim 3, wherein the prostate cancer is castration-resistant prostate cancer.

5. The method of claim 1, wherein the subject has undergone castration or anti-androgen therapy.

6. The method of claim 1, wherein the SMARCA2/4 degrader is a compound with the chemical structure of:

| Compound No | Structure |
|---|---|
| 1. | 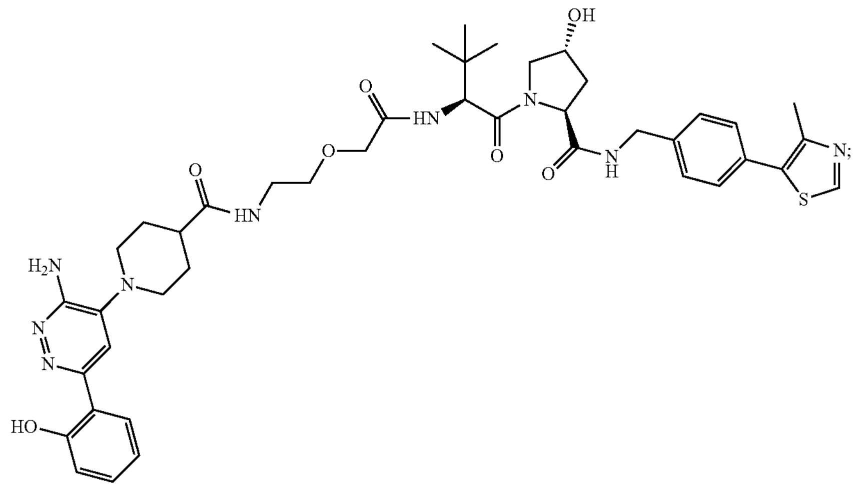 [SMILES: Cc1ncsc1-c1ccc(CNC(=O)[C@@H]2C[C@@H](O)CN2C(=O)[C@@H](NC(=O)COCCNC(=O)C2CCN(c3cc(-c4ccccc4O)nnc3N)CC2)C(C)(C)C)cc1] |
| 2. | 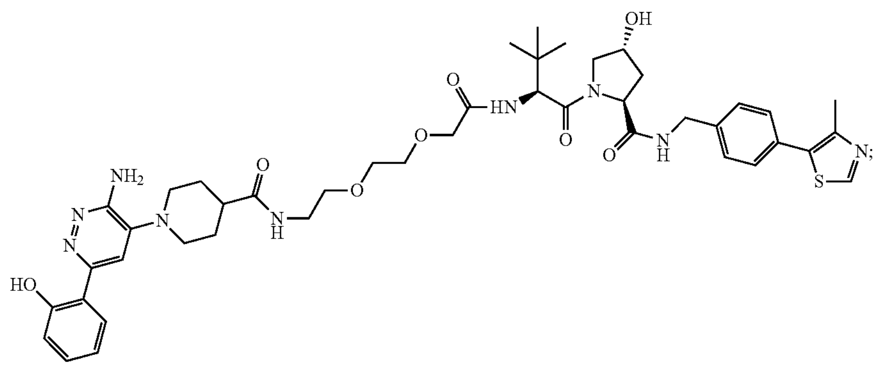 [SMILES: Cc1ncsc1-c1ccc(CNC(=O)[C@@H]2C[C@@H](O)CN2C(=O)[C@@H](NC(=O)COCCOCCNC(=O)C2CCN(c3cc(-c4ccccc4O)nnc3N)CC2)C(C)(C)C)cc1] |
| 3. | 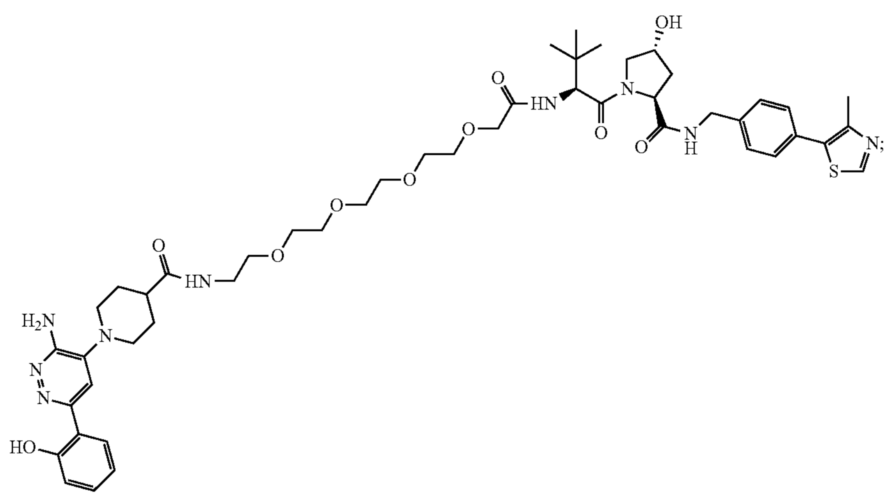 [SMILES: Cc1ncsc1-c1ccc(CNC(=O)[C@@H]2C[C@@H](O)CN2C(=O)[C@@H](NC(=O)COCCOCCOCCOCCNC(=O)C2CCN(c3cc(-c4ccccc4O)nnc3N)CC2)C(C)(C)C)cc1] |

-continued
| Compound No | Structure |
|---|---|
| 4. | 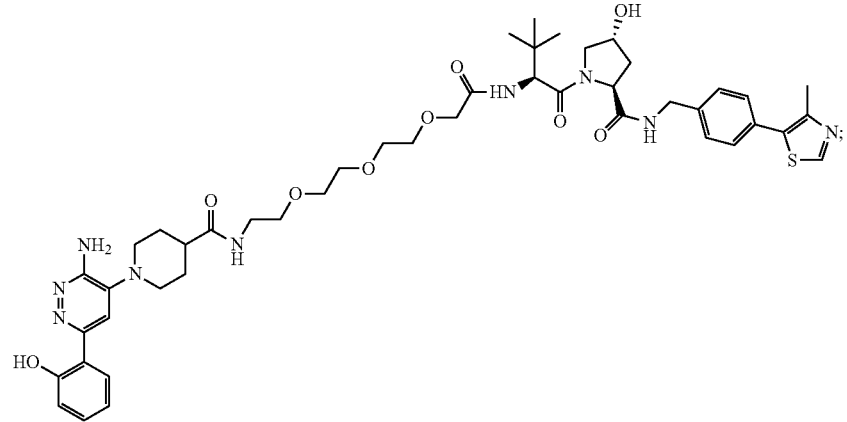 [SMILES: Cc1ncsc1-c1ccc(CNC(=O)[C@@H]2C[C@@H](O)CN2C(=O)[C@@H](NC(=O)COCCOCCOCCNC(=O)C2CCN(c3cc(-c4ccccc4O)nnc3N)CC2)C(C)(C)C)cc1] |
| 5. | 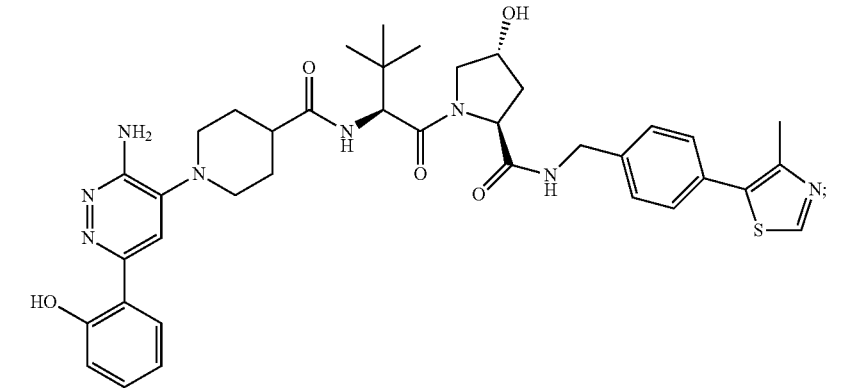 [SMILES: Cc1ncsc1-c1ccc(CNC(=O)[C@@H]2C[C@@H](O)CN2C(=O)[C@@H](NC(=O)C2CCN(c3cc(-c4ccccc4O)nnc3N)CC2)C(C)(C)C)cc1] |
| 6. | 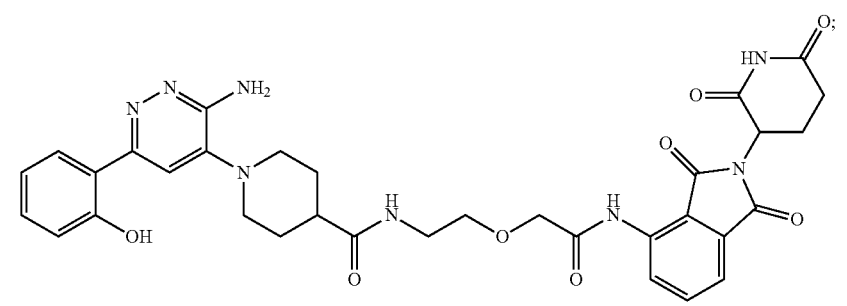 [SMILES: Nc1nnc(-c2ccccc2O)cc1N1CCC(C(=O)NCCOCC(=O)Nc2cccc3c2C(=O)N(C2CCC(=O)NC2=O)C3=O)CC1] |
| 7. | 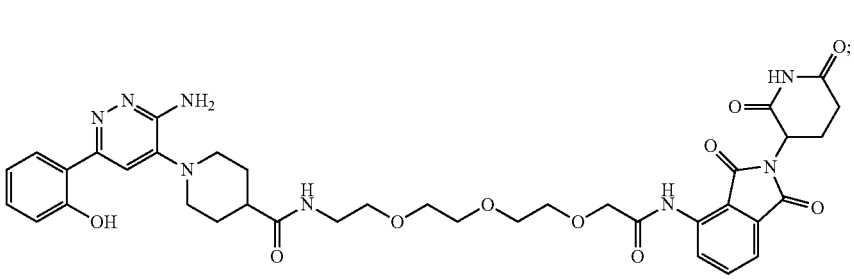 [SMILES: Nc1nnc(-c2ccccc2O)cc1N1CCC(C(=O)NCCOCCOCCOCC(=O)Nc2cccc3c2C(=O)N(C2CCC(=O)NC2=O)C3=O)CC1] |

-continued
| Compound No | Structure |
|---|---|
| 8. | 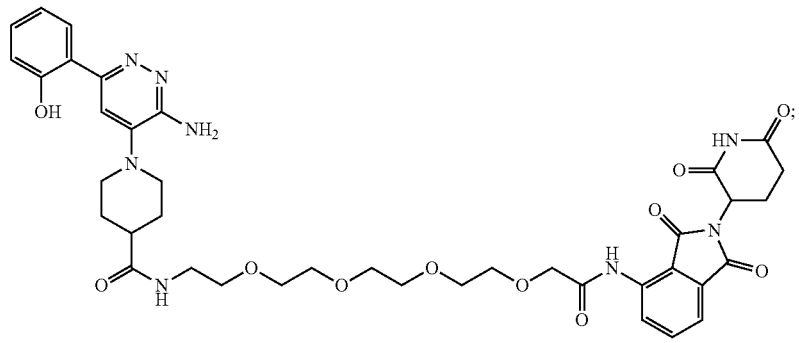 [SMILES: Nc1nnc(-c2ccccc2O)cc1N1CCC(C(=O)NCCOCCOCCOCCOCC(=O)Nc2cccc3c2C(=O)N(C2CCC(=O)NC2=O)C3=O)CC1] |
| 9. | 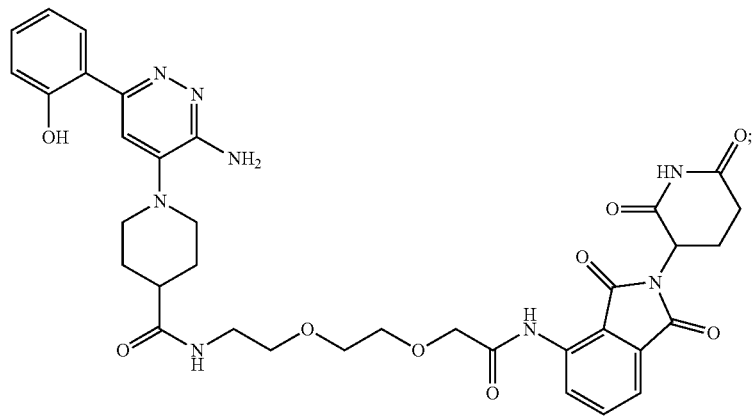 [SMILES: Nc1nnc(-c2ccccc2O)cc1N1CCC(C(=O)NCCOCCOCC(=O)Nc2cccc3c2C(=O)N(C2CCC(=O)NC2=O)C3=O)CC1] |
| 10. | 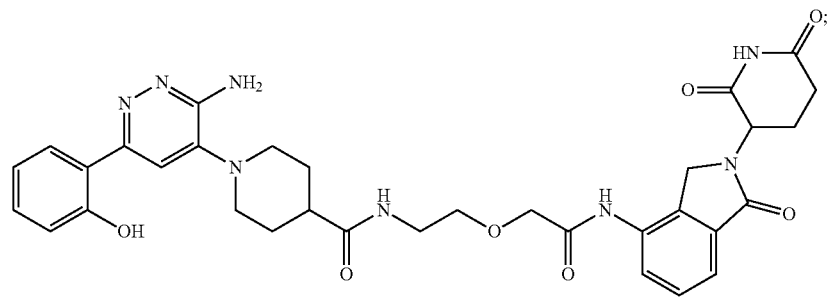 [SMILES: Nc1nnc(-c2ccccc2O)cc1N1CCC(C(=O)NCCOCC(=O)Nc2cccc3c2CN(C2CCC(=O)NC2=O)C3=O)CC1] |
| 11. | 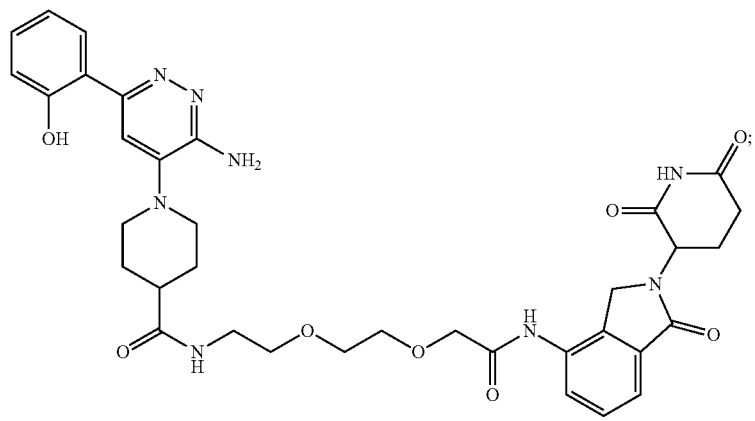 [SMILES: Nc1nnc(-c2ccccc2O)cc1N1CCC(C(=O)NCCOCCOCC(=O)Nc2cccc3c2CN(C2CCC(=O)NC2=O)C3=O)CC1] |

| Compound No | Structure |
|---|---|
| 12. | 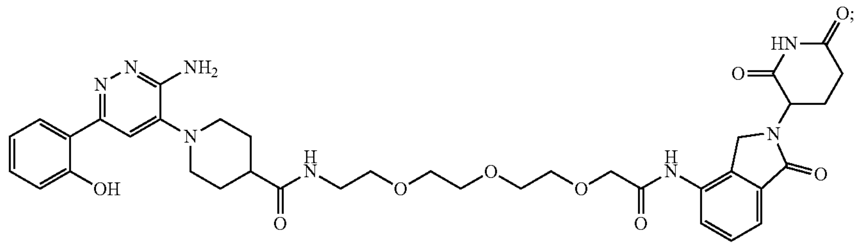 [SMILES: Nc1nnc(-c2ccccc2O)cc1N1CCC(C(=O)NCCOCCOCCOCC(=O)Nc2cccc3c2CN(C2CCC(=O)NC2=O)C3=O)CC1] |
| 13. | 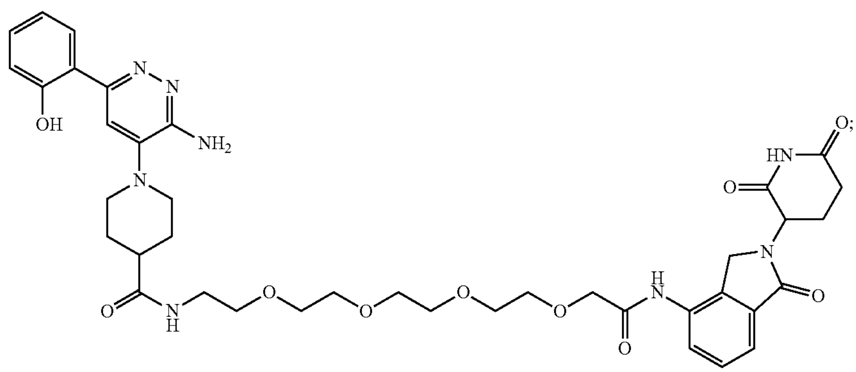 [SMILES: Nc1nnc(-c2ccccc2O)cc1N1CCC(C(=O)NCCOCCOCCOCCOCC(=O)Nc2cccc3c2CN(C2CCC(=O)NC2=O)C3=O)CC1] |
| 14. | 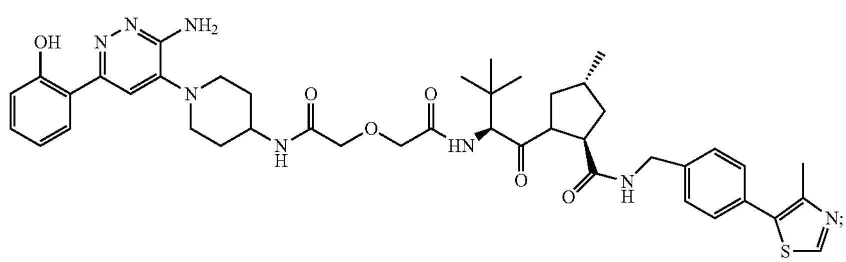 [SMILES: Cc1ncsc1-c1ccc(CNC(=O)[C@@H]2C[C@@H](C)CC2C(=O)[C@@H](NC(=O)COCC(=O)NC2CCN(c3cc(-c4ccccc4O)nnc3N)CC2)C(C)(C)C)cc1] |
| 15. | 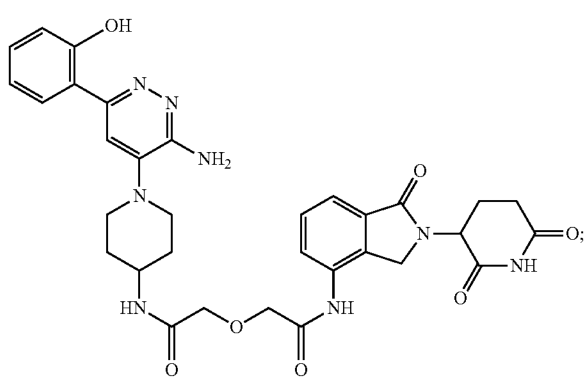 [SMILES: Nc1nnc(-c2ccccc2O)cc1N1CCC(NC(=O)COCC(=O)Nc2cccc3c2CN(C2CCC(=O)NC2=O)C3=O)CC1] |

| Compound No | Structure |
|---|---|
| 16. | (structure) |
| 17. | (structure) |
| 18. | (structure) |
| 19. | (structure) |
| 20. | (structure) |

| Compound No | Structure |
|---|---|
| 21. | 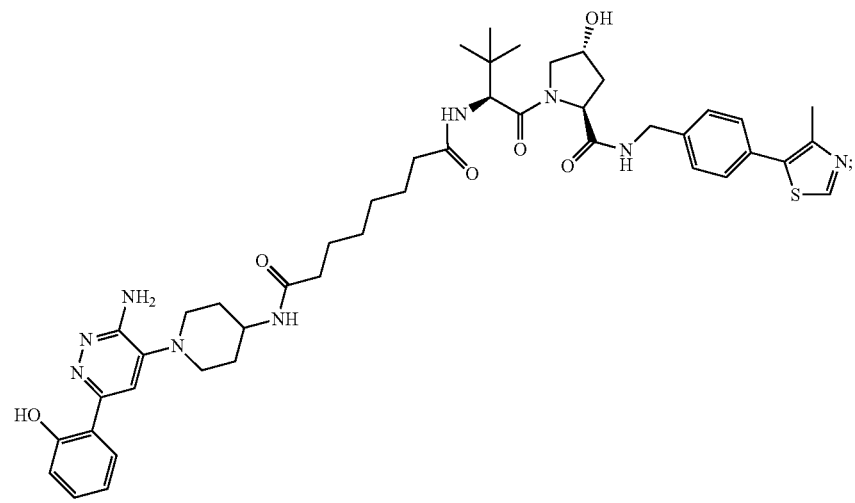 [SMILES: Cc1ncsc1-c1ccc(CNC(=O)[C@@H]2C[C@@H](O)CN2C(=O)[C@@H](NC(=O)CCCCCCC(=O)NC2CCN(c3cc(-c4ccccc4O)nnc3N)CC2)C(C)(C)C)cc1] |
| 22. | 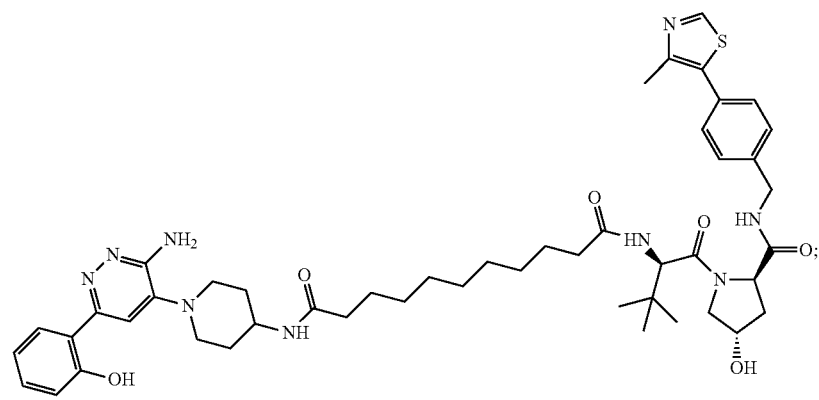 [SMILES: Cc1ncsc1-c1ccc(CNC(=O)[C@H]2C[C@H](O)CN2C(=O)[C@H](NC(=O)CCCCCCCCCC(=O)NC2CCN(c3cc(-c4ccccc4O)nnc3N)CC2)C(C)(C)C)cc1] |
| 23. | 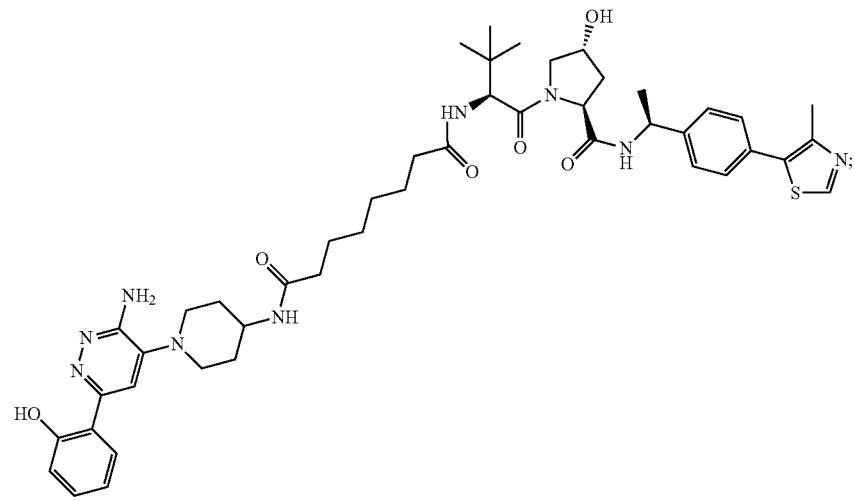 [SMILES: Cc1ncsc1-c1ccc([C@H](C)NC(=O)[C@@H]2C[C@@H](O)CN2C(=O)[C@@H](NC(=O)CCCCCCC(=O)NC2CCN(c3cc(-c4ccccc4O)nnc3N)CC2)C(C)(C)C)cc1] |

| Compound No | Structure |
|---|---|
| 24. | (chemical structure) |
| 25. | (chemical structure) |
| 26. | (chemical structure) |
| 27. | (chemical structure) |
| 28. | (chemical structure) |

| Compound No | Structure |
|---|---|
| 29. | 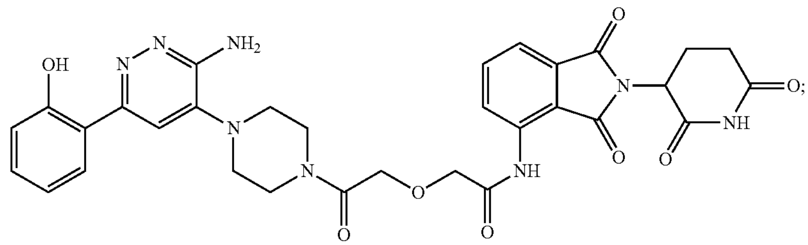 [SMILES: Nc1nnc(-c2ccccc2O)cc1N1CCN(C(=O)COCC(=O)Nc2cccc3c2C(=O)N(C2CCC(=O)NC2=O)C3=O)CC1] |
| 30. | 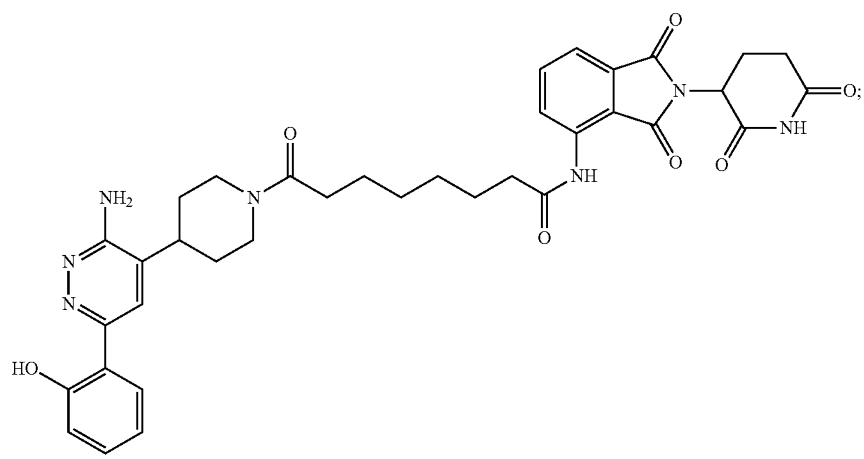 [SMILES: Nc1nnc(-c2ccccc2O)cc1C1CCN(C(=O)CCCCCCC(=O)Nc2cccc3c2C(=O)N(C2CCC(=O)NC2=O)C3=O)CC1] |
| 31. | 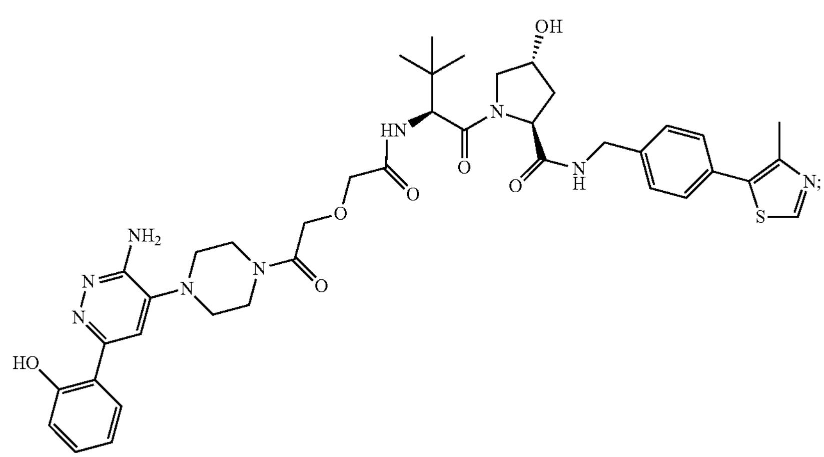 |

-continued
| Compound No | Structure |
|---|---|
| 32. | 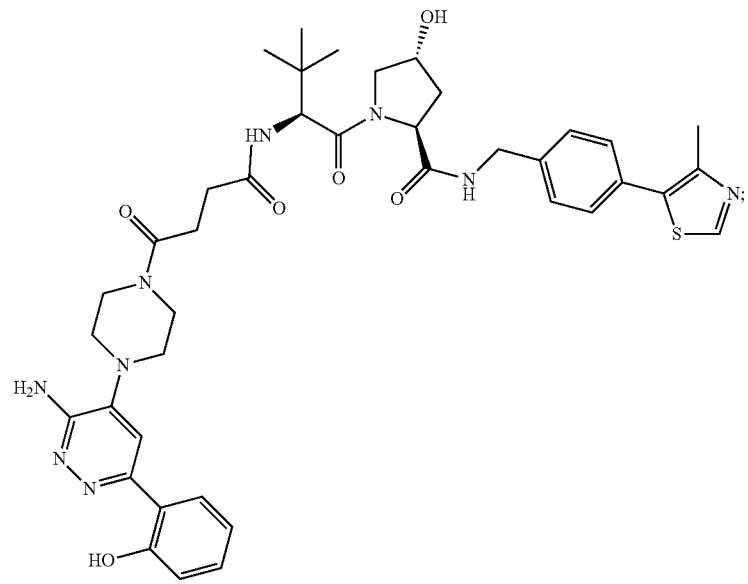 [SMILES: Cc1ncsc1-c1ccc(CNC(=O)[C@@H]2C[C@@H](O)CN2C(=O)[C@@H](NC(=O)CCC(=O)N2CCN(c3cc(-c4ccccc4O)nnc3N)CC2)C(C)(C)C)cc1] |
| 33. | 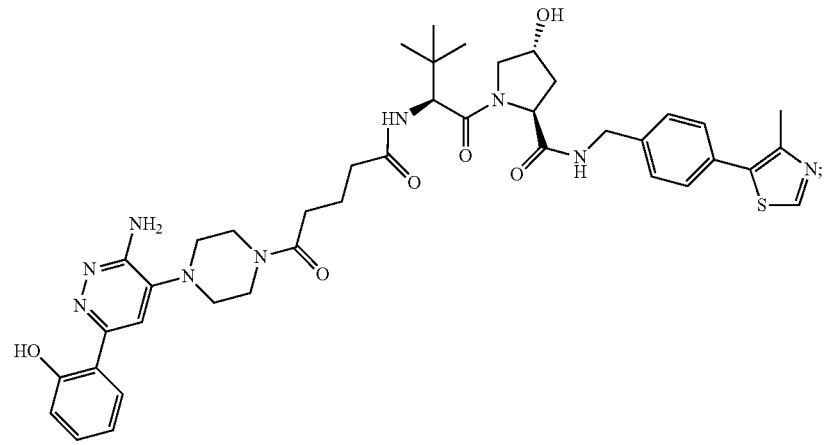 [SMILES: Cc1ncsc1-c1ccc(CNC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] |

| Compound No | Structure |
|---|---|
| 34. | 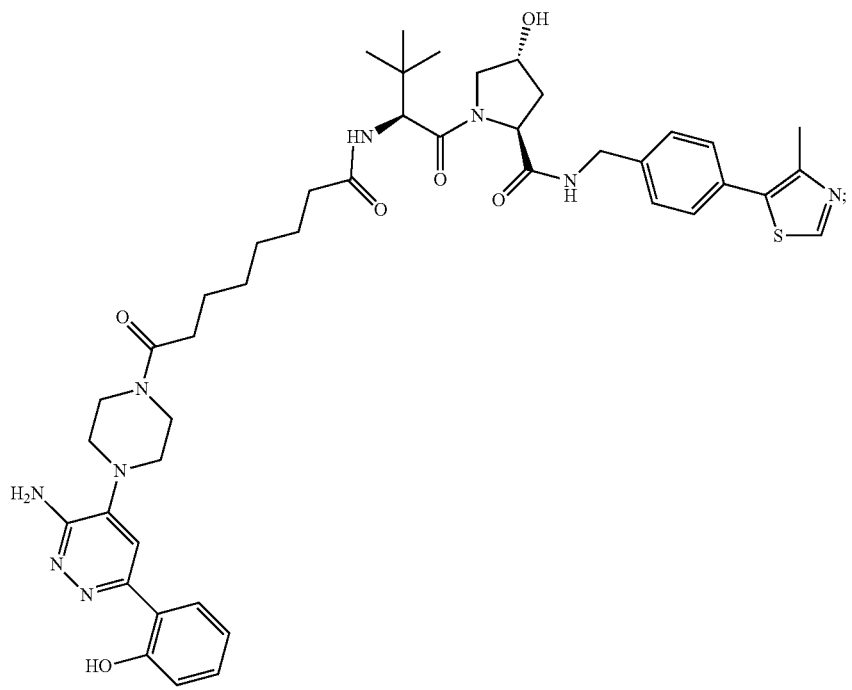 [SMILES: Cc1ncsc1-c1ccc(CNC(=O)[C@@H]2C[C@@H](O)CN2C(=O)[C@@H](NC(=O)CCCCCCC(=O)N2CCN(c3cc(-c4ccccc4O)nnc3N)CC2)C(C)(C)C)cc1] |
| 35. | 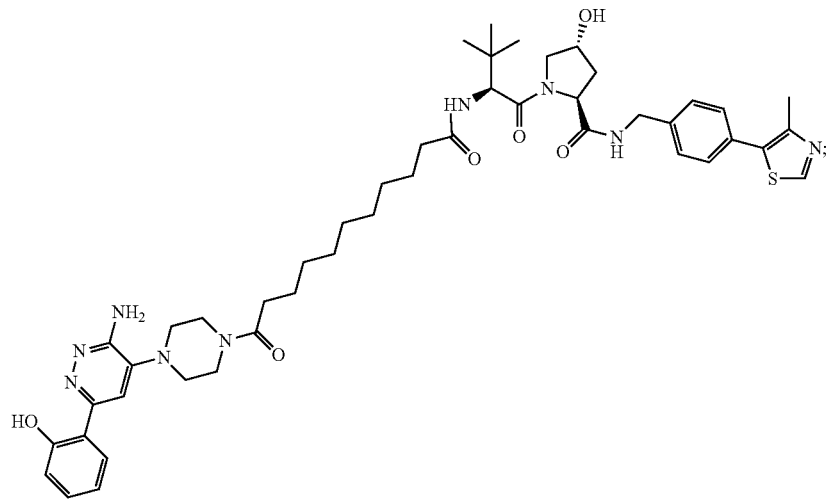 [SMILES: Cc1ncsc1-c1ccc(CNC(=O)[C@@H]2C[C@@H](O)CN2C(=O)[C@@H](NC(=O)CCCCCCCCCC(=O)N2CCN(c3cc(-c4ccccc4O)nnc3N)CC2)C(C)(C)C)cc1] |

| Compound No | Structure |
|---|---|
| 36. | 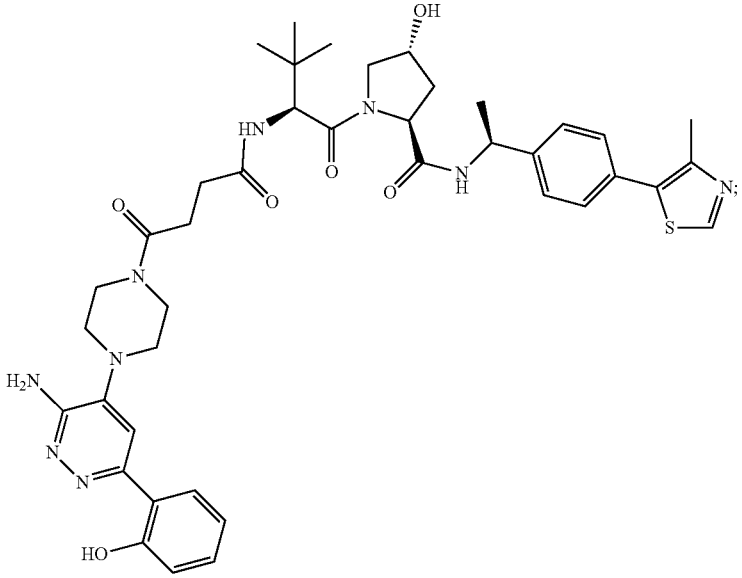 [SMILES: Cc1ncsc1-c1ccc([C@H](C)NC(=O)[C@@H]2C[C@@H](O)CN2C(=O)[C@@H](NC(=O)CCC(=O)N2CCN(c3cc(-c4ccccc4O)nnc3N)CC2)C(C)(C)C)cc1] |
| 37. | 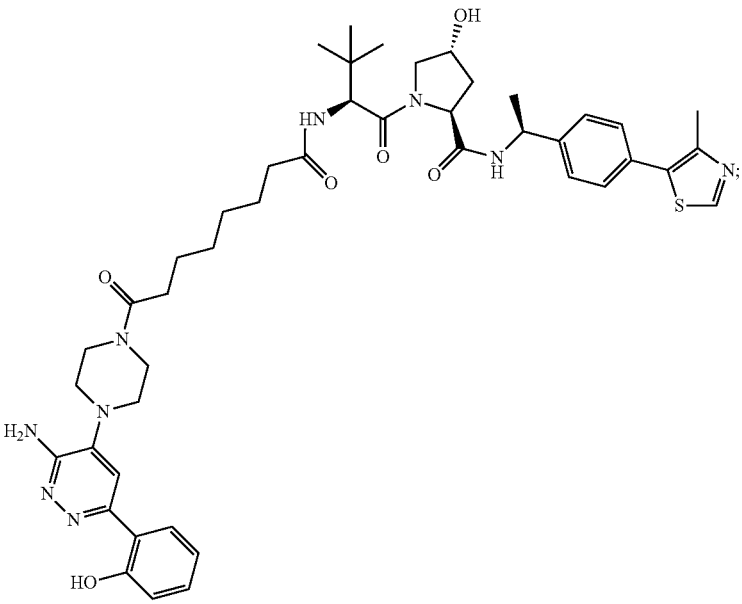 [SMILES: Cc1ncsc1-c1ccc([C@H](C)NC(=O)[C@@H]2C[C@@H](O)CN2C(=O)[C@@H](NC(=O)CCCCCCC(=O)N2CCN(c3cc(-c4ccccc4O)nnc3N)CC2)C(C)(C)C)cc1] |

-continued
| Compound No | Structure |
|---|---|
| 38. | 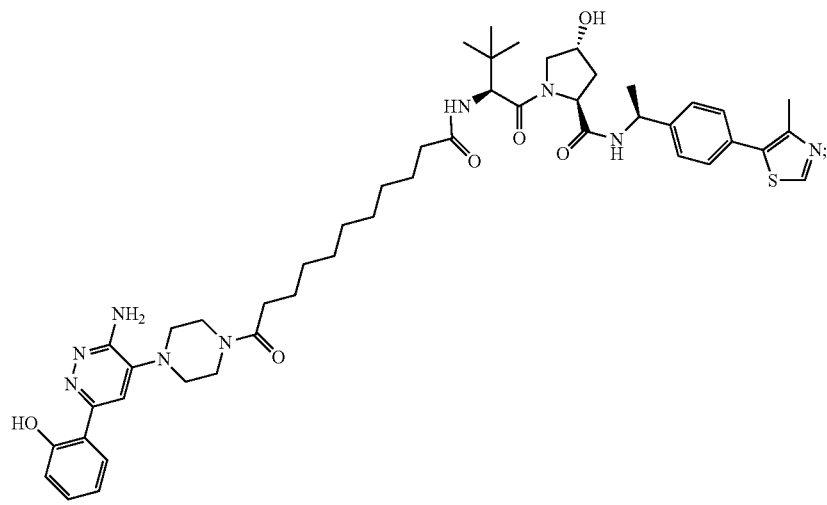 [SMILES: Cc1ncsc1-c1ccc([C@H](C)NC(=O)[C@@H]2C[C@@H](O)CN2C(=O)[C@@H](NC(=O)CCCCCCCCCC(=O)N2CCN(c3cc(-c4ccccc4O)nnc3N)CC2)C(C)(C)C)cc1] |
| 39. | 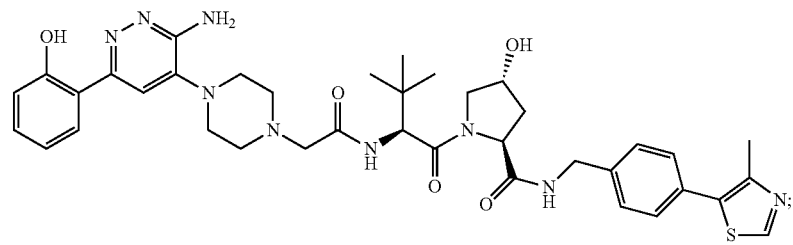 [SMILES: Cc1ncsc1-c1ccc(CNC(=O)[C@@H]2C[C@@H](O)CN2C(=O)[C@@H](NC(=O)CN2CCN(c3cc(-c4ccccc4O)nnc3N)CC2)C(C)(C)C)cc1] |
| 40. | 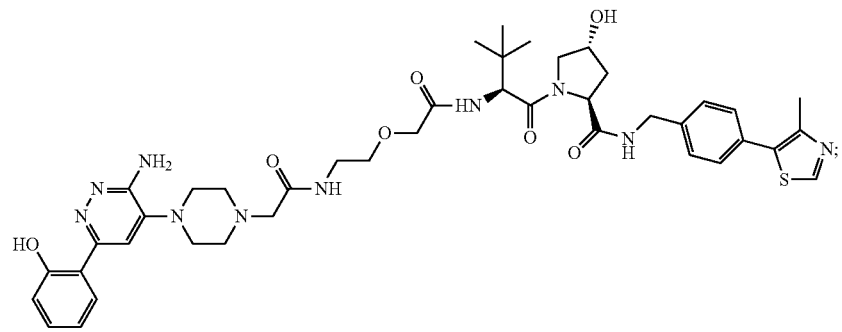 [SMILES: Cc1ncsc1-c1ccc(CNC(=O)[C@@H]2C[C@@H](O)CN2C(=O)[C@@H](NC(=O)COCCNC(=O)CN2CCN(c3cc(-c4ccccc4O)nnc3N)CC2)C(C)(C)C)cc1] |
| 41. | 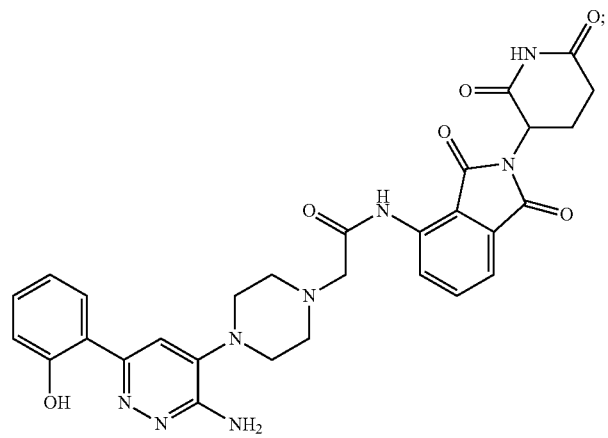 [SMILES: Nc1nnc(-c2ccccc2O)cc1N1CCN(CC(=O)Nc2cccc3c2C(=O)N(C2CCC(=O)NC2=O)C3=O)CC1] |

| Compound No | Structure |
|---|---|
| 42. | 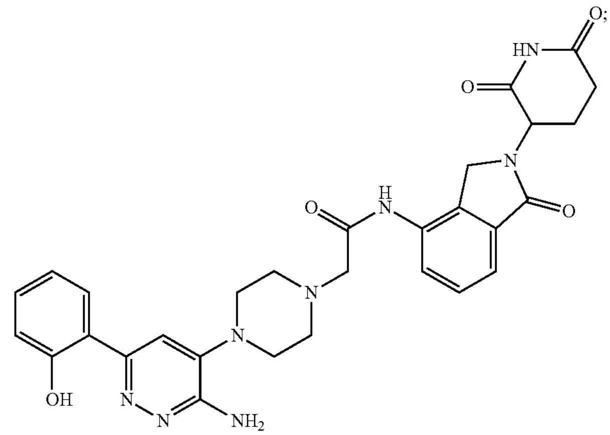 [SMILES: Nc1nnc(-c2ccccc2O)cc1N1CCN(CC(=O)Nc2cccc3c2CN(C2CCC(=O)NC2=O)C3=O)CC1] |
| 43. | 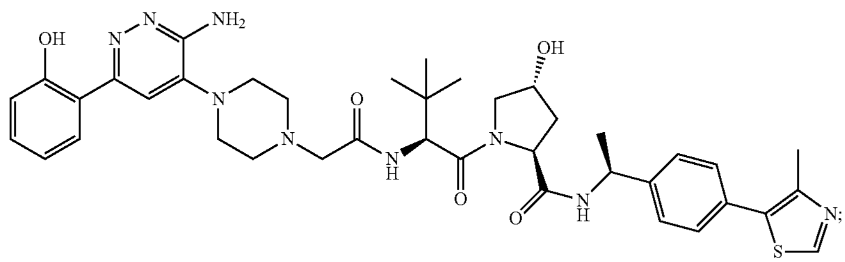 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)(C)C)cc1] |
| 44. | 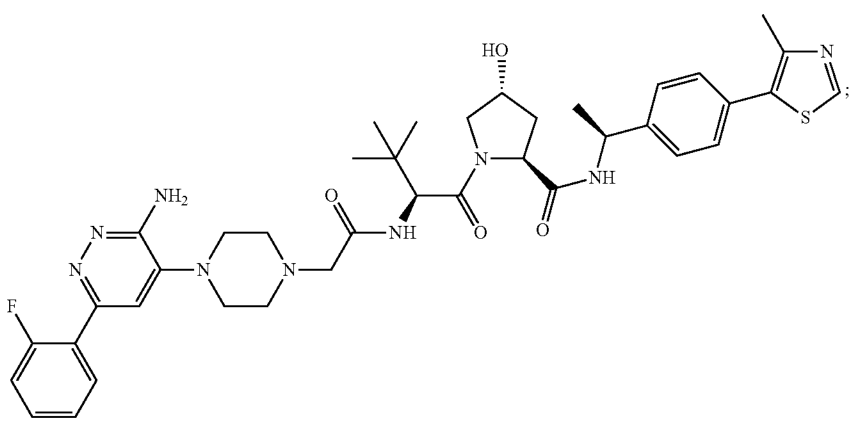 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4F)nnc3N)CC2)C(C)(C)C)cc1] |
| 45. | 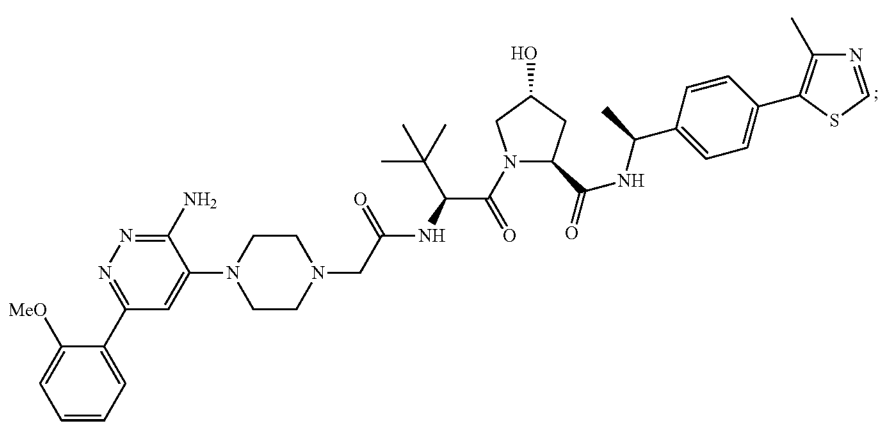 [SMILES: COc1ccccc1-c1cc(N2CCN(CC(=O)N[C@H](C(=O)N3C[C@H](O)C[C@H]3C(=O)N[C@@H](C)c3ccc(-c4scnc4C)cc3)C(C)(C)C)CC2)c(N)nn1] |

-continued
| Compound No | Structure |
|---|---|
| 46. | 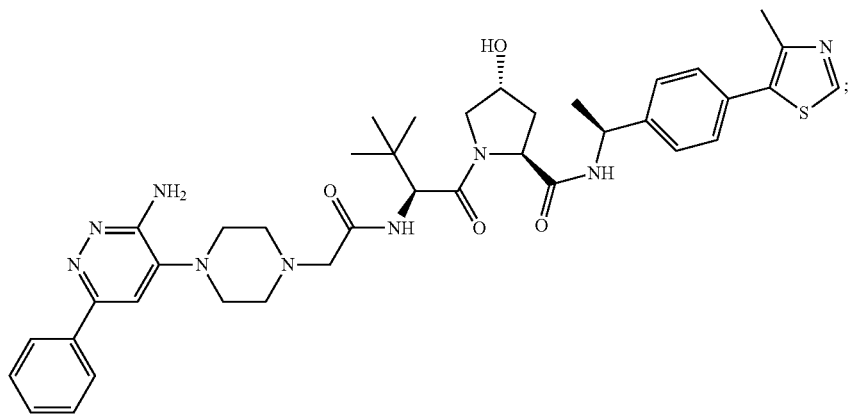 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4)nnc3N)CC2)C(C)(C)C)cc1] |
| 47 | 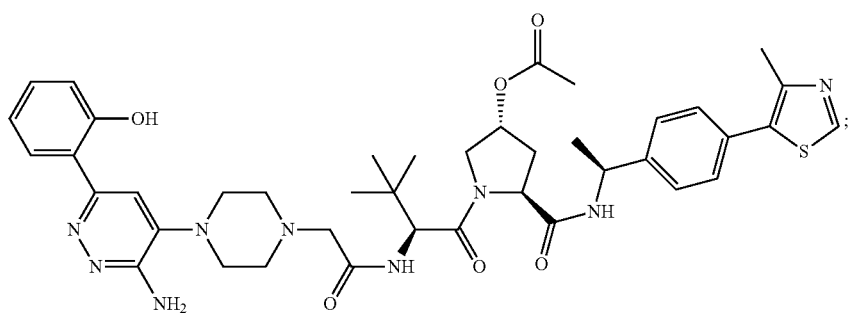 [SMILES: CC(=O)O[C@@H]1C[C@@H](C(=O)N[C@@H](C)c2ccc(-c3scnc3C)cc2)N(C(=O)[C@@H](NC(=O)CN2CCN(c3cc(-c4ccccc4O)nnc3N)CC2)C(C)(C)C)C1] |
| 48. | 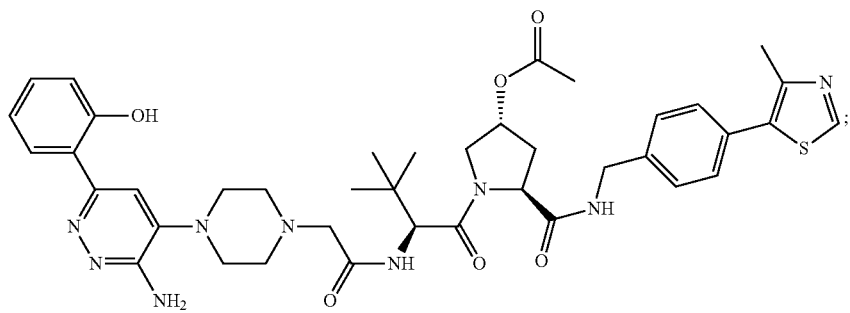 [SMILES: CC(=O)O[C@@H]1C[C@@H](C(=O)NCc2ccc(-c3scnc3C)cc2)N(C(=O)[C@@H](NC(=O)CN2CCN(c3cc(-c4ccccc4O)nnc3N)CC2)C(C)(C)C)C1] |

| Compound No | Structure |
|---|---|
| 49. | 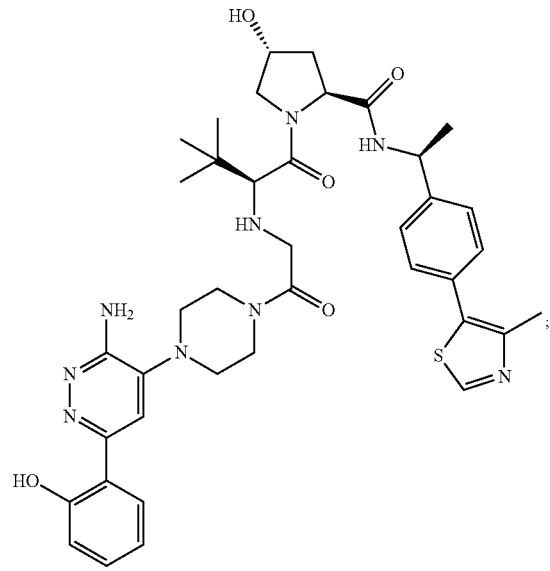 |
| 50. | 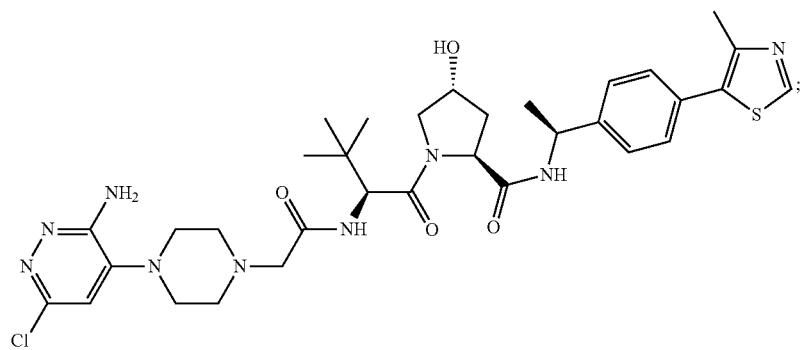 [SMILES: Cc1ncsc1-c1ccc([C@H](C)NC(=O)[C@@H]2C[C@@H](O)CN2C(=O)[C@@H](NC(=O)CN2CCN(c3cc(Cl)nnc3N)CC2)C(C)(C)C)cc1] |
| 51. | 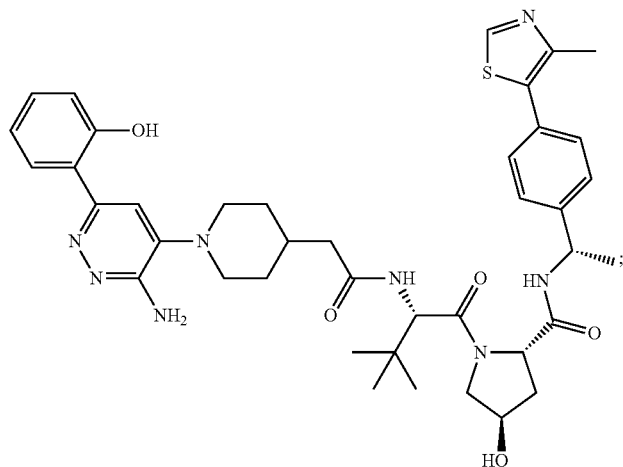 [SMILES: Cc1ncsc1-c1ccc([C@H](C)NC(=O)[C@@H]2C[C@@H](O)CN2C(=O)[C@@H](NC(=O)CC2CCN(c3cc(-c4ccccc4O)nnc3N)CC2)C(C)(C)C)cc1] |

| Compound No | Structure |
|---|---|
| 52. | 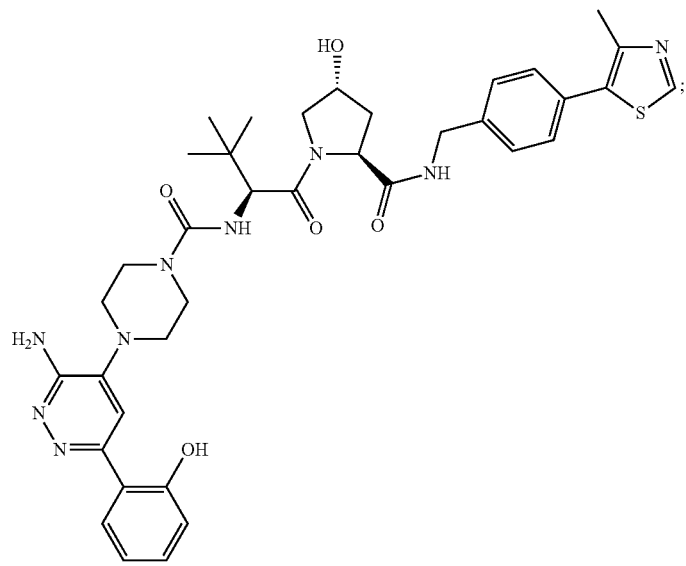 [SMILES: Cc1ncsc1-c1ccc(CNC(=O)[C@@H]2C[C@@H](O)CN2C(=O)[C@@H](NC(=O)N2CCN(c3cc(-c4ccccc4O)nnc3N)CC2)C(C)(C)C)cc1] |
| 53. | 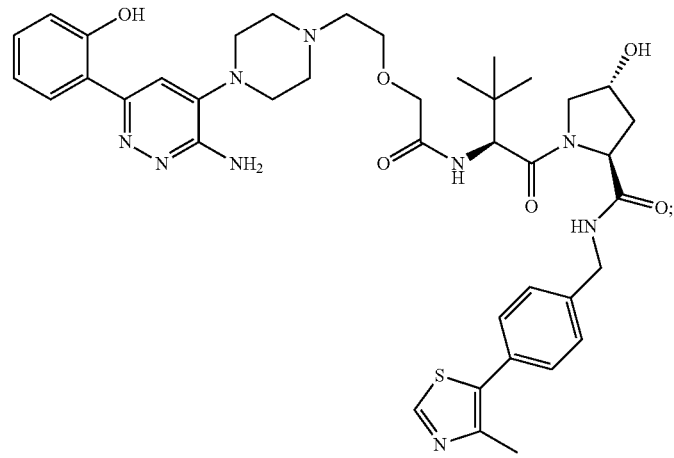 [SMILES: Cc1ncsc1-c1ccc(CNC(=O)[C@@H]2C[C@@H](O)CN2C(=O)[C@@H](NC(=O)COCCN2CCN(c3cc(-c4ccccc4O)nnc3N)CC2)C(C)(C)C)cc1] |
| 54. | 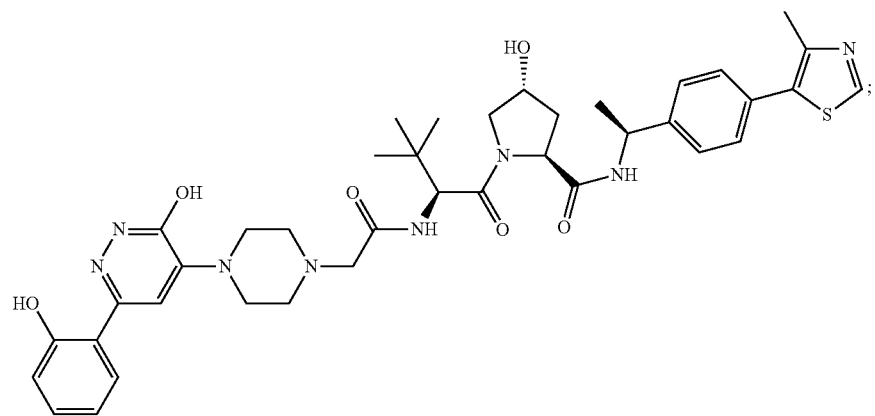 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3O)CC2)C(C)(C)C)cc1] |

-continued
| Compound No | Structure |
|---|---|
| 55. | 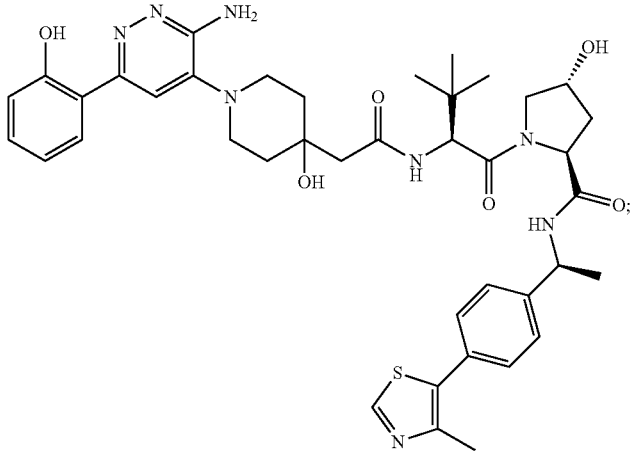 [SMILES: Cc1ncsc1-c1ccc([C@H](C)NC(=O)[C@@H]2C[C@@H](O)CN2C(=O)[C@@H](NC(=O)CC2(O)CCN(c3cc(-c4ccccc4O)nnc3N)CC2)C(C)(C)C)cc1] |
| 56. | 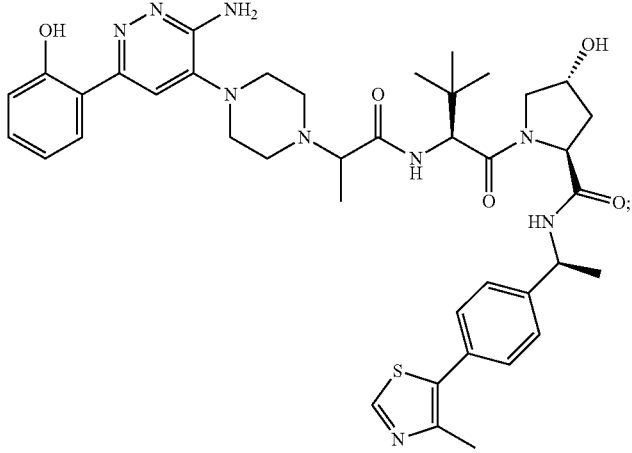 [SMILES: Cc1ncsc1-c1ccc([C@H](C)NC(=O)[C@@H]2C[C@@H](O)CN2C(=O)[C@@H](NC(=O)C(C)N2CCN(c3cc(-c4ccccc4O)nnc3N)CC2)C(C)(C)C)cc1] |
| 57. and 58. | 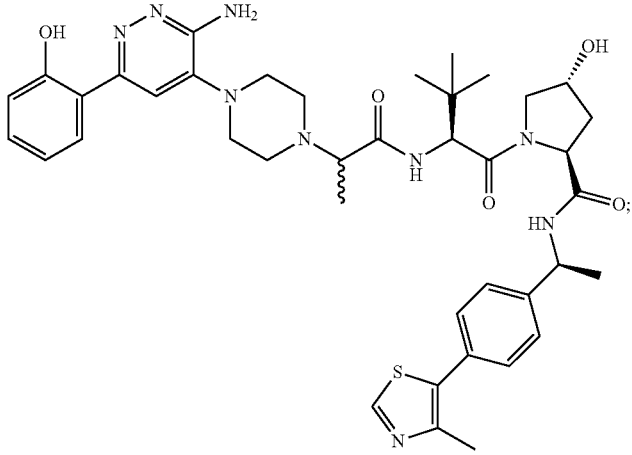<br>Isomer-1 and Isomer-2 |

| Compound No | Structure |
|---|---|
| 59. | 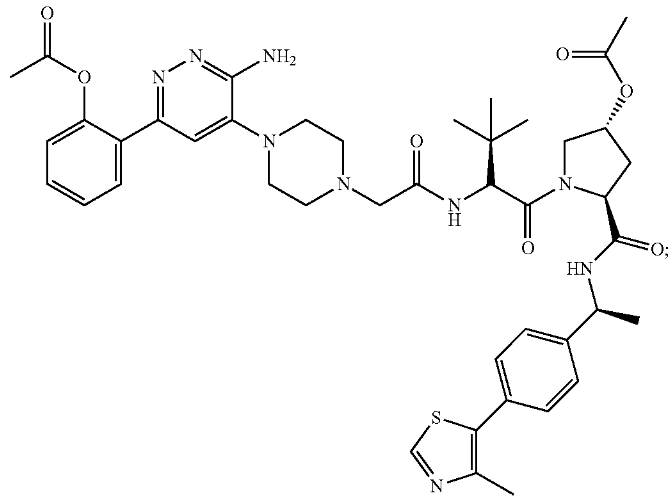 |
| 60. | 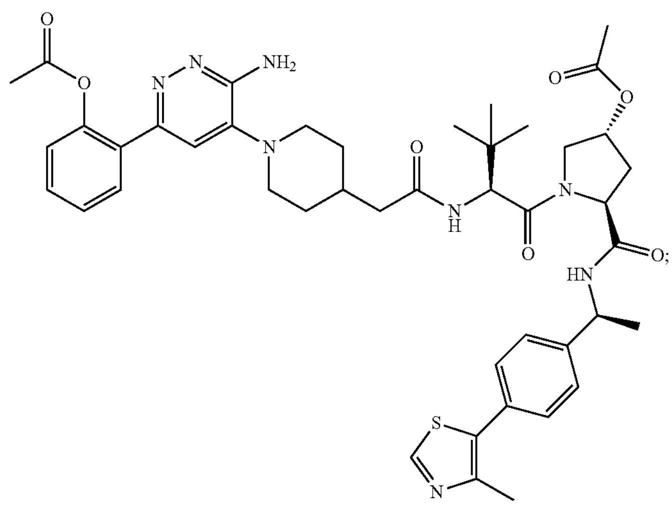 [SMILES: CC(=O)Oc1ccccc1-c1cc(N2CCC(CC(=O)N[C@H](C(=O)N3C[C@H](OC(C)=O)C[C@H]3C(=O)N[C@@H](C)c3ccc(-c4scnc4C)cc3)C(C)(C)C)CC2)c(N)nn1] |
| 61. | 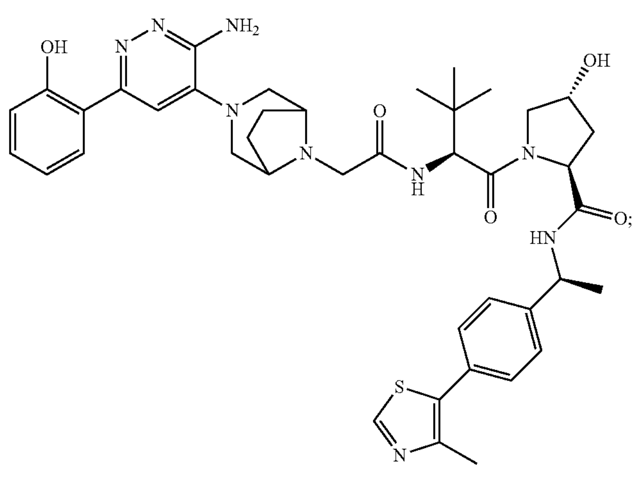 [SMILES: Cc1ncsc1-c1ccc([C@H](C)NC(=O)[C@@H]2C[C@@H](O)CN2C(=O)[C@@H](NC(=O)CN2C3CCC2CN(c2cc(-c4ccccc4O)nnc2N)C3)C(C)(C)C)cc1] |

-continued

| Compound No | Structure |
|---|---|
| 62. | 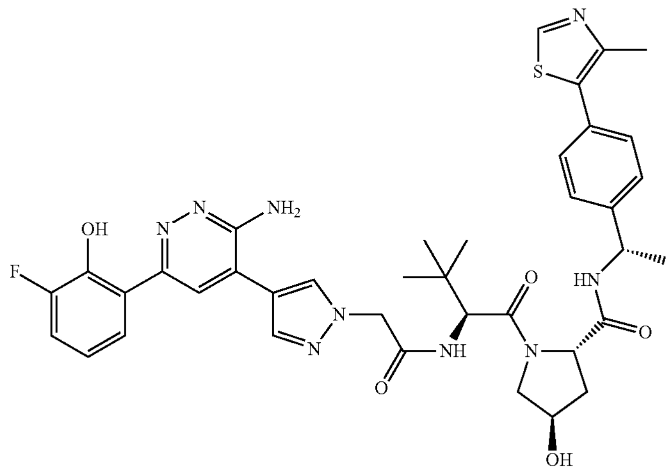 |
| 63. | 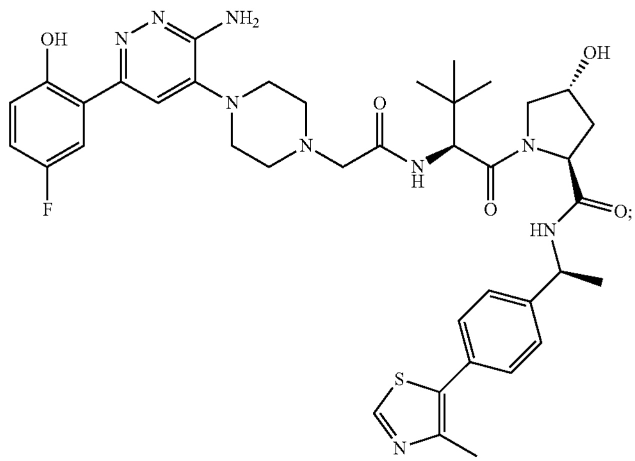 [SMILES: Cc1ncsc1-c1ccc([C@H](C)NC(=O)[C@@H]2C[C@@H](O)CN2C(=O)[C@@H](NC(=O)CN2CCN(c3cc(-c4cc(F)ccc4O)nnc3N)CC2)C(C)(C)C)cc1] |
| 64. | 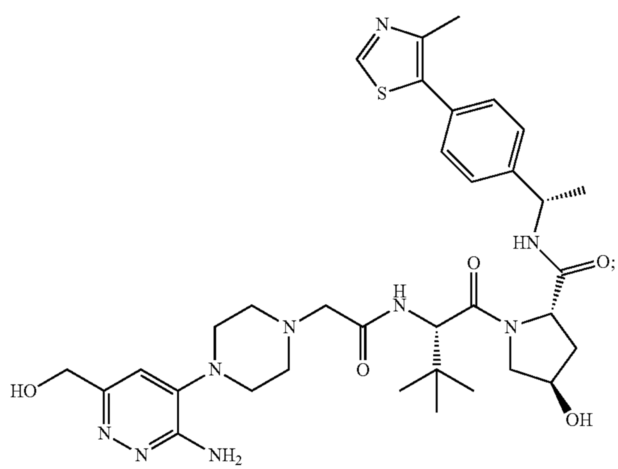 [SMILES: Cc1ncsc1-c1ccc([C@H](C)NC(=O)[C@@H]2C[C@@H](O)CN2C(=O)[C@@H](NC(=O)CN2CCN(c3cc(CO)nnc3N)CC2)C(C)(C)C)cc1] |

-continued

| Compound No | Structure |
|---|---|
| 65. | (chemical structure) |
| 66. | (chemical structure) |
| 67. | (chemical structure) |

| Compound No | Structure |
|---|---|
| 68. | 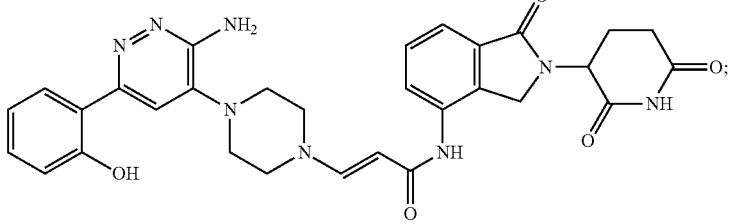 |
| 69. | 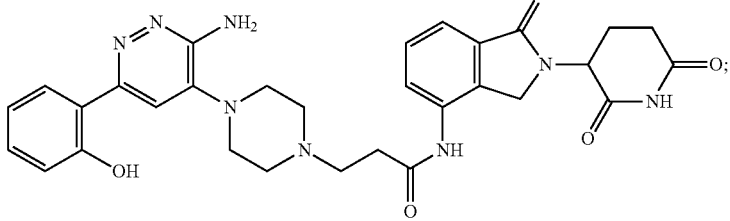 |
| 70. | 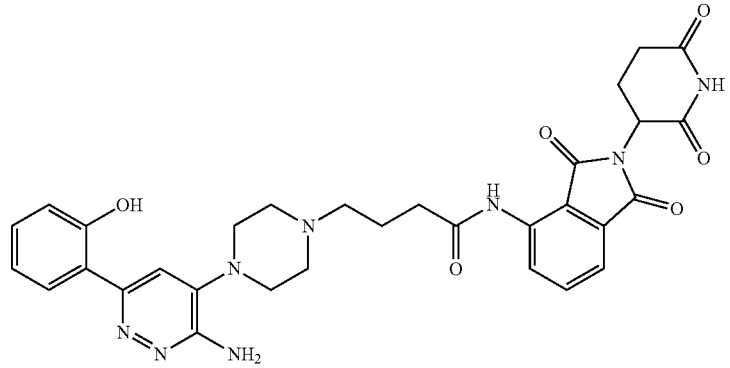 [SMILES: Nc1nnc(-c2ccccc2O)cc1N1CCN(CCCC(=O)Nc2cccc3c2C(=O)N(C2CCC(=O)NC2=O)C3=O)CC1] |
| 71. | 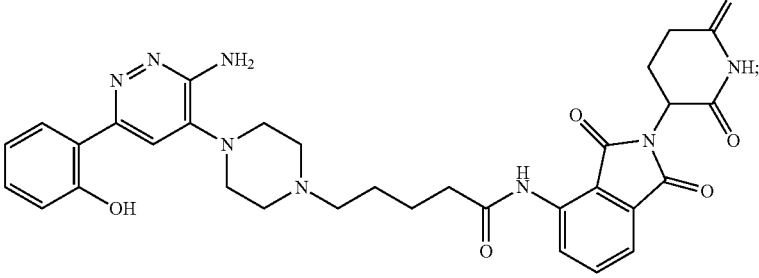 |

| Compound No | Structure |
|---|---|
| 72. | 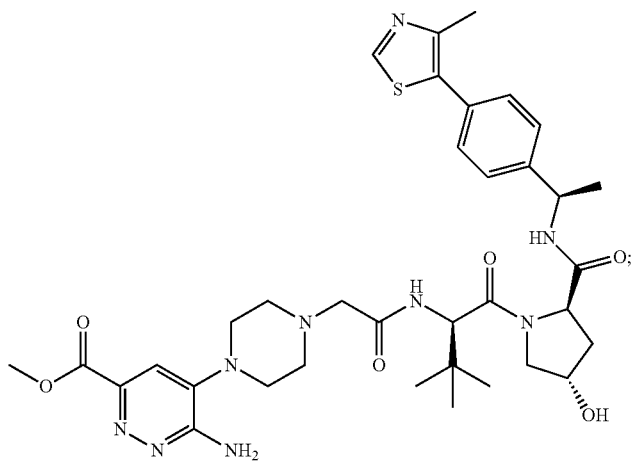 [SMILES: COC(=O)c1cc(N2CCN(CC(=O)N[C@@H](C(=O)N3C[C@@H](O)C[C@@H]3C(=O)N[C@H](C)c3ccc(-c4scnc4C)cc3)C(C)(C)C)CC2)c(N)nn1] |
| 73. | 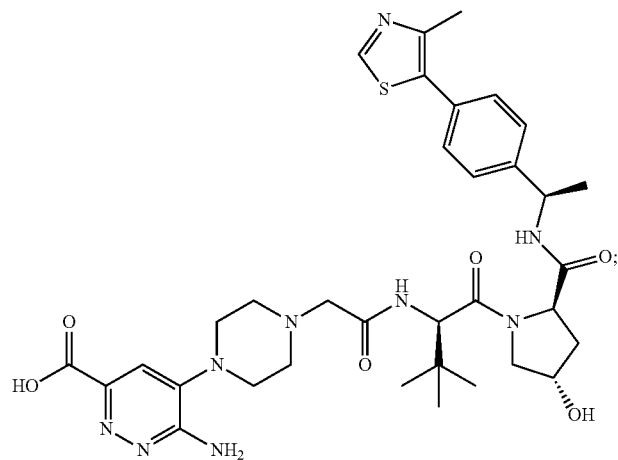 [SMILES: Cc1ncsc1-c1ccc([C@@H](C)NC(=O)[C@H]2C[C@H](O)CN2C(=O)[C@H](NC(=O)CN2CCN(c3cc(C(=O)O)nnc3N)CC2)C(C)(C)C)cc1] |
| 74. | 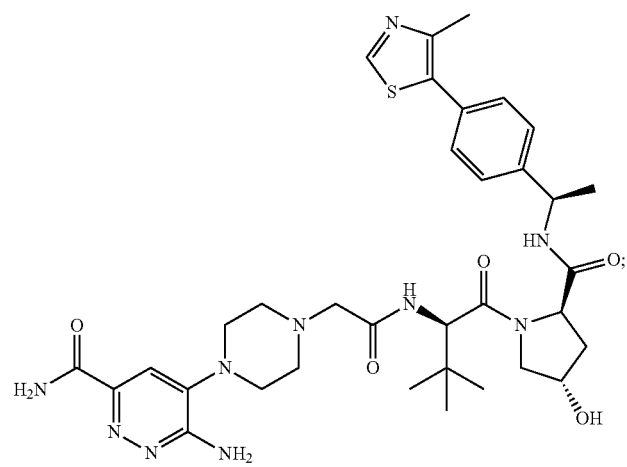 [SMILES: Cc1ncsc1-c1ccc([C@@H](C)NC(=O)[C@H]2C[C@H](O)CN2C(=O)[C@H](NC(=O)CN2CCN(c3cc(C(N)=O)nnc3N)CC2)C(C)(C)C)cc1] |

| Compound No | Structure |
|---|---|
| 75. | (chemical structure) |
| 76. | (chemical structure) |
| 77. and 78. | (chemical structure) Isomer-1 and Isomer-2 |

-continued
| Compound No | Structure |
|---|---|
| 79. | 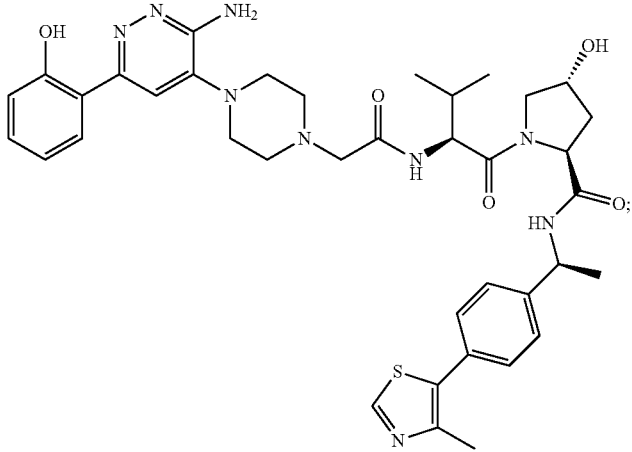 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)C)cc1] |
| 80. | 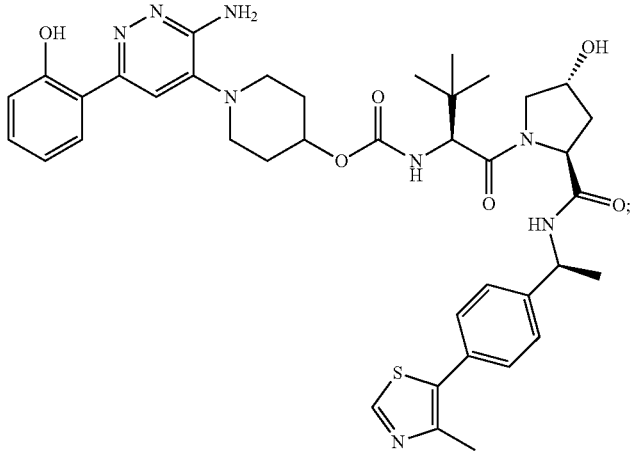 [SMILES: Cc1ncsc1-c1ccc([C@H](C)NC(=O)[C@@H]2C[C@@H](O)CN2C(=O)[C@@H](NC(=O)OC2CCN(c3cc(-c4ccccc4O)nnc3N)CC2)C(C)(C)C)cc1] |
| 81. | 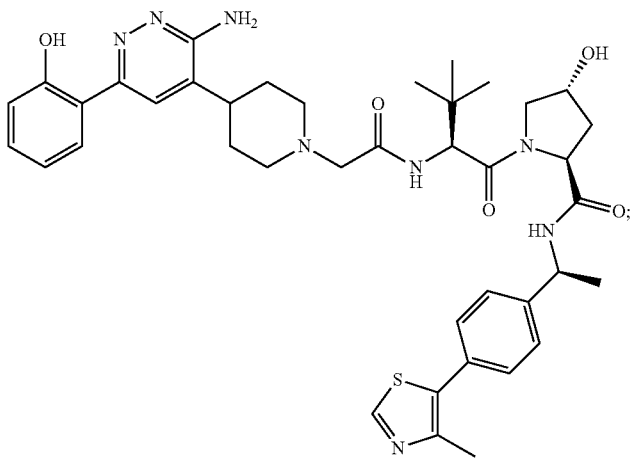 [SMILES: Cc1ncsc1-c1ccc([C@H](C)NC(=O)[C@@H]2C[C@@H](O)CN2C(=O)[C@@H](NC(=O)CN2CCC(c3cc(-c4ccccc4O)nnc3N)CC2)C(C)(C)C)cc1] |

-continued
| Compound No | Structure |
|---|---|
| 82. | 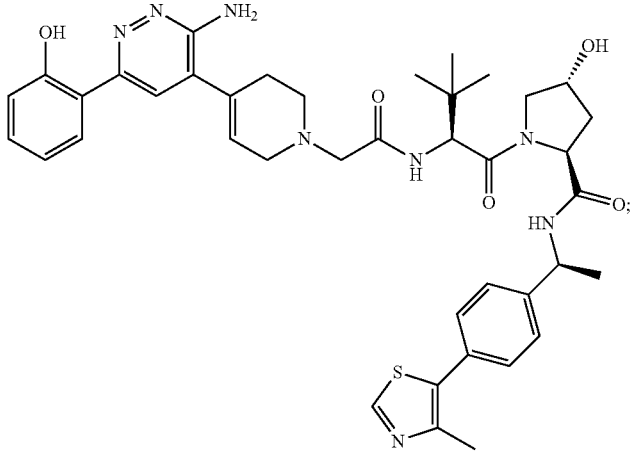 [SMILES: Cc1ncsc1-c1ccc([C@H](C)NC(=O)[C@@H]2C[C@@H](O)CN2C(=O)[C@@H](NC(=O)CN2CC=C(c3cc(-c4ccccc4O)nnc3N)CC2)C(C)(C)C)cc1] |
| 83. and 84. | 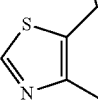
Isomer-1 and Isomer-2 |
| 85. | 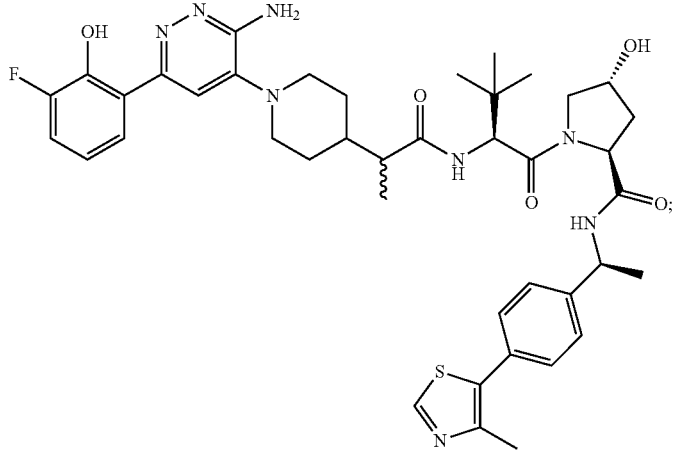 |

-continued

| Compound No | Structure |
|---|---|
| 86. | 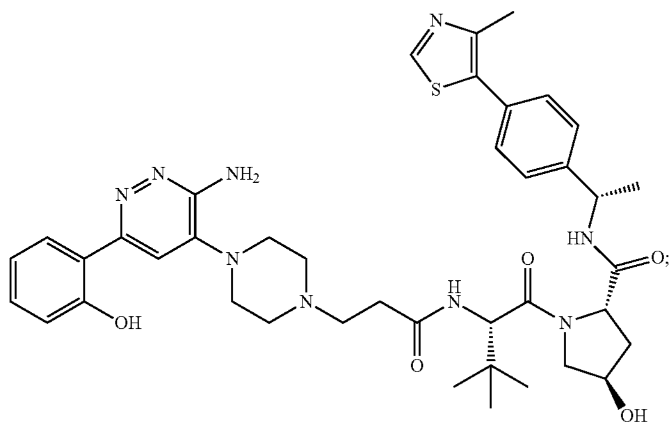 [SMILES: Cc1ncsc1-c1ccc([C@H](C)NC(=O)[C@@H]2C[C@@H](O)CN2C(=O)[C@@H](NC(=O)CCN2CCN(c3cc(-c4ccccc4O)nnc3N)CC2)C(C)(C)C)cc1] |
| 87. | 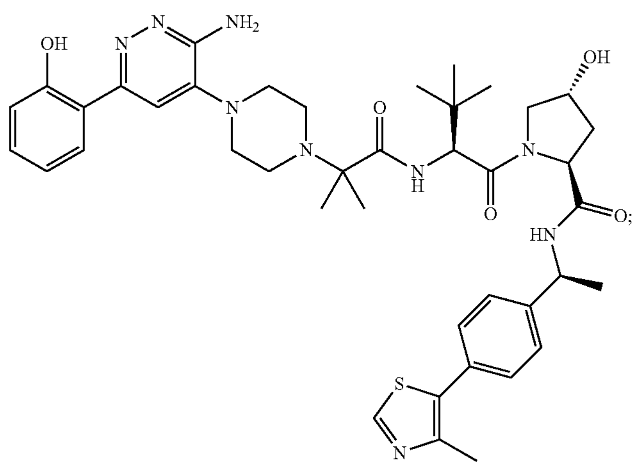 [SMILES: Cc1ncsc1-c1ccc([C@H](C)NC(=O)[C@@H]2C[C@@H](O)CN2C(=O)[C@@H](NC(=O)C(C)(C)N2CCN(c3cc(-c4ccccc4O)nnc3N)CC2)C(C)(C)C)cc1] |
| 88. | 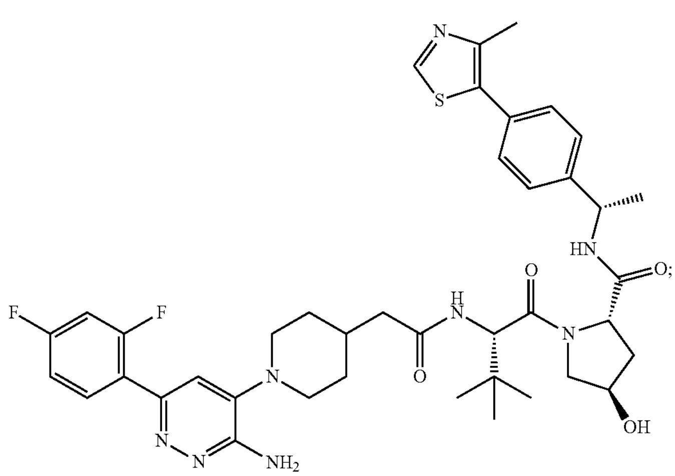 [SMILES: Cc1ncsc1-c1ccc([C@H](C)NC(=O)[C@@H]2C[C@@H](O)CN2C(=O)[C@@H](NC(=O)CC2CCN(c3cc(-c4ccc(F)cc4F)nnc3N)CC2)C(C)(C)C)cc1] |

| Compound No | Structure |
|---|---|
| 89. | 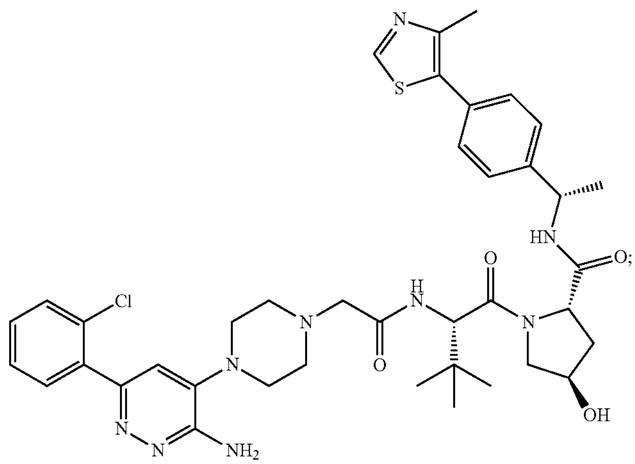 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4Cl)nnc3N)CC2)C(C)(C)C)cc1] |
| 90. | 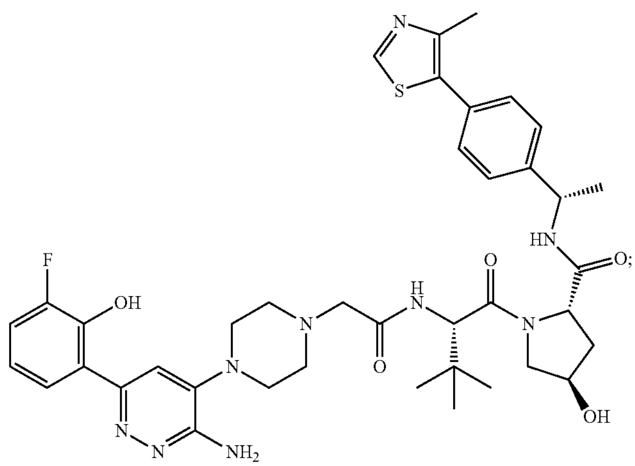 |
| 91. | 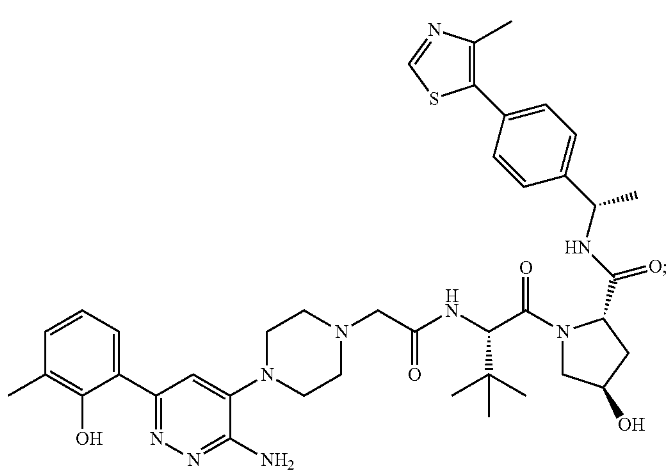 [SMILES: Cc1cccc(-c2cc(N3CCN(CC(=O)N[C@H](C(=O)N4C[C@H](O)C[C@H]4C(=O)N[C@@H](C)c4ccc(-c5scnc5C)cc4)C(C)(C)C)CC3)c(N)nn2)c1O] |

| Compound No | Structure |
|---|---|
| 92. | 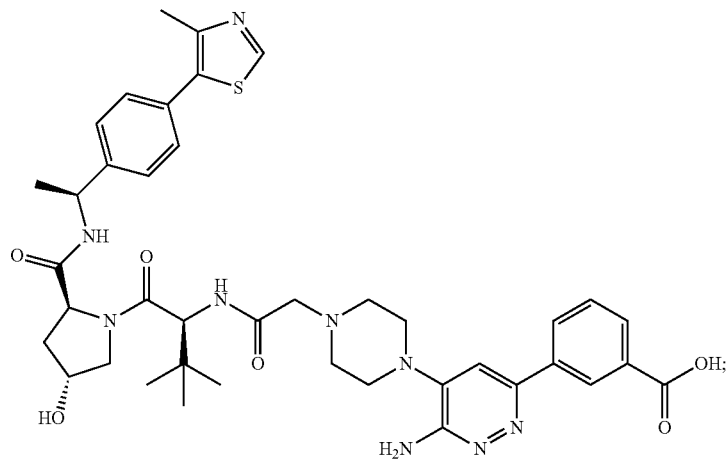 [SMILES: Cc1ncsc1-c1ccc([C@H](C)NC(=O)[C@@H]2C[C@@H](O)CN2C(=O)[C@@H](NC(=O)CN2CCN(c3cc(-c4cccc(C(=O)O)c4)nnc3N)CC2)C(C)(C)C)cc1] |
| 93. | 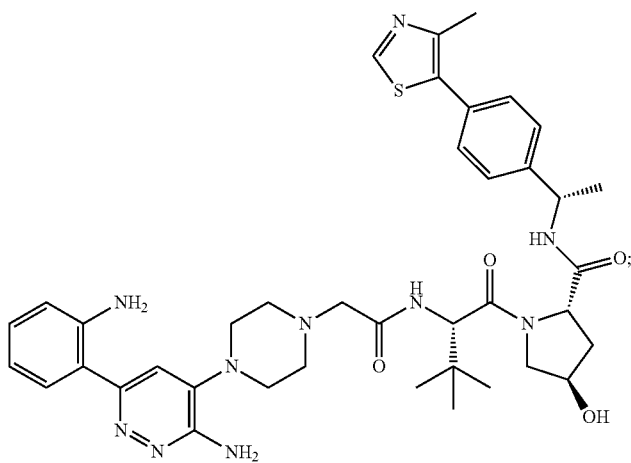 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4N)nnc3N)CC2)C(C)(C)C)cc1] |
| 94. | 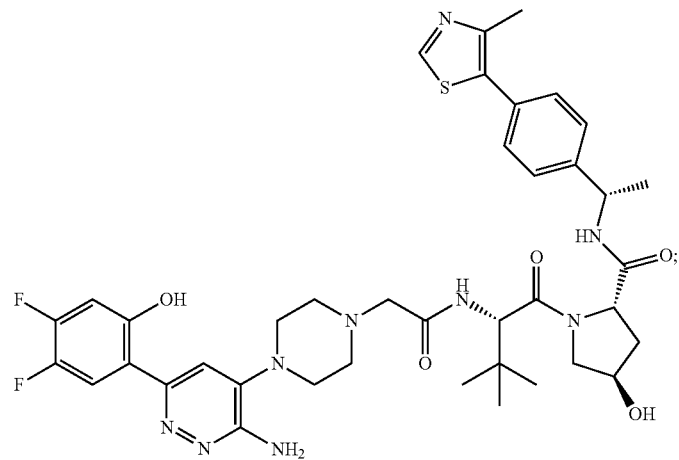 [SMILES: Cc1ncsc1-c1ccc([C@H](C)NC(=O)[C@@H]2C[C@@H](O)CN2C(=O)[C@@H](NC(=O)CN2CCN(c3cc(-c4cc(F)c(F)cc4O)nnc3N)CC2)C(C)(C)C)cc1] |

-continued

| Compound No | Structure |
|---|---|
| 95. | 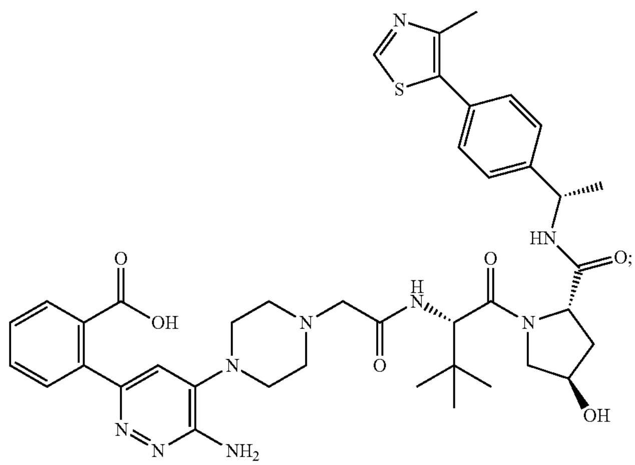 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4C(=O)O)nnc3N)CC2)C(C)(C)C)cc1] |
| 96. | 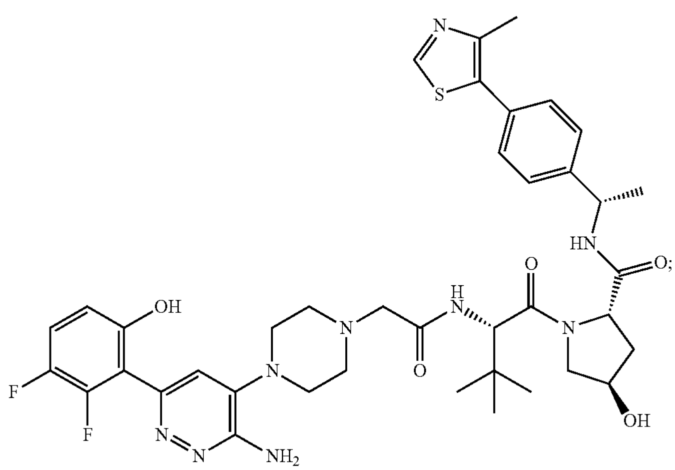 [SMILES: Cc1ncsc1-c1ccc([C@H](C)NC(=O)[C@@H]2C[C@@H](O)CN2C(=O)[C@@H](NC(=O)CN2CCN(c3cc(-c4c(O)ccc(F)c4F)nnc3N)CC2)C(C)(C)C)cc1] |
| 97. | 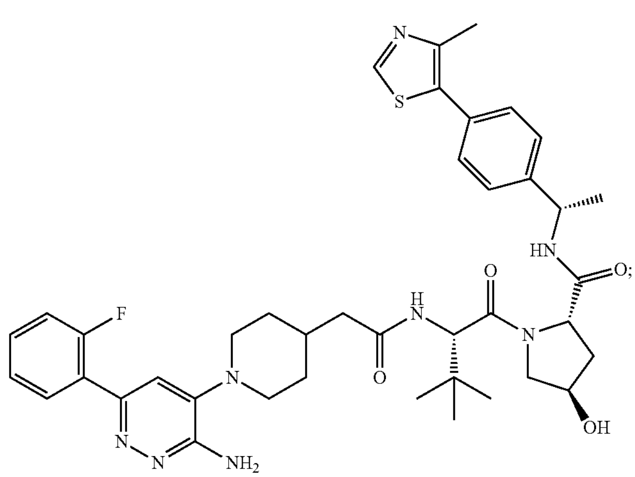 [SMILES: Cc1ncsc1-c1ccc([C@H](C)NC(=O)[C@@H]2C[C@@H](O)CN2C(=O)[C@@H](NC(=O)CC2CCN(c3cc(-c4ccccc4F)nnc3N)CC2)C(C)(C)C)cc1] |

| Compound No | Structure |
|---|---|
| 98. | 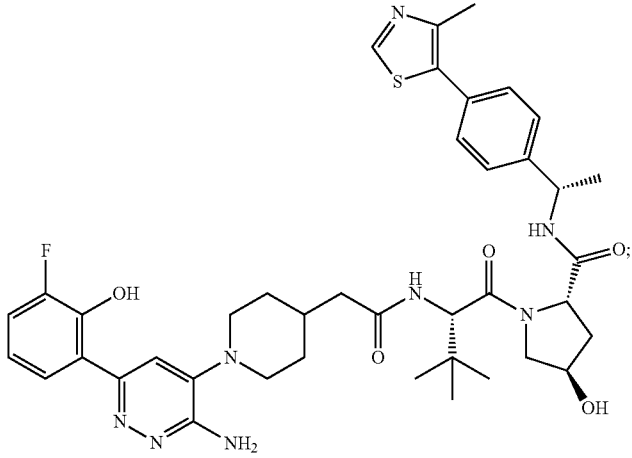 [SMILES: Cc1ncsc1-c1ccc([C@H](C)NC(=O)[C@@H]2C[C@@H](O)CN2C(=O)[C@@H](NC(=O)CC2CCN(c3cc(-c4cccc(F)c4O)nnc3N)CC2)C(C)(C)C)cc1] |
| 99. | 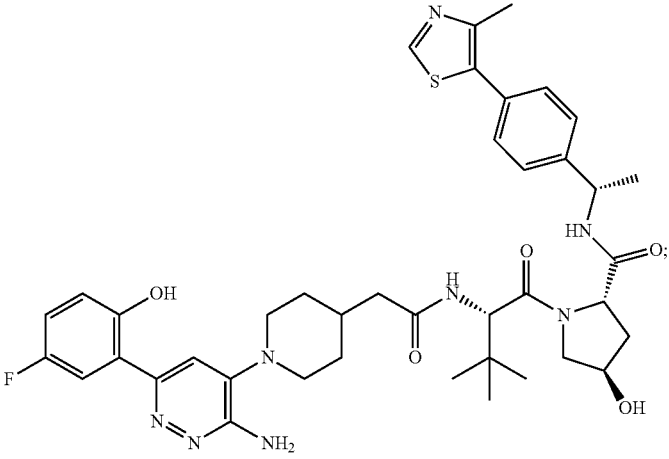 |
| 100. | 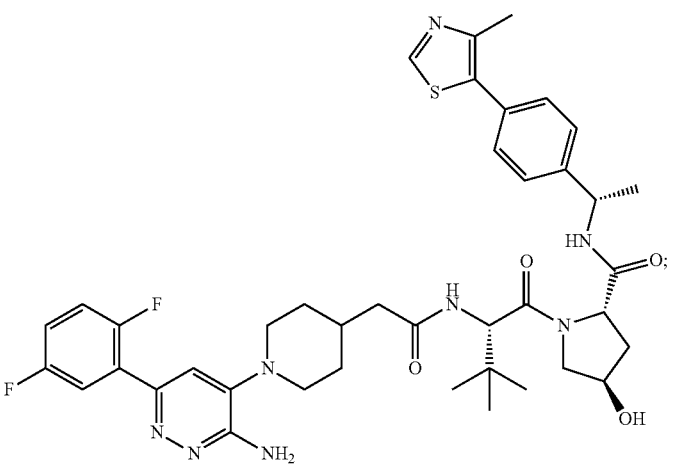 [SMILES: Cc1ncsc1-c1ccc([C@H](C)NC(=O)[C@@H]2C[C@@H](O)CN2C(=O)[C@@H](NC(=O)CC2CCN(c3cc(-c4cc(F)ccc4F)nnc3N)CC2)C(C)(C)C)cc1] |

| Compound No | Structure |
|---|---|
| 101. | 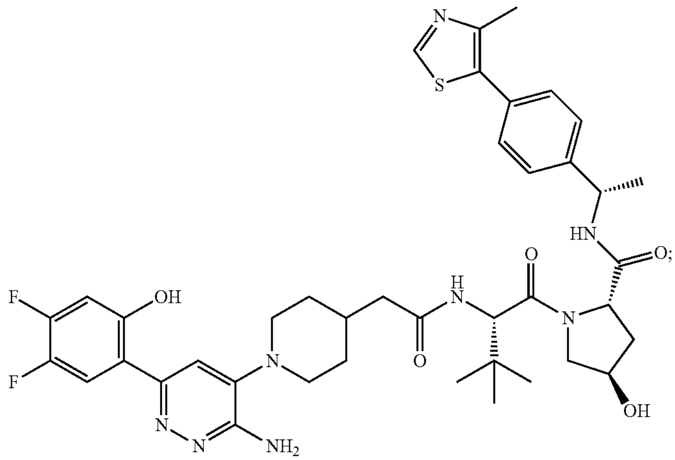 [SMILES: Cc1ncsc1-c1ccc([C@H](C)NC(=O)[C@@H]2C[C@@H](O)CN2C(=O)[C@@H](NC(=O)CC2CCN(c3cc(-c4cc(F)c(F)cc4O)nnc3N)CC2)C(C)(C)C)cc1] |
| 102. | 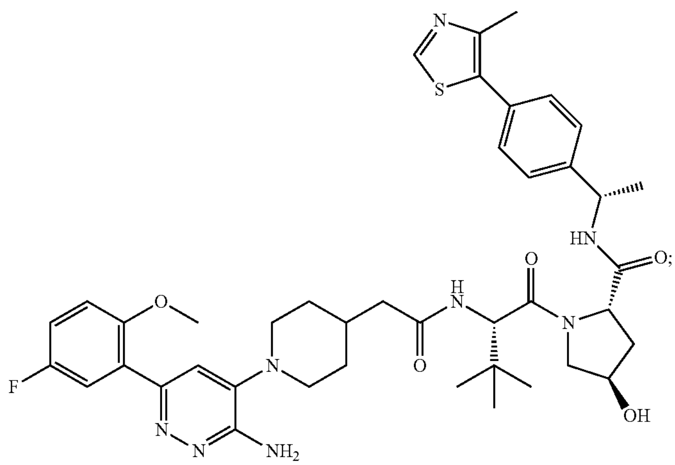 [SMILES: COc1ccc(F)cc1-c1cc(N2CCC(CC(=O)N[C@H](C(=O)N3C[C@H](O)C[C@H]3C(=O)N[C@@H](C)c3ccc(-c4scnc4C)cc3)C(C)(C)C)CC2)c(N)nn1] |
| 103. | 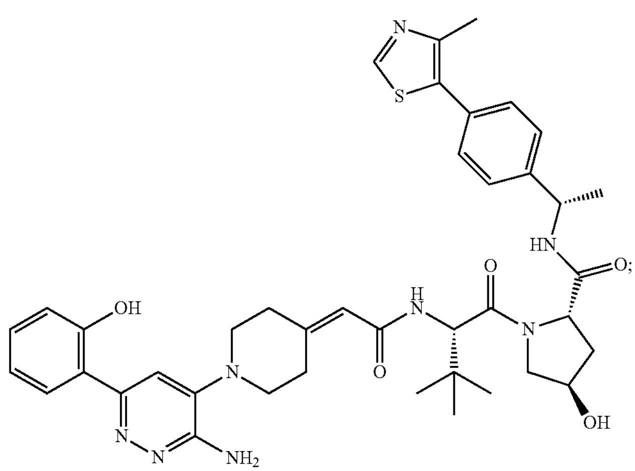 [SMILES: Cc1ncsc1-c1ccc([C@H](C)NC(=O)[C@@H]2C[C@@H](O)CN2C(=O)[C@@H](NC(=O)C=C2CCN(c3cc(-c4ccccc4O)nnc3N)CC2)C(C)(C)C)cc1] |

| Compound No | Structure |
|---|---|
| 104. | 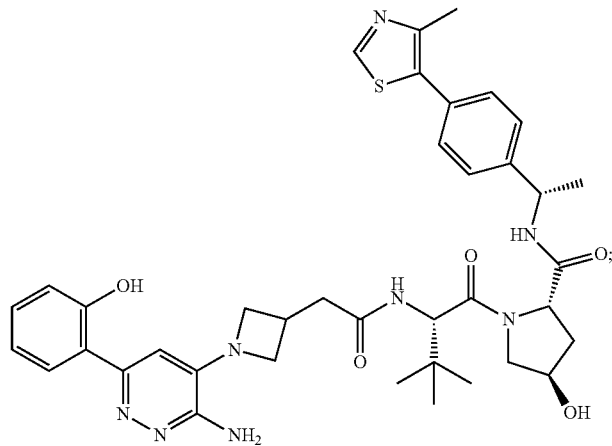 [SMILES: Cc1ncsc1-c1ccc([C@H](C)NC(=O)[C@@H]2C[C@@H](O)CN2C(=O)[C@@H](NC(=O)CC2CN(c3cc(-c4ccccc4O)nnc3N)C2)C(C)(C)C)cc1] |
| 105. | 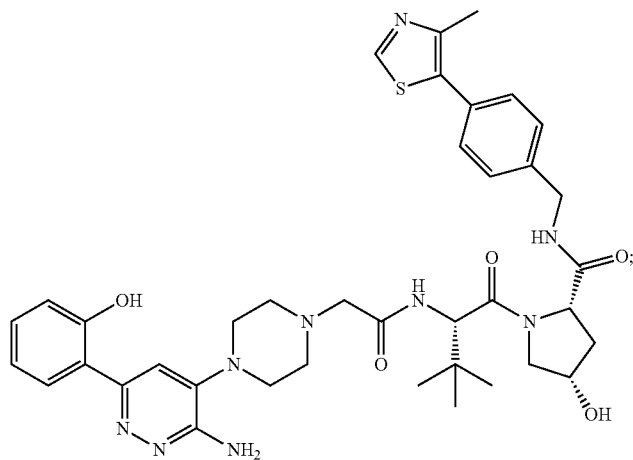 [SMILES: Cc1ncsc1-c1ccc(CNC(=O)[C@@H]2C[C@H](O)CN2C(=O)[C@@H](NC(=O)CN2CCN(c3cc(-c4ccccc4O)nnc3N)CC2)C(C)(C)C)cc1] |
| 106. | 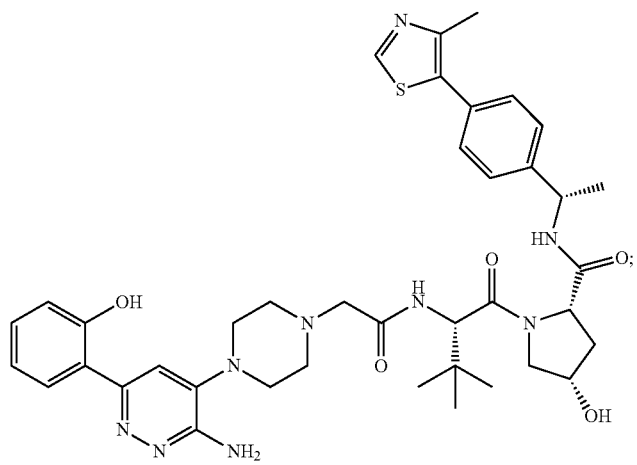 [SMILES: Cc1ncsc1-c1ccc([C@H](C)NC(=O)[C@@H]2C[C@H](O)CN2C(=O)[C@@H](NC(=O)CN2CCN(c3cc(-c4ccccc4O)nnc3N)CC2)C(C)(C)C)cc1] |

-continued
| Compound No | Structure |
|---|---|
| 107. | 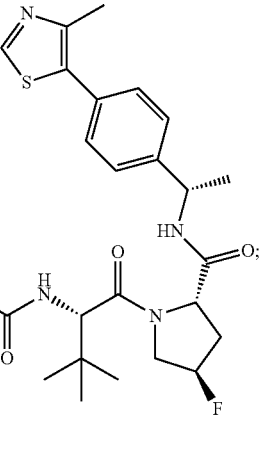 |
| 108. | 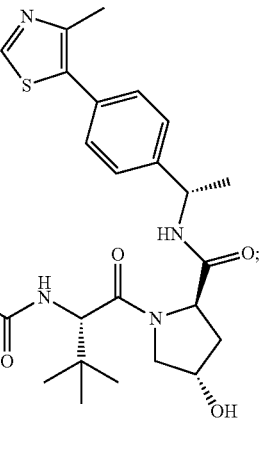 |
| 109. | 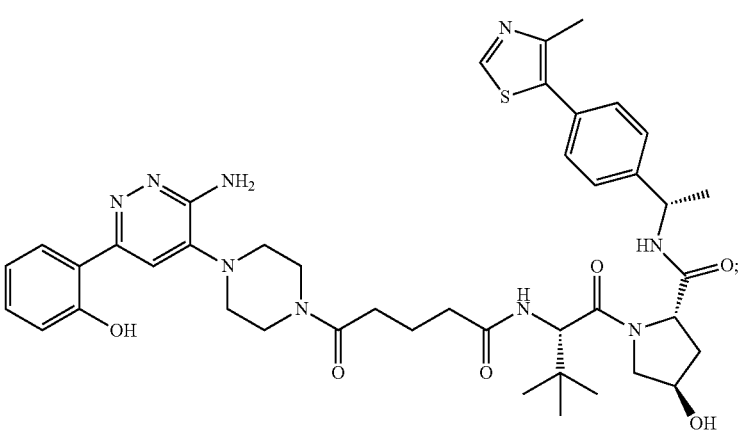 [SMILES: Cc1ncsc1-c1ccc([C@H](C)NC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] |

| Compound No | Structure |
|---|---|
| 110. | 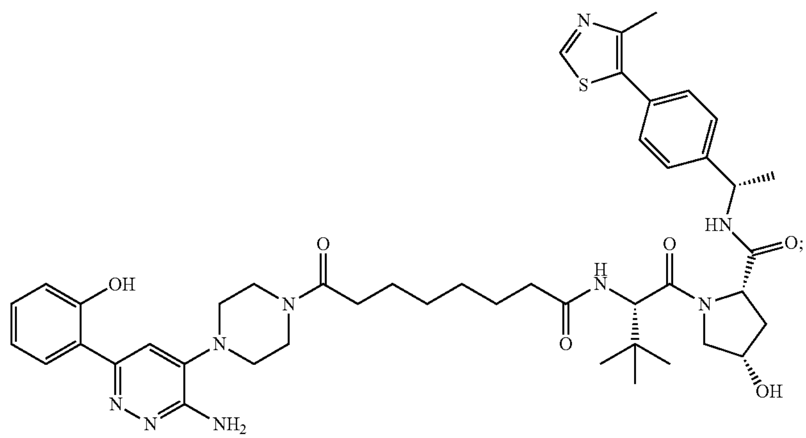 [SMILES: Cc1ncsc1-c1ccc([C@H](C)NC(=O)[C@@H]2C[C@H](O)CN2C(=O)[C@@H](NC(=O)CCCCCCC(=O)N2CCN(c3cc(-c4ccccc4O)nnc3N)CC2)C(C)(C)C)cc1] |
| 111. | 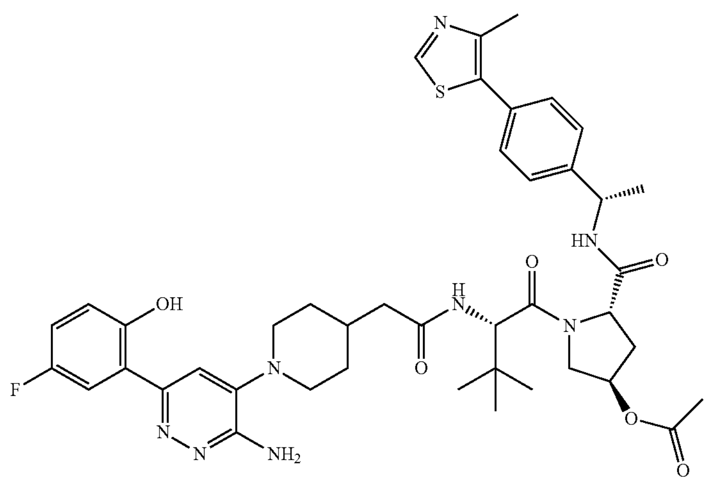 |
| 112. | 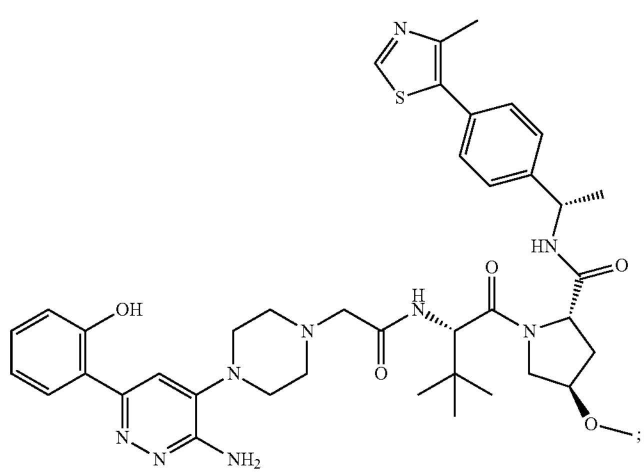 |

| Compound No | Structure |
|---|---|
| 113. | 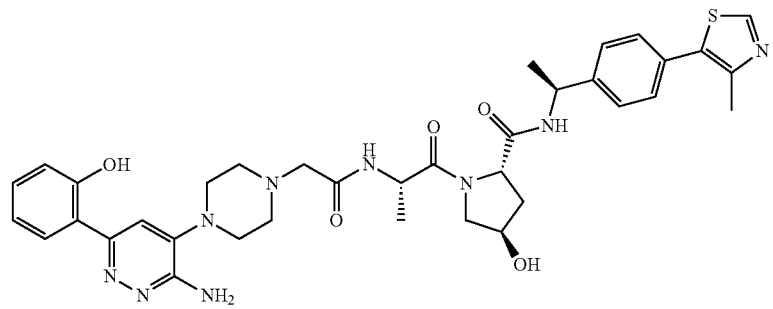 [SMILES: Cc1ncsc1-c1ccc([C@H](C)NC(=O)[C@@H]2C[C@@H](O)CN2C(=O)[C@H](C)NC(=O)CN2CCN(c3cc(-c4ccccc4O)nnc3N)CC2)cc1] |
| 114. | 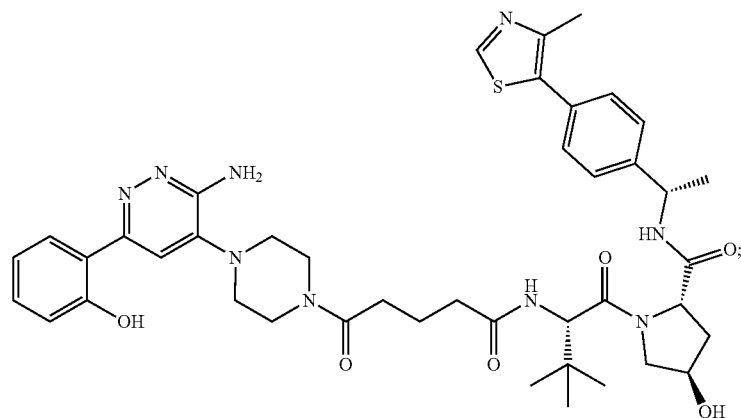 [SMILES: Cc1ncsc1-c1ccc([C@H](C)NC(=O)[C@@H]2C[C@@H](O)CN2C(=O)[C@@H](NC(=O)CCCC(=O)N2CCN(c3cc(-c4ccccc4O)nnc3N)CC2)C(C)(C)C)cc1] |
| 115. | 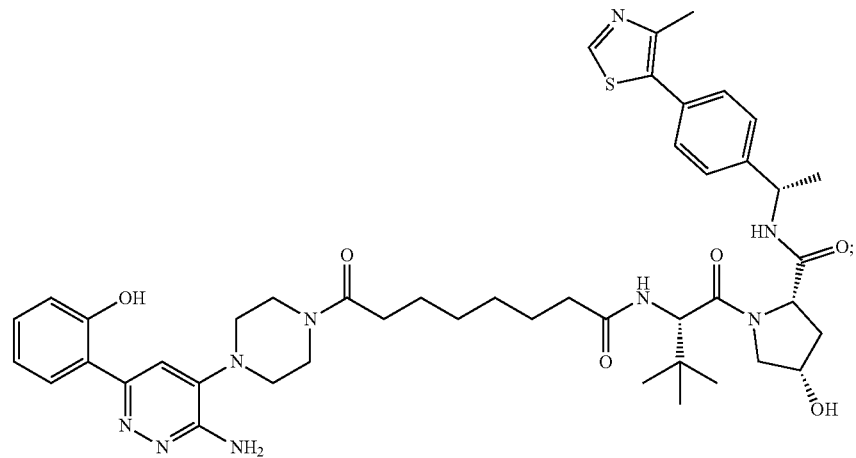 [SMILES: Cc1ncsc1-c1ccc([C@H](C)NC(=O)[C@@H]2C[C@H](O)CN2C(=O)[C@@H](NC(=O)CCCCCCC(=O)N2CCN(c3cc(-c4ccccc4O)nnc3N)CC2)C(C)(C)C)cc1] |

| Compound No | Structure |
|---|---|
| 116. | *(chemical structure)* |
| 117. | *(chemical structure)* |
| 118. | *(chemical structure)* | or a pharmaceutically acceptable salt or a stereoisomer thereof.

7. The method of claim 1, wherein the step of identifying the subject as a responder with at least one SMARCA2/4 degrader comprises:
  a) isolating a biological sample from the subject;
  b) determining a presence of at least one tumor specific alteration in the biological sample; and
  c) identifying the subject as a responder to said treatment if at least one of the tumor specific alterations is present.

8. The method of claim 1, wherein administering the at least one SMARCA2/4 degrader inhibits proliferation of prostate cancer cells in the subject.

* * * * *